(12) United States Patent
Carr et al.

(10) Patent No.: US 6,927,025 B1
(45) Date of Patent: Aug. 9, 2005

(54) METHODS FOR PROTEIN SCREENING

(75) Inventors: Francis Joseph Carr, Aberdeen (GB); Graham Carter, Aberdeen (GB); Anita Anne Hamilton, Aberdeen (GB); Fiona Suzanne Adair, Aberdeen (GB); Stephen Williams, Aberdeen (GB)

(73) Assignee: Biovation Limited, Aberdeen (GB)

( * ) Notice: Subject to any disclaimer, the term of this patent is extended or adjusted under 35 U.S.C. 154(b) by 0 days.

(21) Appl. No.: 09/518,813

(22) Filed: Mar. 3, 2000

Related U.S. Application Data

(63) Continuation of application No. PCT/GB98/02649, filed on Sep. 3, 1998.
(60) Provisional application No. 60/070,063, filed on Dec. 30, 1997, provisional application No. 60/070,062, filed on Dec. 30, 1997, provisional application No. 60/070,037, filed on Dec. 30, 1997, and provisional application No. 60/070,050, filed on Dec. 30, 1997.

(30) Foreign Application Priority Data

| Sep. 3, 1997 | (GB) | 9718552 |
|---|---|---|
| Sep. 18, 1997 | (GB) | 9719834 |
| Sep. 24, 1997 | (GB) | 9720184 |
| Sep. 29, 1997 | (GB) | 9720522 |
| Sep. 29, 1997 | (GB) | 9720523 |
| Sep. 29, 1997 | (GB) | 9720524 |
| Sep. 29, 1997 | (GB) | 9720525 |
| Jan. 22, 1998 | (GB) | 9801255 |
| Feb. 25, 1998 | (GB) | 9803828 |
| Apr. 14, 1998 | (GB) | 9807760 |
| May 23, 1998 | (GB) | 9811130 |

(51) Int. Cl.$^7$ .................................................. C12Q 1/68
(52) U.S. Cl. ........................ 435/6; 435/7.1; 435/7.32
(58) Field of Search .................... 435/5, 6, 7.1, 7.2, 435/7.21, 7.31, 320.1, DIG. 2–8, DIG. 22–24, 7.32; 530/300, 350; 536/23.1

(56) References Cited

U.S. PATENT DOCUMENTS

| 5,824,485 A | * 10/1998 | Thompson et al. ............ 435/6 |
| 5,952,171 A | * 9/1999 | McCarthy et al. ............ 435/6 |
| 5,955,269 A | * 9/1999 | Ghai et al. .................... 435/6 |

FOREIGN PATENT DOCUMENTS

| DE | 196 46 372 | 6/1997 | |
| EP | 0174753 | * 3/1986 | |
| WO | WO 91 05058 | 4/1991 | |
| WO | WO 92 02536 | 2/1992 | |
| WO | WO 92 18645 | 10/1992 | |
| WO | WO 93 03172 | 2/1993 | |
| WO | WO 95 11922 | 5/1995 | |
| WO | WO 95/11922 | * 5/1995 | ........... C07K/16/00 |
| WO | WO 95 34648 | 12/1995 | |
| WO | WO 98 48008 | 10/1998 | |

OTHER PUBLICATIONS

Johnstone, A.; Thorpe, R. Immunochemistry in Practice. Blackwell Scientific Publications, Oxford, England, 1987.*

Knappik A., et al., An Improved Affinity Tag Based on the Flag® Reptide for the Detection and Purification of Recombinant Antibody Fragments, BioTechniques, vol. 17, (1994) pp. 754–761.

Durrant, L.G., et al., Screening of Monoclonal Antibodies Recognizing Oncofetal Antifgens for Isolation of Trophoblasts from Maternal Blood for Prenatal Diagnosis, Prenatal Diagnosis, vol. 14, (1994) pp. 131–140.

Tavitian, B., et al., In vivo imaging of oligonucleotides with positron emission tomography, Nature Medicine, vol. 4, (1998) pp. 467–471.

Maskos, U ., et al., Parallel analysis of oligodeoxyribonucleotide (oligonucleotide) interactions.I. Analysis of factors influencing oligonucleotide duplex formation, Nucleic Acids Research, vol. 20, (1992) pp. 1675–1678.

Romisch, K., et al., Homology of 54K protein of signal–recognition particle, docking protein and two *E. coli* proteins with putative GTP–binding domains, Nature, vol. 340, (1989) pp. 478–482.

Tang, P ., et al., A High Affinity Digoxin–binding Protein Displayed on M13 is Functionally Identical to the Native Protein, Journal of Biological Chemistry, vol. 270, (1995) pp. 7829–7835.

Denzin, L.K., et al., Construction, Characterization, and Mutagenesis of an Anti–fluorescein Single Chain Antibody Idiotype Family, Journal of Biological Chemistry, vol. 267, (1992) pp. 8925–8931.

Mallender, W ., et al., Comparative Properties of the Single Chain Antibody and Fv Derivatives of mAB 4–4–20, Journal of Biological Chemistry, vol. 271 (1996) pp. 5338–5346.

Kraft, R., et al., Using Mini–Prep Plasmid DNA for Sequencing Double Stranded Templates with Sequenase™, BioTechniques, vol. 6, (1988) pp. 544–547.

Naryshkin, N.A., et al. Chemical Cross–Linking of the Human Immunodeficiency Virus Type 1 Tat Protein to Synthetic Models of the RNA Recognition Sequence TAR Containing Site–Specific Trisubstituted Pyrophosphate Analogues, Biochemistry, vol. 36 (1997) pp. 3496–3505.

Langer, P ., et al., Enzymatic synthesis of biotin–labeled polynucleotides: Novel nucleic and acid affinity probes, Proc. Natl. Acad. Sci., vol. 78) (1981) pp. 6633–6637.

(Continued)

*Primary Examiner*—Bennett Celsa
*Assistant Examiner*—Jon D Epperson
(74) *Attorney, Agent, or Firm*—Olson & Hierl, Ltd.

(57) ABSTRACT

This invention provides methods of protein/polypeptide screening based on the provision of libraries of individual proteins/polypeptides, which in turn can be screened for a number of activities, including cell binding and biological activity. Methods for recovering genes encoding such proteins/polypeptides are also provided.

8 Claims, No Drawings

OTHER PUBLICATIONS

Modjtahedi, H., et al., The human EGF receptor as a target for cancer therapy: six new rat mAbs against the receptor on the breast carcinoma MDA–MB 468, J. Cancer, vol. 67 (1993) pp. 247–253.

White, R., et al., The TATA–binding protein: a central role in transcription by RNA polymerasses I, II and III, Trends Genet, vol. 8, (1992) pp. 284–288.

Vincent, JP ., et al., Trypsin–Pancreatic Trypsin Inhibitor Association. Dynamics of the Interaction and Role of Disulfide Bridges, Biochemistry, vol. 11, (1972) pp. 2967–2977.

Phizicky, Eric, et al. Protein–Protein Interactions: Methods for Detection and Analysis, Microbiology Reviews, vol. 59, (1995) pp. 94–123.

Cash, Phillip, Protein mutations revealed by two–dimensional electrophoresis, Chromatography, vol. 698, (1995) pp. 203–224.

Hager D., et al., Elution of Proteins from Sodium Dodecyl Sulfate–Polyacrylamide Gels, Removal of Sodium Dodecyl Sulfate, and Renaturation of Enzymatic Activity: Results with Sigma Subunit of *Escherichia coli* RNA Polymerase, Wheat Germ DNA Topoisomerase, and Other Enzymes, Anal. Biochemistry, vol. 109, (1980) pp. 76–86.

Chen, HZ, et al., Prokaryotic Coupled Transcription–Translation, Methods in Enzymology, vol. 101, (1983) pp. 674–690.

Dingwall Colin, et al., Human immunodeficiency virus 1 tat protein binds trans–activation–responsive region (TAR) RNA in vitro, Proc. Natl., Acad. Sci., vol. 86, (1989) pp. 6925–6929.

Chan, Edward K.L., et al., The Small Nuclear Ribonucleoprotein SS–B/La Binds RNA with a Conserved Protease–Resistant Domain of 28 Kilodaltons, Molecular and Cellular Biology, vol. 7, (1987) pp. 2588–2591.

Siegel, et al., Elongation Arrest is Not a Prerequisite for Secretory Protein Translocation across the Microsomal Membrane, Cell Biology, vol. 100, (1985) pp. 1913–1921.

Cao, J., et al., Inhibition of Nascent–Peptide Release at Translation Termination, Molecular and Cellular Biology, vol. 16, (1996) pp. 7109–7114.

Langer, P ., et al., Enzymatic synthesis of biotin–labeled polynucleotides: Novel nucleic and acid affinity probes, Proc. Natl. Acad. Sci., vol. 78) (1981) pp. 6633–6637.

Marchuck, D., et al., Construction of T–vectors, a rapid and general system for direct cloning of unmodified PCR products, Nucleic Acids Research, vol. 19, pp. 1154.

Patton, W.F., et al., Development of a Dedicated Two–Dimensional Gel Electrophoresis System that Provides Optimal Pattern Reproducibility and Polypeptide Resolution, BioTechniques, vol. 8, (1990) pp. 518–527.

Madani, N.D., et al., Candida albicans estrogen–binding protein gene encodes an oxidoreductase that is inhibited by estradiol, Proc. Natl. Acad. Sci, vol. 91 (1994) pp. 922–926.

Rosenberg, A.H., et al., Vectors for selective expression of cloned DNAs by T7 RNA polymerase, Gene, vol. 56, (1987) pp. 125–135.

Molloy, P . et al., Separation and concentration of bacteria with immobilized antibody fragments, Journal of Applied Bacteriology, vol. 78 (1995) pp. 359–365.

Pawson, T. Protein modules and signalling networks, Nature vol., 373, (1995) pp. 573–580.

Prelich, G. et al., Functional identity of proliferating cell nuclear antigen and a DNA polymerase–δ auxiliary protein, Nature, vol. 326 (1997) pp. 517–520.

Porpaczy, Z., et al., Association between the α–ketoglutarate dehydrogene comples and succinate thiokinase, Biochim, Biophys.Acta., 749, (1983) pp. 172–179.

Weber, J. et al., Combined application of site–directed Mutagenesis, 2–Azido–ATP Labeling, and Lin–Benzo–ATP, Binding to Study the Noncatalytic Sites of *Escherichia coli* $F_1$–ATPase, J. Biol. Chem., vol. 268, (1993) pp. 6241–6247.

Mattheakis, L., et al., An in vitro polysome display system for identifying ligands from very large peptide libraries, Proc. Natl. Acad. Sci., vol. 91, (1994) pp. 9022–9026.

Hanes, J., et al., In vitro selection and evolution of functional proteins by sing ribosome display, Proc. Natl. Acad. Sci., vol. 94, (1997) pp. 4937–4942.

Hutchens, T ., et al., New Desorption Strategies for the Mass Spectrometric Analysis of Macromolecules, Rapid Comms. Mass Spec., vol. 7, (1993) pp. 576–580.

Jung, S., et al., Improving in vivo folding and stability of a single–chain–Fv antibody fragment by loop grafting, Protein Engineering, vol. 10, (1997) pp. 959–966.

* cited by examiner

METHODS FOR PROTEIN SCREENING

This application is a continuation of international application number PCT/GB98/02649, filed Sep. 3, 1998, pending, claiming priority to GB 9718552.4, filed Sep. 3, 1997, in Great Britain; GB 9719834.5, filed Sep. 18, 1997, in Great Britain; GB 9720184.2, filed Sep. 24, 1997, in Great Britain; GB 9720522.3, filed Sep. 29, 1997, in Great Britain; GB 9720525.6, filed Sep. 29, 1997, in Great Britain; GB 9720523.1, filed Sep. 29, 1997, in Great Britain; GB9720524.9, filed Sep. 29, 1997, in Great Britain; U.S. 60/070,063, filed Dec. 30, 1997, in the United States; U.S. 60/070,062, filed Dec. 30, 1997, in the United States; U.S. 60/070,037, filed Dec. 30, 1997, in the United States; U.S. 60/070,050, filed Dec. 30,1997, in the United States; GB 9801255.2, file Jan. 22, 1998, in Great Britain; GB 9803828.4, filed Feb. 25, 1998, in Great Britain; GB 9807760.5, filed Apr. 14, 1998, in Great Britain; and GB 9811130.5, filed May 23, 1998, in Great Britain.

The present invention relates to methods and compositions for the screening of proteins and polypeptides. In particular, the invention relates to methods involving the generation of gene libraries and the synthesis of individual proteins or polypeptides which can be screened in various ways. Particular embodiments include the use of so-called "ribosome display" protein or polypeptide arrays. The invention therefore provides for novel practical applications of displayed protein or polypeptide arrays in screening for biologically active polypeptides, for proteins which bind to receptors and for interactions of proteins with other molecules.

From the ongoing initiative to sequence the human genome has developed a major initiative to find polymorphisms or mutations in human genes which might have causal relationships with human diseases and, in addition, to alterations in the expression of genes which might relate to disease. This has given rise to many high-throughput screening technologies in order to find such polymorphisms, mutations or alterations in gene expression. In addition, such analyses are now being undertaken to analyse human responses to certain treatments and therefore to predict responsiveness to these treatments. Commonly, polymorphisms, mutations and gene expression changes are reflected in proteins produced by these genes and it is the actions of these proteins which can directly determine biological outcomes such as development of a disease or response to a treatment. In addition, most eukaryotic proteins are modified post-translationally and such modifications cannot be analysed at the gene level. It therefore follows that analysis of the screening for proteins and protein modifications is more likely to give a precise relationship of changes with disease compared to analysis of DNA or RNA.

The analysis of protein associations with disease has, to date, been dominated by 2D (two-dimensional) protein gel analysis from human tissue or cells. For this technology, cellular proteins are usually separated on the basis of charge in one dimension and on the basis of size in the other dimension. Proteins can either be identified with reference to the electophoresis migration pattern of a known protein or by elution of the protein from the electrophoretically separated spot and analysis by methods such as mass spectrometry and nuclear magnetic resonance. However, limitations of the 2D protein gel method include the limited resolution and detection of proteins from a cell (typically only 5000 cellular proteins are clearly detected), the limitation to identification of separated proteins (for example, mass spectrometry usually requires 100 fmoles or more of protein for identification), and the specialist nature of the technique. In addition, the analysis of post-translational modification of proteins by 2D gel analysis is limited and protein-protein binding interactions cannot be detected by this method.

A large number of cellular processes are controlled by the transient interaction between a modifying enzyme and its protein substrate. Such interactions are difficult to detect by conventional methods. Protein modifying enzymes such as kinases, phosphatases, transferases, proteases etc. control all manner of fundamental cellular processes (Pawson, Nature, 373 (1995), pp573) and have also been shown to be involved in disease pathways. These transient protein/protein interactions can result in a number of different effects some of which can be measured. The kinetic properties of a protein can be altered resulting in altered binding of substrates (Prelich et al., Nature 326, (1989) pp 517) or altered catalysis (Porpaczy et al., Biochim. Biophys. Acta, 749 (1983), pp 172). Protein/protein interactions can cause the formation of a new binding site e.g. an ATP binding site is formed by the interaction of the a and b subunits of the *E. coli* ATPase (Weber et al., J. Biol. Chem., 268, (1993), pp 6241). Substrate specificity of a protein can be altered by protein/protein interactions as exemplified by the interaction of different transcription factors with RNA polymerase directing the polymerase to specific promoters (White & Jackson, Trends Genet., 8, (1988), pp 284). Alternatively protein/protein interactions can cause inactivation, for example when a protein interacts with an inhibitor (Vincent & Lazdunski, Biochemistry, 11, (1972), pp2967).

There are methods disclosed in the art which rely on the generation of proteins or polypeptides from gene libraries. However, one major disadvantage with such methods is that the proteins or polypeptides are generated as a "pool" which is then screened. There is a need for screening methods which allow for rapid identification of individual proteins or polypeptides, and which in turn will also allow for identification of genes coding for such proteins or polypeptides.

Thus, in a first aspect, the present invention provides a method of screening proteins or polypeptides which comprises forming a gene library and synthesising individual proteins or polypeptides which can then be screened. In the context of the present invention, the term "individual proteins or polypeptides" means that the proteins or polypeptides expressed from the gene library are individually identifiable, rather than forming part of a pool. Thus, for instance, the proteins or polypeptides can be expressed as an array wherein each protein or polypeptide occupies a distinct point or area within the array. For example, a gene library may be generated in the form of colonies or plaques, which in turn can be picked off individually and arranged in an array. Expression of the genes will ion turn result in an array of proteins or polypeptides in an array format, each occupying a distinct point or area.

The proteins or polypeptides generated from the gene libraries may be termed "synthetic proteins or polypeptides" produced by in vitro methods such as in vitro transcription and translation, ribosome display and phage display. Thus, they may be distinguished on that basis from "natural proteins" derived directly from tissue or cell extracts.

Thus, the methods described herein allow for screening of proteins and polypeptides and post-translational modifications using gene libraries as the starting point for synthesis of "synthetic" proteins or polypeptides. In general this is achieved by the generation of arrays of proteins or polypeptides as a means for screening them. In particular, the arrays are generated by in vitro transcription and translation methods.

A common theme of the present invention is that the methods provided each permit the rapid identification of a "synthetic" protein or polypeptide by virtue of its corresponding mRNA or gene sequence.

Other embodiments of the present invention provide for novel techniques for display of proteins on ribosomes and use of such methods for screening proteins or polypeptides and post-translational modifications, and for novel methods for screening for specific proteins or polypeptides binding to other molecules such as receptors.

The ribosome represents a collection of proteins whose coordinated activities accomplish the act of translation. The basic form of the ribosome is conserved although there are appreciable differences in the size and proportions of RNA and proteins in the ribosomes of prokaryotes and eukaryotes, and in organelles. All ribosomes consist of two main subunits, in bacteria the 50S and 30S subunits, and in eukaryotes the 60S and 40S subunits. Protein synthesis starts when the ribosome attaches to mRNA either at the 5' cap in eukaryotes or adjacent to the translational initiation codon in prokaryotes (usually AUG) and continues by the successive loading, directed by the mRNA sequence, of amino acids onto a peptidyl-tRNA molecule carrying the nascent polypeptide chain. Translation terminates usually at a stop codon where the ribosome disassociates from the mRNA. In the absence of a stop codon, the ribosome is thought to progress to the end of the mRNA molecule before disassociation occurs with the assistance of release factors. Translation termination therefore disconnects the protein from the mRNA molecule encoding it. If the ribosome is arrested during protein synthesis, then the protein and mRNA will remain connected whilst complexed with the ribosome.

The biochemical process of generating synthetic proteins on ribosomes has several advantages over existing methods for generation of synthetic proteins using live organisms. Methods of selecting proteins as the carrier of a particular phenotype and subsequently determining the corresponding genotype have relied mainly on living cells to provide a link between genes and proteins commonly using bacteriophage, viruses and bacterial cells displaying the desired protein. For a diverse collection of proteins encoded by a DNA library, the use of live cells has several disadvantages. For example, the protein diversity can be reduced by the requirement for transformation or infection of bacterial or eukaryotic cells which is limited by the low efficiency of DNA or infectious particle uptake. Furthermore, the biological production of diverse proteins is subject to the particular environment of the living cell which can select against certain proteins and can lead to the variations in protein folding which can also select against certain proteins. Finally, if diversification of individual proteins during successive selection rounds is required, genetic mutation techniques are difficult to apply to in vivo systems due to the need to switch between DNA and live cells for the diversification and screening.

In vitro methods for the selection of a polypeptide potentially offer advantages over in vivo methods by eliminating the need for uptake of genes into cells and by controlling the environment for mRNA and protein production. In vitro transcription and translation reactions have been used for many years as a means of generating polypeptides directly from DNA and it has been shown that specific mRNAs can be enriched by the immunoprecipitation of polysomes (e.g. Payvar, F. and Schimke, R. T., Eur. J. Biochem., vol 101 (1979) p1844–1848) using antibodies to select the specific polypeptides. This so-called "ribosome display" technique has more recently been adapted for the selection of peptides (Mattheakis. L. et al, PNAS 91: 9022, 1994 and PCT95/11922) and proteins (Kawasaki, G., PCT91/05058 and Hanes & Pluckthun, PNAS, vol 94 [10] :4937, 1997). The methods described by Mattheakis. L. et al (PNAS 91: 9022, 1994) uses ribosome display systems for identification of ligands from peptide libraries. The method uses chloramphenicol for ribosome translation arrest which induces stalling in ribosome translation by binding the 50S subunit of the prokaryotic ribosome complex. A disadvantage of this method is that it will cause translation arrest regardless of the length of the nascent peptide and thus most polypeptide molecules will be incomplete. For efficient screening of polypeptides from a DNA library following transcription/ translation, it is clearly desirable to maximise the yield of full-length polypeptides associated with mRNA.

The methods described by Mattheakis and Dower in PCT95/11922 include additional measures to stall ribosomes principally through the use of "Tethered Nascent Peptides" which are peptide portions of a fusion polypeptide molecule, adjacent to the polypeptide portion for screening, which interact or bind with the encoding polynucleotide in order to maximise the yield of polypeptides associated with mRNA. As with Mattheakis. L. et al (PNAS, ibid), this method would be expected to cause premature translational arrest and would also be expected to distort the proper folding of some proteins for screening. Thus, a range of sizes of polypeptide molecules would be expected by the methods described by Mattheakis and Dower which would reduce the probability of isolating specific polypeptides encoded by the DNA library. In the method of Hanes & Pluckthun (ibid), there is provided a method to optirnise the yield of correctly folded protein and its encoding mRNA while both are still attached to the ribosome. The method includes stalling the translation process by increasing magnesium acetate concentration and correct folding of proteins by the manipulation of the physical reaction conditions. However, the only measure to increase the yield of full-length protein is to eliminate stop codons from the mRNA by manipulating the corresponding genes and adding a 3' spacer region in order to tether the folded protein on the ribosome. Whilst this method should increase the proportion of fill-length polypeptides when compared to earlier methods, the method provides no measures to prevent run-off translation from the end of the mRNA and the stalling strategies provided suffer from the same limitations as with Mattheakis and Dower (ibid) whereby premature translational arrest would be expected. In addition to the limitations described for each of the methods above, none of the methods provide a means to block new translational starts late in the translation reaction prior to testing of translated polypeptides. Thus, a range of sizes of polypeptide molecules would be expected by these methods which would reduce the probability of isolating specific polypeptides encoded by the DNA library. There is therefore a need for new methods for ribosome display which maximise the yield of full-length polypeptides whilst minimising the presence of nascent incomplete polypeptide chains in order to efficiently screen a DNA library for specific polypeptides.

Therefore another embodiment of the present invention ("ribosome display") provides for a new in vitro method is provided for the display of proteins on ribosomes linked to the corresponding mRNA. Further embodiments of the present invention use polypeptide display methods, particularly ribosome display, to specifically discover biologically active or inhibitory polypeptides without any knowledge of the molecular target for these polypeptides, to specifically discover the molecular binding sites for polypeptides which bind to cells or tissues, and to specifically discover new protein-protein binding interactions.

In a specific embodiment of the present invention for discovery of biologically active polypeptides ("biological screening"), there is provided a new method to directly select a biological phenotype encoded by a DNA library and expressed via polypeptide display. Whilst display of polypeptides on microorganisms and transcription-translation methods have provided a link between a useful binding phenotype and genotype, these methods have largely been limited to detection of polypeptides by virtue of binding to a ligand such as an antigen or a chemical whereby the ligand is known and is usually available in a reasonably pure preparation. The identification of displayed polypeptides by virtue of binding directly to whole living cells has proven difficult. In many cases, the screening for binding phenotypes is a substitute for the isolation of biologically active polypeptides which display a useful biological phenotype upon interaction with target living cells. In such cases, it is necessary, having isolated the binding phenotype and determined the corresponding genotype, to then test the binding phenotype for biological activity. As only a proportion of polypeptides with a specific binding phenotype may provide the required biological activity, this phenotypic selection process is therefore inefficient and is reliant on a surrogate binding screen which may not select for biologically active polypeptides. In some cases where the ligand for phenotypic screening is not available or not known, then screening for new biologically active polypeptides may not be possible. Therefore, the present invention also provides a new method to directly select a biological phenotype encoded by a DNA library and expressed via polypeptide display.

In a specific embodiment of the present invention to discover the molecular binding sites for polypeptides which bind to cells or tissues ("ligand-directed screening"), methods are provided which apply to large DNA libraries encoding protein molecules which can be screened in such a way as to enable the replication of DNA molecules encoding protein molecules of interest, especially those labelled in the method of the current invention. In order to determine the target receptor protein for a particular ligand molecule, it is feasible to use the ligand for the selective isolation of the target receptor prior to subsequent analysis of the target and it's molecular identification. However, where the affinity of binding by the ligand to it's receptor is low or the ligand and/or receptor are in low abundance, it can be very difficult to isolate the receptor using the ligand and commonly candidate receptors have to be tested by, for example competition assays, in order to determine the identity of the receptor. Furthermore, for the subsequent creation of molecules which block ligand binding (for example, receptor antagonists) or molecules which substitute for the binding of ligand (e.g. agonists), a purified or enriched receptor preparation must be tested with a range of candidate binding molecules (e.g. antibodies) for isolation of molecules which bind at the ligand binding site. Clearly, where the receptor is not available in a purified or enriched form or where the receptor identity is not known, isolation of receptor binding molecules is very difficult. New tools are therefore required for the efficient isolation of target receptors and for the isolation of molecules which bind specifically at the ligand-binding site on the receptor which might act, for example, as agonists, antagonists or simple targeting molecules. It is a specific aspect of the present invention that the molecular binding sites for polypeptides which bind to cells or tissues can be discovered. The method is based on the principle of using a ligand, which binds to a proteinaceous receptor, to label other protein-complexes binding to the receptor immediately adjacent to the ligand. On this basis, these adjacently binding proteins can then be used as binding agents to isolate the receptor and also, in some cases, to isolate protein molecules adjacent to the receptor. Furthermore, these adjacently binding proteins can subsequently be rebound to the receptor along with other proteins including proteins which bind at the ligand binding site such that the adjacently binding proteins can then label other protein-complexes binding immediately adjacent to themselves including proteins which bind at the ligand binding site. In this manner, one or more protein-complexes which bind at the ligand binding site can be labeled and subsequently isolated and tested for useful properties such as receptor blocking, agonism or antagonism of the receptor. In particular, the invention is useful for the labelling and isolation of molecules on a cell surface and, in particular, on whole tissues. The present invention therefore provides methods for screening DNA libraries encoding protein molecules in such a way as to enable the replication of DNA molecules encoding protein molecules of interest.

In a further embodiment of the present invention specifically relating to new protein-protein binding interactions ("protein-protein interactions") including those occurring between intracellular polypeptides, there are provided methods for the binding of a polypeptide to a ligand or a polypeptide to another polypeptide in such a way so as to generate a detectable or selectable property which then allows isolation of genes encoding the binding polypeptides(s).

The various embodiments of the present invention are detailed in more detail below.

Protein "Arrays"—in this embodiment of the present invention, there are provided novel methods for screening proteins and polypeptides and post-translational modifications using gene libraries as the starting point for synthesis of synthetic proteins. In this embodiment, these gene libraries provide the basis for segregating individual proteins or groups of proteins in order to detect polypeptides and to detect polypeptide modifications. The method principally avoids the use of protein gel electrophoresis. The invention provides methods for the high-throughput analysis of proteins in normal and disease tissues or cells principally to detect differences between normal and disease proteins and also for the analysis of protein changes in relation to drug and other disease treatments. The method also provides for high-throughput analysis of the binding or biological activity of libraries of proteins or polypeptides when exposed to living cells or tissues. Furthermore, the method also provides for the protein "fingerprinting" of individuals as an alternative to genetic fingerprinting in order to identify individuals and different tissues or cells. It is an important feature of the present invention that proteins are analysed either in pools or in arrays of individual proteins whereby, once modifications, binding or biological activity are detected using a variety of methods, the identity of the protein can be determined either directly or indirectly by either its location in a particular pool or its location at a particular position in an array. Equally, it is an important aspect of the present invention that the methods allow for the comparative detection of differences in proteins or protein modifications between different tissues or cells and therefore the methods constitute a screen for these differences.

The method is based primarily on the use of synthetic proteins produced by recombinant DNA methods, especially proteins produced from one or more genes by in vitro transcription and translation (IVTT). One preferred aspect of the present invention is the generation of synthetic proteins by IVTT with their subsequent immobilisation onto solid phases prior to screening for protein modification or for protein-protein binding interactions. It is an important aspect of this embodiment of the present invention that the generation of synthetic proteins from arrays of genes (such as cDNAs cloned into vectors designed to facilitate IVTT) is undertaken in such manner that synthetic proteins, once tested for protein modification, binding or biological activity can easily be identified by reference to the originating genes encoding these synthetic proteins whereby the gene sequence will reveal the identity of the protein. Such gene arrays are, for example, provided by picking individual cDNA clones or mixtures of clones into specific loci in an array (such as in the wells of a microtitre plate). Following IVTT (usually after amplification of the cDNAs by methods such as PCR), protein samples from each loci in the array can be taken and immobilised or dispensed into specific loci in another array, for example into alternative microtitre plates or onto a solid phase where samples are dispensed at individual loci on the solid phase. Where specific protein modifications or protein binding events are detected from protein samples in the array, then the specific gene encoding these proteins can be located and sequenced in order to identify the protein of interest.

It is also within the scope of the preferred embodiment present invention that the cDNA library may encode a set of variable molecules such as immunoglobulin variable regions (commonly as single-chain Fv regions, referred to as SCAs (single-chain antibodies)). Such variable molecules, when dispensed to specific loci in arrays, then have the ability to bind to other specific molecules (usually proteins) from cell or tissue samples. These cell or tissue molecules, by virtue of binding to the variable molecules in the array, then essentially provide for an ordered array of cell or tissue molecules. The presence of cell or tissue molecules in such arrays or modification of these molecules such as by phosphorylation or interaction with other proteins can then be addressed in the array. The identity of such cell or tissue molecules can subsequently be determined by several methods especially where the original variable molecules can be retrieved in isolation and used to retrieve the cell or tissue molecule(s) in isolation. The identity of such cell or tissue molecules can then be determined by classical biochemical means or, where these are proteins, by protein sequencing or by methods such as 2D gel migration properties. Alternatively, the identity of such proteinaceous cell or tissue molecules can be determined using a protein display system such as the ribosome system included in this patent whereby a cDNA library is used to generate a library of proteins linked to their genes (or RNA representation of the gene) such that, upon binding to a specific variable molecule, the identity of the binding protein can be determined by determining the nucleotide sequence of the associated gene.

As an alternative to the use of IVTT for generation of synthetic proteins in the formation of protein arrays, another aspect of the microarray embodiment of the invention is the use of "polypeptide display" methods for generating synthetic polypeptides with useful phenotypes from gene libraries encoding a large mixture of polypeptides whereby the corresponding genes can be recovered swiftly and easily. In vitro methods of polypeptide display have been developed which allow greater scope for the type of protein displayed than cell based display systems and in particular display of proteins associated with ribosomes ("ribosome display") which can provide proteins linked via the ribosome complex to corresponding mRNAs which can then be sequenced in order to reveal the identity of the protein. The present method can also incorporate other protein display methods such as phage display.

In one embodiment of the present method, protein modifications are screened by creation of a gene library which is then used to create synthetic proteins for example by IVTT to successively produce mRNA and protein from such vectors preferably under such conditions as to maximise yield of full-length synthetic proteins which have disassociated from mRNA In order to avoid over-representation of proteins or polypeptides from abundant mRNA species, the gene library is normalised. Through the incorporation of modified amino acids such as biotinyl-lysine or the incorporation of an amino acid sequence tag encoded by the plasmid vector or introduced by PCR, or through chemical modification of the protein, the synthetic protein can next be immobilised onto a solid phase such as a magnetic bead via a biotin binding protein (e.g. streptavidin) or via a sequence tag binding protein such as an anti-tag antibody. In a screen for protein modification, through appropriate distribution of the starting genes, small pools of proteins or individual proteins are produced in arrays such as in microtitre wells and immobilised in these arrays.

Alternatively, the synthetic proteins might be produced in arrays as individual small pools of proteins or individual proteins and then transferred individually (either manually or by use of an automatic dispenser) to different loci on a flat solid phase such as on a glass "chip" whereby the proteins interact with functional moieties on the solid phase resulting in immobilisation. Next, these synthetic proteins are treated with extracts of tissues or cells whereby enzymes present in these tissues or cells can effect modifications to the synthetic proteins. Finally, such modifications are then be detected using specific detection systems such as fluorescently labelled anti-phoshotyrosine antibodies. If the signal from the detection system is compared from replicate arrays of synthetic proteins which are modified by different extracts of tissues or cells, then differences in these signals between replicate synthetic proteins will indicate differences in the protein modification activities from these different tissues or cells.

In another embodiment of the present method, protein-protein binding interactions are screened by creation of a gene library which is then used to create synthetic proteins such as by IVTT, preferably in such vectors and under such conditions as to maximise yield of full-length synthetic primary proteins which have disassociated from mRNA. Through the incorporation of modified amino acids or an amino acid sequence tag, or through chemical modification of the protein, or by use of a chemically reactive solid phase, the synthetic primary protein can be immobilised onto a solid phase either immediately after synthesis or following the interaction with secondary proteins to form any protein-protein interactions. Through appropriate distribution of the starting genes, as in screens for protein modification, small pools of primary proteins or individual proteins are produced in arrays such as in microtitre wells or on glass chips and immobilised in these arrays. Next, these synthetic primary proteins can optionally be treated with extracts of tissues or cells whereby enzymes present in these tissues or cells can effect modifications to the synthetic proteins. Next, one or more (including a library of) secondary proteins are then added in order to form any suitable binding interactions of appropriate secondary proteins with the primary proteins. Optionally, these secondary proteins may be synthetic and displayed on ribosomes or phage such that the identity of the secondary protein can subsequently be determined.

Alternatively, the secondary proteins could be natural proteins derived from tissues or cells. Protein-protein binding interactions between primary and secondary proteins can then be detected by a range of methods. For example, the primary protein can be immobilised onto a solid phase and the presence of a synthetic secondary protein determined via an amino acid sequence tag incorporated into the secondary protein with detection using specific detection systems such as fluorescently labelled anti-tag antibody. Alternatively, if the secondary protein is associated with its coding nucleic acid such as for ribosome or phage display, then the secondary protein can be detected by a PCR assay for the associated nucleic acid. Alternatively, binding of the secondary protein may be detected through the action of the secondary protein in blocking a site on the synthetic primary protein which is detected in the assay system and which becomes blocked if a secondary protein binds. Alternatively, if the secondary protein is a natural protein, it may be labelled directly after binding, for example by addition of a UV-activatable biotin molecule, and detected directly, or it may be laser vapourised and detected by MALDI (Matrix Assisted Laser Desorption Ionisation) and mass spectrometry. If the binding of secondary proteins to replicate arrays of synthetic primary proteins is compared betweendifferent extracts of tissues or cells, then differences in these signals between replicate synthetic proteins will indicate differences in the protein-protein binding activities from these different tissues or cells.

It will be obvious that by detecting a range of protein modifications and by detecting protein-protein binding with a common detection format such as by using fluorescent labelled antibodies to protein tags or epitopes, then simultaneous parallel screening for a number of different protein modifications could be undertaken in order to screen for differences between different tissues and cells.

In another embodiment of the present invention, protein-protein interactions are used as the basis for forming arrays of secondary proteins, especially natural tissue or cell derived proteins which normally would be very difficult to comprehensively array using standard technology. The primary proteins comprise a highly diverse set of proteins such as immunoglobulins which provide a diverse set of binding specificities for a set of secondary proteins such as natural proteins from tissue or cell extracts or synthetic proteins from a ribosome or phage displayed protein library. As an example, the primary proteins would derive from a Ribosome displayed single-chain antibody (SCA) variable region library formed by direct PCR amplification of immunoglobulin variable regions from mammalian B lymphocytes and cloning into suitable vectors for in vitro transcription. Members of the SCA library are arrayed either individually or in groups into microtitre wells or directly on a solid phase such as a glass chip and the SCA proteins are produced by IVTT and immobilised via a protein tag or by direct chemical coupling to a solid phase. Then a mixture of natural proteins from a tissue or cell extract or a mixture of synthetic proteins originating from a gene library (for example ribosome or phage displayed proteins) is added in bulk to the array of primary proteins such as SCAs whereby the binding specificity imparted by the primary proteins for the secondary proteins leads to arraying of the secondary proteins with either single secondary proteins or groups of secondary proteins binding to individual SCAs. The achieved array of secondary proteins is compared between different extracts of tissues or cells, then differences in these signals between replicate synthetic proteins will indicate differences in the presence of proteins from these different tissues or cells.

Alternatively, these proteins can also be tested for various modifications such a phosphorylation by using, for example, fluorescently labelled antibodies to detect these modifications.

It is a particular aspect of the present invention that proteins, either synthetic or natural, are distributed into arrays of single or multiple proteins in order to provide for comparisons of the presence or modification of these individual single or multiple protein members of the array between different tissue or cell extracts or to provide for analysis of the binding or biological activities of these protein members on live cells or tissue. Whilst arrays can readily be performed in microtitre plates by distributing individual members of groups of clones from a cDNA library in the individual wells of the plate, this manual (or robot-directed) arraying technology results in the physical barrier of the walls of the wells between different samples and this makes it difficult to add subsequent solutions such as wash solutions and libraries of secondary proteins quickly and accurately. In addition, the use of microtitre plates provides a limit to the density of arrayed proteins, such limit being dictated by the density of wells in the microtire plates available. It is therefore desirable to have methods which do not require arraying of proteins without physical barriers between the proteins.

In another embodiment of the invention where arrays of proteins are formed without physical barriers, the spatial distribution of proteins into arrays is achieved either by directly spatially immobilising individual synthetic proteins derived from a gene library by, for example, ribosome display or by spatially immobilising nucleic acids, especially synthetic DNA, to which nucleic acids associated with a synthetic protein library are annealed in order to indirectly spatially immobilise members of the protein library. For direct spatial immobilisation, either synthetic proteins derived from a tissue or cell gene library are immobilised or synthetic protein probes such as SCAs are immobilised such that a mixture of secondary proteins can then be added whereby these would be spatially distributed according to their binding specificities for individual protein probes. Thus, the invention provides for new types of protein chips (cf Hutchens & Yip, Rapid Comms. Mass Spec. 7, (1993), pp576). Immobilisation of synthetic proteins on the chip is achieved by either covalent or non-covalent linkage. Particularly convenient is immobilisation using biotin moieties incorporated into the protein by addition of biotinyl lysine tRNA during the translation reaction. Having incorporated biotin, synthetic protein molecules can then readily be immobilised onto solid-phase streptavidin or solid-phase anti-biotin antibodies. Typically, this is facilitated by the use of a robotic dispenser which can aliquot protein samples produced by in vitro transcription and translation onto specific positions in a multiwell plate or onto a solid phase such as a glass chip. Such a robotic dispenser is particularly important for creating replicate arrays of synthetic proteins where identical proteins are immobilised at identical loci within the replicate solid phases. In relation to direct immobilisation using biotinyl lysine, free biotinyl lysine tRNA which has not incorporated into the synthetic protein can present difficulties in some samples whereby the free biotin groups block access to immobilised streptavidin molecules. Conveniently, this can be overcome by ensuring exhaustion of the biotinyl lysine tRNA in the translation reaction mixture (nascent proteins can then be completed by addition of unmodified lysine tRNA); alternative strategies are the use of solid phases with the number of biotin binding sites in excess of numbers of lysine-associated biotin molecules or a molecular sieve filtration step to remove small molecules such as biotinyl-lysine tRNA. Another strategy is to add into the translation reaction mixture, at the end of the translation period, a synthetic mRNA template encoding a lysine rich (poly)peptide which can then incorporate excess free biotinyl tRNAs. Such a template would also encode a peptide sequence (for example, a polyhistidine tail) which subsequently could be used to remove the lysine rich synthetic protein from the reaction mix (for example, using beads with antibodies against the polyhistidine tail). In such manner, the free biotinyl-lysine groups would be removed from the translation mixture prior to immobilisation of the synthetic proteins.

Non-covalent attachment of the proteins can also be facilitated by labelling the proteins for example with biotin using a commercially available reagent such as Sulfo-SBED (Pierce & Warriner, Chester, UK) which is then reacted with avidin. Covalent attachment of the proteins can also be achieved by activating the proteins with reactive species to facilitate cross-linking by any of the conventional ways, such as those described in OSullivan et al., (Anal. Biochem. 100 (1979),108). Attachment of proteins could also be facilitated by inclusion of specific amino acids sequences within the synthetic proteins such as terminal poly-histidine sequences which can then bind to either solid phase nickel chelates or anti-poly-histidine antibodies as a means for achieving imobilisation. Alternative methods for directly binding synthetic proteins would include binding of ribosome displayed proteins by immobilising the associated RNA using, for example, an RNA binding protein (such as HIV tat protein) or by annealing the RNA to synthetic DNA molecules on the solid phase.

For indirect immobilisation of proteins via nucleic acids, the associated mRNA in a protein-ribosome-mRNA complex may be produced with a nucleotide sequence tag originally encoded by the plasmid vector encoding the mRNA. The nucleotide sequence tag may be variable or randomised in the plasmid vector preparation, for example by producing the plasmid vector using a synthetic region encoded by a random oligonucleotide mixture (with appropriate ends which anneal to the vector) to place random a sequence tag at, for example, the 5 end of the mRNA. Following production of the protein-ribosome-mRNA complexes from the gene library, the mRNA sequence tags may then be annealed to an array of synthetic oligonucleotides individually positioned over a solid surface such as a glass slide (a "DNA biochip"). In this manner, individual proteins may finally be positioned at specific locations on the biochip. The spatially arrayed proteins may then be analysed for modification by tissue or cell extracts using, for example, fluorescent antibodies to screen for these modifications. In addition, the arrays may be used for identification of proteins which bind or modify the individual proteins on the biochip. The identity of the modified proteins or the proteins involved in protein-protein interactions may subsequently be determined from the known sequence of the immobilised oligonucleotide on the chip whereby this sequence is used to probe the plasmid library (for example, by PCR) in order to identify the specific gene associated with the complementary sequence tag within the plasmid library. The identity of the proteins may alternatively be achieved by PCR amplification of the mRNA sequence associated with the individual protein. This embodiment therefore relates to a protein array biochip with, in principle, individual proteins located at individual loci on the chip. Alternatively, the identity of the protein may be determined if the primary or secondary synthetic protein is produced with a random set of protein sequence tags which can be interrogated using, for example, a mixture of antibodies against those sequence tags. If, for example, the synthetic proteins are produced in such a manner that one terminus comprises either a random or semi-random stretch of amino acidseach of which can be detected by an antibody from a library of antibodies with appropriate labels, then the binding of one or more specific antibodies can determine the identity of the synthetic protein. For example, if one terminus of the protein contains a random 8 amino acid sequence tag and a library of SCAs has been constructed and enriched for SCAs binding to an equivalent mixture of synthetic peptides, then individual or small groups of SCAs will bind to specific peptides and the peptides (and therefore synthetic proteins) can be identified by knowledge of the specificity of individual SCAs.

Encompassed by the present invention are also methods where mixtures of modified proteins or interacting proteins are preselected prior to analysis of differences between different tissues or cells. For example, primary synthetic proteins created by display methods such as ribosome display where individual MRNA molecules encoding a protein remains attached to the protein are subjected to treatment by tissue or cell extracts and then subjected to selection using antibodies against these modifications immobilised on a solid phase. Thus, modified proteins with associated nucleic acids are isolated and the profile of proteins isolated can be determined by several means including a simple analysis of PCR products, for example by agarose gel electrophoresis, and comparison of results from treatments with different cells and tissues. Similarly, for primary natural proteins which are then used to "capture" secondary synthetic proteins by protein-protein binding, interacting proteins could be isolated using, for example, an antibody against a tag on the secondary synthetic protein and a profile of the interacting proteins determined again by analysis of PCR products from the nucleic acids associated with the synthetic protein.

Encompassed by the present invention are also methods where synthetic proteins generated from gene libraries are subjected to protein gel electophoresis for the analysis of protein modification or protein-protein binding. It is well documented that post translational modifications such as proteolysis or phosphorylation change the electrophoretic mobility of a protein (Phizicky & Fields Microbiol. Rev., 59, (1995), pp94). One embodiment of the invention therefore provides a method whereby disease associated protein modifications would be detected using 2D gel electrophoresis. For example, a cDNA library for subsequent IVTT or ribosome display would be constructed. To facilitate subsequent purification of the proteins, a 3 tag such as His or Flag may be incorporated into the transcription vector used. This will be achieved by standard molecular biology techniques that will be familiar to those skilled in the art. To facilitate subsequent detection of the proteins, they may be labelled during the translation process with labels such as 35S or biotin. Following translation, the proteins could if required be purified to remove ribosomes and other factors for example by passage of the translation mixture over an affinity matrix containing ligands such as anti-Flag antibodies or nickel where the proteins have 3 flag or ployhistidine tags or using anti-ribosome antibodies to remove ribosomal components onto a solid phase or by simple ultracentrifugation of ribosomes. Protein from a clinical sample (either unlabelled or labelled, for example through reaction with a fluorescent moiety) would then be incubated with the purified in vitro translated library to effect either modification or protein interactions withy the synthetic protein. The total reaction would then be separated by 2D gel electrophoresis (Cash, J. Chromatography 698 (1995), p203) and the resultant gels analysed using appropriate computer software such as Phoretix-2D (Phoretix International, Newcastle upon Tyne, UK). A control reaction would be performed such that the synthetic protein library would be reacted with total protein from an alternative clinical sample, for example a normal sample if the first sample is a diseased sample. Disease associated modifications or protein/protein interactions would be identified as unique bands seen with the diseased proteins and not seen in the control proteins. In order to facilitate rapid identification of the gene associated with protein identified by the 2D gel analysis, the synthetic protein library could initially be sub-divided into a number of pools, each pool containing a proportion of the library. This would be achieved by dividing the initial mixture of genes. Each pool would then be screened as described above to identify a pool containing a protein of interest. The transcription mix for that pool would then be sub-divided again and the screening process repeated. This procedure would be repeated using progressively smaller pools of ribosome displayed proteins until a single clone was identified which encoded the protein of interest. Alternatively, following identification of a potentialdisease associated protein by 2D gel analysis, the protein would be purified from the gel according to standard protocols (Hager & Burgess, Anal. Biochem., 109, (1980), pp76) and the purified protein panned with a scFv library to identify an antibody(s) which recognises the protein. The antibody(s) would then be used to screen a synthetic protein library constructed from the cDNA of the diseased sample to identify the protein with its associated gene tag. As an alternative highly innovative method to identify the protein, each recombinant protein may be produced with an amino acid sequence tag originally encoded by the plasmid vector and subsequently incorporated into the protein, for example by incorporating a leader sequence into the cloned cDNAs derived from the vector or from a mixture of synthetic oligonucleotides used to copy the cDNA for subsequent cloning into the vector. The nucleotide sequence tag may be variable or randomised in the plasmid vector preparation, for example by producing the plasmid vector using a synthetic region encoded by a random oligonucleotide mixture (with appropriate ends which anneal to the vector) to place random a sequence tag at, for example, the 5 end of the mRNA Following production of the protein mixture by, for example, IVTT or ribosome display and separation of these proteins by 2D gel electrophoresis, individual proteins could then be analysed by probing with antibodies specific for the various permutations of sequences.

It will be obvious for the present invention that a prime application will be in the analysis of proteins, protein modifications and protein-protein interactions which relate to human disease or to the healthcare, individual or drug treatment status of humans. The invention incorporates the use of "clinical samples", such term referring to samples which may be tissue, blood or other which could be expected to be affected by the particular disease. The diseased samples refers to a sample which can be demonstrated to be affected by a disease, healthcare status or drug treatment status. The normal sample refers to a sample which is not affected by the disease and represents normal healthcare status, but may vary between individuals and may be relevant to the subsequent outcome of drug treatment. For comparative purposes in searching for disease associated proteins or protein modifications/interactions, the normal and diseased samples would ideally be matched to reduce population induced heterogeneity. This may be achieved by obtaining normal and diseased samples from a single patient (e.g. cancerous breast tissue and unaffected breast tissue) or alternatively by pooling diseased and normal samples from a number of different patients.

The generation of cDNA libraries from both normal and clinical samples is performed by standard techniques involving the isolation of mRNA followed by reverse transcription to generate cDNA (Sambrook et al., Molecular Cloning: a Laboratory manual 2nd Ed., Cold Spring Harbor Press, 1989) or alternatively may be achieved using commercially available kits e.g. PolyATract System (Promega, Southampton, UK). The cloning of the cDNAs into a vector suitable for generation of synthetic proteins such as in vitro display by ribosome display and the conditions for in vitro display of the proteins would be as previously described (for example in Hanes and Pluckthun, Proc. Natl. Acad. Sci. 94 (1997), p4937). The isolation of total protein from the samples would be achieved by standard methods as detailed Bollag & Edelstein (Protein Methods, Wiley-Leiss, 1991).

Ribosome Display—In the second embodiment of the present invention, there is provided a new in vitro method of ribosome display which maximises the expression of full-length polypeptides from a ribosome by selective arrest of MRNA translation at the 3' end of the mRNA such that the ribosome complex it is still linked to the full-length polypeptide. The invention is based on the discovery that proteins bound to specific sites in mRNA molecules will block the further translation of the mRNA allowing the stalling of a mRNA-ribosome complex with associated polypeptide. The invention also includes optional measures to prevent new translational starts just prior to polypeptide screening.

The method of the present invention involves firstly the creation of a library of DNA molecules, commonly within a plasmid vector, such DNA molecules encoding various polypeptides whereby the DNA encoding these polypeptides is transcribed into mRNA molecules. Commonly, the cloning vector for the DNA molecules includes an upstream promotor such as a promotor for T7 RNA polymerase. Thus, the pooled library of DNA molecules is transcribed, for example by the addition of T7 RNA polymerase and ribonucleotides, to produce a library of mRNA molecules. Thereafter, the library of RNA molecules is translated using a ribosome preparation such as an E. coli S-30 fraction (Chen H Z and Zubay G, Methods in Enzymology, vol 101 (1983) p674–690). Thereafter, the ribosome complexes, comprising linked polypeptide, ribosome and mRNA, are typically screened for binding to a ligand immobilised onto a solid phase and mRNA is released from the resultant immobilised complexes for reverse transcription and amplification by PCR in order to enrich for DNA molecules encoding polypeptides which bind to the target ligand. These DNA molecules can either be used directly for transcription or can be cloned in order to determine the sequences of DNA encoding polypeptides which bind to the target ligand. For the purpose of this embodiment of the invention, the mRNA encoded by the DNA molecules will be considered to include 3 segments comprising, from 5' to 3', a variable segment, a spacer segment and a termination segment with an optional anti-initiation segment 5' to the variable segment. The polypeptide shall mean the protein or peptide sequence translated from the variable segment of the mRNA to protein via a ribosome complex. The variable segment shall mean mRNA sequences encoding the full-length polypeptide. The spacer segment shall mean mRNA sequences encoding protein segments contiguous with the variable segments which allow the completed proteins to completely emerge from the ribosome and adopt optimal three dimensional structures whilst still attached to the encoding mRNA through the ribosome complex. The terminating segment shall mean mRNA sequences to which the binding moiety attaches either directly or indirectly or, alternatively, mRNA sequences encoding a polypeptide binding moiety, contiguous with or upstream from the spacer segment to which specific proteins attach in order to block translation. The binding moiety shall mean any molecule that can bind either to the mRNA on the ribosomal complex or any molecule that can bind to the translated polypeptide on the ribosomal complex resulting in arrest of translation. The binding moiety will usually bind directly to mRNA in a sequence specific manner or may be bound indirectly to the mRNA, for example after annealing of a synthetic DNA or RNA molecule to the mRNA and addition of the binding moiety via a ligand on these molecules. The optional anti-initiation segment will be adjacent to the translational initiation codon and will provide sequences for attachment usually of a different binding moiety. The anti-initiation segment will prevent new translational initiations just prior to screening of the translated polypeptides. The target ligand will be the molecule against which the library is screened for binding of specific proteins and subsequent recovery of associated mRNA.

The variable segment of the mRNA molecules comprises either full-length known polypeptide types such as single-chain antibodies (SCAs, comprising immunoglobulin variable regions derived from heavy and light chains and linked together to give a functional binding domain), or random or semi-random sequences. Chimaeric sequences created by random/semi-random association of known polypeptide types or regions may also be used. For known polypeptide types such as SCAs, specific segments of the genes may be randomised such as the CDRs in SCAs. Large collections of DNA molecules encoding known, random or semi-random sequences will be firstly produced and then cloned into the transcription vector. This transcription vector will provide other segments for inclusion in the subsequent mRNA molecules as detailed below. The vector will also usually provide a translation initiation codon and ribosome binding site for the mRNA. For longer polypeptide molecules encoded by the DNA, it will be necessary to reduce or eliminate the presence of stop codons in the mRNA which would terminate translation. It is a requirement of the invention herein that such stop codons, including stop codons natural to specific proteins, are eliminated in order to yield full-length polypeptides.

For DNA encoding known proteins such as single-chain antibodies, this will simply require elimination of the usual stop codon or, alternatively, the use of nonsense suppressing tRNAs in the translation reaction in order to insert specific amino acids at the position of the stop codons. For mixtures of random or semi-random DNA molecules produced by chemical synthesis, the frequency of stop codons occurring in any particular sequence can be reduced by manipulation of DNA base composition in the synthesis reaction and nonsense suppressing tRNAs could also be used in the translation reaction. The spacer segment of the mRNA molecules provides a polypeptide region downstream of the variable segment which spans the channel of the ribosome in order to permit the full-length polypeptide to fully emerge from the ribosome to allow for proper protein folding and unhindered access to the target ligand. Usually this segment will encode a region of over 50 amino acids and will encode a region which is unlikely to interfere with folding of the full-length polypeptide such as a complete domain from another protein or a glycine/alanine-rich linker such as (Gly4Ser)10. For some translated proteins, the spacer segment may comprise a contiguous portion from the protein itself where this portion is not required for correct folding of the variable segment or for binding to the target ligand.

The terminating segment provides a downstream mRNA sequence for direct or indirect attachment of a binding moiety which is designed to prevent translational termination following translation of the complete variable segment. A particularly favoured method for attachment of a binding mioety is indirectly using an intermediate synthetic oligonucleotide molecule which first anneals to the terminating segment. If such synthetic nucleotide is equipped with a specific binding site for the binding moiety, then the binding moiety can, in turn, bind to the annealed synthetic oligonucleotide and thereby attach to the downstream end of the mRNA to block translation. One example of this favoured method is to use an oligonucleotide which incorporates one or more biotinylated nucleotides such that streptavidin can subsequently bind thus providing a molecule which blocks translation. The use of molecules such as streptavidin also provides for simple possibilities for cross-linking the nascent protein to the mRNA molecule where the nascent protein could itself be biotinylated by virtue of incorporated biotinyl lysine (or another biotinylated amino acid) in the in vitro translation reaction mixture. Another example of this favoured method is to use an oligonucleotide which incorporates one or more nucleotides derivatised with a ligand such as fluorescein or dinitrophenol which can then be bound by a monoclonal antibody or fragment thereof This also makes feasible the use of bispecific molecules such as bispecific antibodies which might bind, on the one hand, to the mRNA via the synthetic oligonuleotide, and on the other hand also to the translated protein or polypeptide by virtue of an amino acid sequence on the translated protein or poypeptide. Other methods include providing the terminating segment with a sequence to which a specific protein binds directly without any intermediate annealing step. One example of such a binding moiety is the Iron Regulatory Protein (IRP). The terminating segment would provide a stem-loop structure which is stabilised by the addition of the IRP in conditions of low iron concentration, thus resulting in a steric block to the ribosome translation. Following this, selection of the nascent peptide can occur. The use of IRP to arrest the ribosome introduces a reversible block such that addition of iron may allow translation to resume and thus terminate. This would facilitate the release of the mRNA after selection of the polypeptide for subsequent transcription, sequencing or cDNA cloning. Further examples of mRNA binding moieties binding to sequences in the terminating segment include the HIV protein tat, which binds to a RNA stem-loop termed TAR (Dingwall et al., PNAS, vol 86 (1989) p6925–6929), La antigen which binds to a RNP motif (Chan E K L and Tan E M, Mol. Cell. Biol. vol 7 (1987) p2588–2591) and other proteins from RNA viruses which bind to specific RNA sequences either in single- or double-stranded RNA, the latter which can be created in mRNA via hairpin loops. The terminating segment alternatively could encode a site for attachment of a binding moiety which additionally binds to the synthesised polypeptide itself or to the ribosomal protein complex in order to further stabilise the binding moiety for prevention of translational termination. Optionally, the terminating segment will include one or more further regions of mRNA which increase the stability of mRNA against exonucleases such as the lpp (*E.coli* lipoprotein) and phage T3 terminators. It will be particularly clear to those skilled in the art that, for the major aspect of this embodiment of the invention, mRNAs could be produced with a variety of terminating segments to which a variety of binding moieties could bind either indirectly, through the initial annealing of a synthetic oligonucleotide or other molecule, or directly through the recognition and binding of a binding moiety directly to the mRNA molecule.

The optional anti-initiation segment adjacent is designed to prevent translational initiations late in the translation reaction which might not result in full-length polypeptides and might therefore provide polypeptides with incomplete folding which might provide non-specific binding to target ligands. The anti-initiation segment might encode, for example, a secretory leader sequence in the translated polypeptide to which can be bound the signal recognition protein (SRP). Once SRP has bound to the polypeptide, it causes the arrest of further translation by cross-linking of the polypeptide and the mRNA Translational arrest may also be achieved by using a combination of the SRP54 and SRP9/14 subunits of SRP (Siegel & Walter, Cell Biol., vol 100 (1985) 1913–1921) which bind to the nascent peptide and MRNA respectively. Another example of anti-initiation sequences is provided by certain eukaryotic transcription leaders such as that of the human cytomegalovirus gp48 gene which contains an upstream 22 codon which represses translation of the downstream cistron (Cao J and Geballe A P, Mol. Cell. Biol. vol 16 (1996) p7109–7114). Such leaders are thought to encode peptides which block ribosome progression to the downstream cistron. Further examples of anti-initiation sequences are sequences recognised by binding moieties such as for the terminating segment as above, these including sequences bound by IRP, tat, La antigen and other viral proteins.

The invention therefore provides compositions of DNA libraries encoding mRNA molecules with variable, spacer and terminating segments with an optional anti-initiation segment. Preferably, the invention provides a DNA vector encoding the spacer and terminating segments; the anti-initiation segment is optional. Commonly, the DNA vector will also provide the translation initiation codon and, for translations using prokaryotic ribosomes, a ribosome binding site including the Shine-Dalgarno sequence. For eukaryotic translation systems, the Kozak translation initiation sequenc SEQ ID NO: 1 with consensus GCCGCCAC-CATGG may also be included and, upstream from the translation initiation site, it may be desirable to include other known sequences to enhance translation such as enhancers or activator sequences including untranslated leader sequences from certain viruses such as tobacco mosaic virus. Commonly, the DNA vector will also provide a strong transcriptional promotor which will be used in conjunction with a RNA polymerase to produce a library of MRNA molecules corresponding to the DNA library. Such promotors will include those for T7 RNA polymerase, T3 RNA polymerase and SP6 RNA polymerase and, additionally, a promotor for the RNA dependant polymerase, Qb replicase, may also be encoded by the DNA. The DNA vector will also provide a strong transcriptional terminator, for example the terminator of *E. coli* lipoprotein or the early terminator of phage T3. In the method of the invention, DNA fragments containing the variable segments are cloned into the DNA vector whereby the DNA fragments have a minimum of or no stop codons. For libraries encoding known polypeptide types such as SCAs, the DNA fragments will be cloned unidirectionally using appropriate restriction sites. It will be apparent to those skilled in the art that a variety of replicable DNA vectors could be used in the method of the present invention including plasmid, bacteriophage, phagemid and viral vectors. It will also be clear that DNA amplification by methods such as PCR could be used as an alternative to replication of DNA in living cells. It will also be clear that the variable segments to create the DNA library could be provided from a number of sources including a vector library of DNA fragments, synthetic DNA or amplified DNA. In addition, the variable segments could be provided as a result of mutagenesis reactions using a fixed template, for example using error-prone PCR. It will also be clear that the variable segmeIRPnts could be composed of DNA directly from the genome of a living organism or from cDNA copies of mRNAs of that organism. For example, where the DNA library comprises single-chain antibody fragments, these fragments could be derived from mRNA encoding immunoglobulin variable regions and expressed by B cells within an organism. Alternatively, the fragments could be derived from genomic variable regions. In such manner, the invention will provide for the creation of single-chain antibody libraries from specific organisms such as man.

The invention also provides compositions of libraries of MRNA molecules with variable, spacer and terminating segments with an optional anti-initiation segment. Preferably, the invention provides a library of mRNA molecules encoding the spacer and terminating segments, with the anti-initiation sequence optional. The mRNA molecules will each include a translation initiation codon and, for translations using prokaryotic ribosomes, a ribosome binding site including the Shine-Dalgarno sequence. For translation using eukaryotic ribosomes, the MRNA may synthesised with a 5' capping nucleotide or this may be introduced enzymatically into the pre-synthesised mRNA Upstream from the translation initiation site, the consensus Kozak translation initiation sequence may also be included and other known sequences to enhance translation such as enhancers or activator sequences including untranslated leader sequences from certain viruses. Prior to or during the process of translation, one or more binding moieties will become associated with the terminating segment of the mRNA molecules thus stalling translation. Also, during the process of translation, one or more binding moieties may become associated with the optional anti-initiation segment within or encoded by the mRNA molecules thus preventing new translational initiations.

The invention also provides compositions of libraries of translated polypeptide molecules with variable and spacer segments with an optional anti-initiation leader sequence. These protein molecules will provide full-length variable segments as part of a longer polypeptide chain which is stalled within the ribosomes through the interaction of binding moieties with the mRNA At the 5' end of the polypeptide. The present invention relates toacts with the ribosome thus preventing additional translation on the mRNA molecule. Alternatively, the 5' end may become associated with a binding moiety indirectly such as via the annealing of a synthetic oligonucleotide to a complementary sequence at the 5' end and subsequent binding of a binding moiety to this oligonucleotide, such as via biotin molecules incorporated into the synthetic oligonucleotide.

Within the method of the present invention, it will be apparent to those skilled in the art that various measures could be used to optimise the stability of mRNA molecules especially from degradation by RNAses. For example, various inhibitors of RNAses such as Rnasin and vanadyl ribonucleoside complexes could be used in the transcription reactions.

Alternatively or additionally, various structures could be included in the mRNA molecules including 3' stem-loops such as those commonly provided by transcriptional terminators. It will also be apparent to those skilled in the art that transcription and translation reactions might either be performed separately or, especially with prokaryotic systems, combined into a coupled in vitro transcription/translation reaction. Preferably, the transcription and translation reactions will be performed separately in order to optimise the production of mRNA and polypeptides which will require different optimal reagents.

Within the method of the present invention, it will be apparent to those skilled in the art that various measures could be used to optimise the folding and stability of protein molecules especially from degradation by proteases. For correct protein folding, optimal oxidative protein folding conditions would be used in translation reactions with particular measures to optimise disulphide bond formation through, for example, use of molecular chaperones such as protein disulphide isomerase. For stability, the peptide tagging system of E. coli could be disabled by inhibition of ssr A RNA using methods such as that of Hanes and Pluckthun (ibid). Once the final polypeptide/ribosome/mRNA complexes are formed, it may be beneficial to stabilise these complexes using standard translational inhibitors such as chloramphenicol. Additional chemical, photochemical or enzymic cross4inking of the polypeptide chain and/or mRNA to the ribosome may also be beneficial. For example, the enzyme transglutaminase may be employed using a C-terminal glutamine placed on the nascent polypeptide chain to provide a substrate for cross-linking to a free amino group preferably provided at the 3 end of the RNA molecule using a complementary synthetic oligonucleotide. As an alternative example, chemically-modified amino acids (such as selenium amino acids) might be incorporated into the protein chain for subsequent reaction with chemically modified RNA nucleotides, such as thiolated nucleotides.

Once polypeptide/ribosome/mRNA complexes are formed, the mixture can then screened for binding to the target ligand in such a manner that successfully binding complexes can subsequently be recovered. This could be achieved by virtue of binding to a target ligand immobilised onto a solid phase such as a plastic or glass surface or the surface of a latex or magnetic bead. Other embodiments of this invention include binding to cells and tissues, and binding to other molecules in solution including protein molecules encoded by the same mRNA used to form the polypeptide/ribosome/mRNA complexes. This could also be achieved by virtue of the binding of the target ligand effecting another:reaction or series of reactions which subsequently provides the basis for separation of the complex, for example where binding to the target ligand on the surface of a cell causes a change in that cell such as the appearance of a surface antigen whereby the cell can be separated from other cells in the population along with the bound polypeptidelribosome/mRNA complex.

As an alternative, the polypeptide could be screened for a particular enzymic activity whereby the target ligand is, for example, an enzyme substrate which irreversibly binds to the enzyme or where the substrate is convened by the enzyme to a product which can combine with the polypeptide/ribosome/mRNA complex or can effect some other change such that the polypeptide/ribosome/mRNA complex including the enzymic activity can be separated from the total mixture of complexes.

In order to avoid non-specific binding to the target ligand, various blocking agents would be added to the polypeptide/ribosome/mRNA complexes for incubation with the target ligand, especially to avoid non-specific associations of the mRNA with the target. Whilst various standard blocking agents such as serum albumin or casein might be beneficial, a preferred method which specifically blocks non-specific mRNA binding is to form the cDNA prior to binding the polypeptide/ribosome/mRNA complexes using a synthetic oligonucleotide primer and reverse transcriptase. The use of this step also provides protection for the mRNA from enzymic degradation whilst, after binding to the target ligand, permitting subsequent enzymatic destruction of the mRNA using RNaseH which degrades mRNA in a mRNA:cDNA hybrid.

Once polypeptide/ribosome/mRNA complexes are separated by virtue of binding to a target ligand, the complexes can either be purified preparatively by standard methods or the RNA simply released using, for example, EDTA or simple heating prior to reverse transcription into cDNA. Alternatively, the mRNA could be copied into cDNA prior to binding of the polypeptide/ribosome/mRNA complexes and then destroyed with RNaseH as above. Amplification of the cDNA by methods such as PCR is then undertaken. The amplified DNA can then either be transcribed and translated again in order to further divide the library or can be cloned to produce a sublibrary. For molecular evolution strategies where polypeptides which bind to the target ligand are evolved by mutation, mutagenesis can either be effected at the stage of cDNA amplification using, for example, error-prone PCR or can be effected by subjecting the cloned sublibrary to mutagenesis, for example using mixed oligonucleotides to mutagenise specific regions of the polypeptide-encoding DNA segment. If required, the initial DNA library for transcription/translation or a sublibrary following screening can be subdivided into pools or individual clones for screening in order to reduce the complexity of the mixture of polypeptides subjected to screening. After finally identifying one or more polypeptides deriving from the DNA library, DNA encoding the specific polypeptides of interest can then be subcloned into expression vectors in order to produce high levels of the desired protein without, as required, the spacer segment or any other flanking segments.

It will be apparent to those skilled in the art that the present invention will have a variety of applications including the isolation of variants of known polypeptide types such as SCAs or totally novel proteins with biochemical or biological activities superior to those of existing proteins. Chimaeric proteins created as hybrids of regions from known polypeptides and regions of novel polypeptide sequence may also be produced. For multichain polypeptide types such as antibodies, functional or novel combinations of heavy and light chain variable regions may also be produced.

Biological Screening—In a third embodiment of the present invention, there is provided a new method to directly select a biological phenotype encoded by a DNA library and expressed via polypeptide display. The method provides a direct link between biological phenotype and genotype without the need for any prior knowledge of the binding phenotype of the displayed polypeptides. In one aspect of this embodiment of the invention, the stimulation (or inhibition) of a biological response by binding of displayed biologically active polypeptides results in alterations in the target living cell which provide the basis for separation of the altered cell. In turn, the gene or genes encoding the biologically active polypeptides-can then be recovered via recovery of the altered cell. In another preferred aspect of this embodiment, the stimulation (or inhibition) of a biological response by binding of displayed biologically active polypeptides results in the production (or cessation of production) of a molecule (herein termed the "modulator") from a target living cell which, in turn leads to the recovery of genes encoding the biologically active polypeptides. The invention provides for 2 broad methods for recovery of genes encoding the biologically active polypeptides as follows;

(1) "tagging"—in this method, the modulator produced by the target living cell binds to the complex including the displayed protein/polypeptide and thus tags this complex for subsequent isolation. For example, the target living cell may produce, as a result of the biologically active polypeptide, a protein or proteinaceous complex which binds to a ribosome complex displaying the biologically active polypeptide which includes the mRNA encoding it. The preferential binding of the modulator to the complex displaying the biologically active polypeptide would be as a result of the close proximity of this complex to the target living cell, for example at the surface of the target cell or within the target cell. Following production of the modulator by the target cell, the tagged complex including the displayed polypeptide can then be isolated, for example by using an antibody which binds to the modulator to separate the complex displaying the biologically active polypeptide from other complexes devoid of biologically active polypeptides. Following separation of these complexes, the genotype encoding the biologically active polypeptide can be determined. In addition to its application in ribosome display, the tagging method could also be used with polypeptide display methods employing live microorganisms; for example, the modulator could be used to tag bacteriophage for subsequent isolation of tagged phage and recovery of genes encoding biologically active polypeptides.

(2) "complementation"—in this method, the modulator produced by the target living cell is necessary for the subsequent viability of a living microorganism. For example, the target living cell may produce, as a result of the biologically active polypeptide, a modulator which is required to restore the infectivity of a defective bacteriophage displaying the biologically active polypeptide and thereby containing the gene encoding it. Upon restoration of infectivity, the bacteriophage can then propagate through the infected host in order to amplify the gene encoding the biologically active polypeptide. The preferential binding of the modulator to the bacteriophage displaying the biologically active polypeptide would be as a result of the close proximity of this complex to the target living cell, for example at the surface of the target cell or within the target cell. Following amplification of the bacteriophage, the genotype encoding the biologically active polypeptide can be determined. In addition to its application in bacteriophage display, the complementation method could also be used with polypeptide display methods employing live bacteria; for example, the modulator could be an antibiotic, a drug resistance enzymelfactor or an essential nutrient which, under appropriate selection conditions, allow for selective growth of bacteria in close proximity to the target living cell and thus amplification of the genotype encoding biologically active polypeptides.

It will be apparent to those skilled in the art that the modulator released from target living cells for the tagging or complementation methods could also provide the tagging or complementation moieties indirectly, for example by release of these from a liposome or other molecular compartment via lysis of liposomes induced where the modulator is, for example, a phospholipase or, for certain lipopolysaccharide-based liposomes, a galactosidase. Amongst the possible tagging or complementing moieties released from liposomes or other molecular compartments could be nucleic acids or infectious microorganisms. Released nucleic acids could include synthetic oligonucleotides which can tag, by annealing, the mRNA or rRNA components of ribosome complexes including the displayed biologically active polypeptide. Released infectious microorganisms could include bacteriophage which could thus infect the bacterial cell displaying the biologically active polypeptide and provide one or more genes which lead to the subsequent viability of that cell and thus amplification of the genotype. The released modulator could also be an enzyme .which effects a conversion of a substrate to a product which acts as the tagging or complementation moiety. It will also be apparent to those skilled in the art that the modulator could be constitutively released from target living cells where such release could be blocked by the biologically active polypeptide. It will also be obvious that other changes in a target living cell as a result of binding by a biologically active polypeptide could result in either tagging or complementation; for example, a biological change in a target living cell might lead to fusion of that cell with liposomes containing modulators which are thus released for interaction with the complex or microorganism containing the biologically active polypeptide.

In the primary method for implementing this embodiment of the present invention, a library of plasmids containing different genes are transcribed and translated into polypeptide molecules which are then tested for biological effect on mammalian cells. Specifically, the plasmid library could comprise a library of genes cloned downstream of a promotor for RNA polymerase to produce mRNA transcripts which are then translated in vitro. The translated polypeptide mixture with it's RNA still associated is then administered to cells and changes in the cellular phenotype are measured. Cells with the desired changed phenotype are then isolated and subjected to PCR using primers specific for the mRNA molecules still associated with the ribosome/polypeptide complex. In this manner, genes encoding polypeptides which induce the desired cellular phenotypic effect are amplified and can be sequenced, recloned into expression vectors or recloned into transcription vectors for subsequent re-testing of the proteins encoded by the genes. Through the use of mutagenesis strategies such as through use of error-prone PCR, proteins can thus be evolved through successive rounds of testing for induction of the required phenotype in order to generate polypeptides with the maximal biological activity.

As an alternative to plasmid vectors which are transcribed and mRNA translated, other methods may be used within the method of the present invention to produce polypeptides linked to a determinable genotype; such methods include bacteriophage vectors for display of proteins on the surface of bacteriophage particles and plasmid vectors which encode polypeptides fused to DNA binding polypeptides which cause the polypeptide to be tested to bind to the DNA encoding this polypeptide.

Having produced polypeptides linked to a determinable genotype, the present invention provides for a range of methods to induce a biological activity on target living cells whereby the genotype of the biological activity can be determined. One simple method is to detect biological activity by the appearance or disappearance of a cell surface marker which can then be used as the basis for separation of biologically active cells from inactive cells; commonly, this would be achieved using an antibody which binds to the cell surface marker and then using a method to separate antibody-bound from non-bound cells. Such a method would be via binding of magnetic beads to the antibody (e.g. using a bead-associated anti-immunoglobulin) or via fluorescence-activated cell sorting (FACS) whereby the antibody (or a second antibody) is fluorescently labelled. Having isolated cells with the required biological activity, the corresponding genotype can then be determined either PCR-mediated amplification of nucleic acid associated with the test polypeptide or by propagation of the bacteriophage bound to the separated cells.

Another method of linking a biological activity to a genotype is to engineer target cells to produce (or cease to produce) one or more tagging moieties which bind directly to the complex linking the test polypeptide to it's genotype. For example, cells might be engineered to produce a RNA binding polypeptide (such as HIV tat protein) which binds to the mRNA associated with a mRNA/ribosome/polypeptide complex. An example of such a promotor is the IL-2 promotor which is activated as a result, for example, of stimulation of the T cell receptor. This RNA binding polypeptide might be linked to a promotor which is activated as part of the biological effect or might be produced as a fusion polypeptide associated with another polypeptide which is activated as part of the biological effect. Following cell lysis or other release of the binding of test polypeptides to biologically active cells, the mRNA could then be isolated using, for example, an antibody which binds to the tagging moiety. Cells might also be engineered to produce a bacteriophage polypeptide which could complement other polypeptides in a disabled phage thus rendering the phage infective.

In cases where biological activity is accompanied by the appearance or disappearance of a cell surface marker, another adaption of the present invention is to link this surface marker to the release or generation of a tagging or complementation moiety.

This can be achieved, for example, by the use of an antibody-enzyme conjugates which bind to the cell surface marker and subsequently catalyse the release of a tagging or complementation moiety, for example by the enzymatic lysis of liposomes by phospholipase C (or beta-galactosidase for certain lipopolysaccharide containing liposomes) to release a variety of tagging or complementation moieties, or for example by the enzymatic conversion by horseradish peroxidase of biotinyl-tyramide to generate reactive biotin moieties.

It will be understood by those skilled in the art that, as an alternative to a surface antigen, an internally produced moiety could be used as the basis for selection whereby, following stimulation (or inhibition) of a biological response, cells are permeabilised and this moiety is either accessed by a binding protein such as an antibody or used for an enzymatic conversion in such a way that a tagging or complementation moiety is ultimately generated which can then combine to the polypeptide display complex.

Ligand-Directed Screening—this embodiment of the present invention provides a method of using a ligand which binds to a receptor on the surface of a cell ot tissue in order to label molecules in the vicinity of the surface receptor. In particular, the invention uses the ligand to guide another molecule attached to the ligand onto the cell surface where this other molecule can then effect a labelling reaction. In particular, this embodiment provides for the labelling of displayed proteins which are pre-bound to the cell/tissue in the vicinity of the ligand such that the corresponding genes encoding the displayed proteins can be isolated. In the description which follows the term receptor refers to a proteinaceous moiety to which a ligand can bind. The term ligand refers to a molecule, usually proteinaceous, which bind to the receptor. The term binding proteins refers to proteins encoded by a DNA library. Protein-complexes refers to the complex of binding protein and nucleic acid whereby, upon binding to a target molecule, individual genes encoding the binding proteins can be recovered such that the binding protein can be regenerated. The label refers to a molecule which is released by the labelling moiety and which c an combine or react with protein-complexes via the label-receptor. The labelling moiety refers to the carrier or source of the label referring commonly to an enzyme which can subsequently catalyse the release of the label. Th e label-receptor refers to the site o n the protein-complex where the label binds.

A preferred feature of this embodiment of the present invention is the use of liposomes as the labelling moiety to provide the label which labels the protein-complexes binding immediately adjacent to the ligand whereby the ligand is or can become associated wit h liposomes which are made to release their encapsulated contents in the vicinity of the ligand. This provides a great versatility in the use of different labels in the method of the present invention. Other labelling systems such as the enzyme activation system described in U.S. Pat. No. 5,196,306 can also be used within the method of the present invention.

A preferred feature of this embodiment is the use of protein-complexes each comprising a mRNA molecule, one or more ribosomes and one or more translated proteins. In such a complex, the protein(s) act as the binding protein(s) whereby, upon successful binding, the protein-complex can be recovered and the mRNA replicated usually by conversion to cDNA, commonly using PCR, and subsequent transcription (by virtue of a transcriptional promotor introduced by synthetic DNA) or cloning into replicable vectors. Another preferred feature of this embodiment is a replicable nucleic acid gene library from which can be derived protein-complexes. Commonly, genes from this library will encode antibody variable regions (commonly in the form of single-chain Fv's, or scfvs) although libraries of other proteins can also be used especially libraries encoding conserved internal protein frameworks with variations in the external amino acids and protein structures/shapes. It is a requirement of the present embodiment that the protein-complex can be labelled by the label in such a way that labelled protein-complexes can be preferentially isolated away from unlabelled protein-complexes.

Preferably, in this embodiment of the present invention, there is provided a proteinaceous ligand which binds to a previously uncharacterised receptor on the surface of a cell or tissue section. The ligand is either combined directly before binding with bacterial phospholipase C (PLC) by chemical conjugation or combined indirectly usually after binding with, for example, an anti-ligand antibody itself conjugated to PLC. Following binding of the ligand to the cell, the protein-complexes derived from the DNA library are added to the cell/tissue to allow for the protein components to bind to the cell/tissue and excess non-binders are removed by washing. This effectively leaves a cell or tissue with a multitude of surface bound protein-complexes including some complexes in close vicinity to the bound ligand including some actually bound to the uncharacterised receptor for the ligand. In the next step, a preparation of liposomes are added which encapsulate a label. Upon contact of the liposomes with the cell or tissue with surface bound protein-complexes, the only lysis of the liposomes will occur through contact with PLC which hydrolyses lipid headgroups to destabilise the liposome at the point of PLC contact. This leads to the leakage of the label from the liposome.

Whilst the label can diffuse away from the site of PLC contact, it is a principle of the present invention that a suitable label can efficiently react with a suitable label-receptor only in the vicinity of the PLC. Such a label is streptavidin which can bind tightly to biotin molecules associated with the protein-complex, usually on the mRNA component by virtue of an annealed synthetic oligonucleotide. An alternative label is the HIV tat protein or a peptide fragment thereof which can bind to a hairpin-loop (TAR) on suitable mRNA molecules. Having reacted with the adjacent protein-complexes, excess liposomes and label are washed away from the cell/tissue and the labelled protein-complexes are recovered. Recovery can be effected usually using an immobilised label or derivative of the label (e.g. biotin) or an antibody which specifically binds to the label (e.g. anti-biotin, anti-tat). Various measures can be employed to remove the labelled protein-complexes from the cell/tissue surface without dissociating the protein-complexes although the genetic component of the protein-complexes can also be removed preferentially by, for example, addition of EDTA to dissociate mRNA/ribosome/protein complexes. The recovered labelled protein-complexes or genetic component of the protein-complexes can then be subjected to nucleic acid amplification in order to expand the numbers of nucleic acid molecules and to facilitate subsequent re-cloning of DNA into a suitable replicable vector or, where transcription/translation is used, to permit subsequent transcription by virtue of a promotor introduced via synthetic DNA used for gene amplification. Thus, genes encoding one or more binding proteins which bind to the cell/tissue adjacent to the ligand can therefore be isolated to provide an abundant source of binding protein to facilitate in the molecular isolation of the receptor and also possibly in the molecular isolation of molecules in the vicinity of the receptor which may include molecules which are activated by the receptor in the transmission of a signal to the interior of the cell.

In addition to facilitating the molecular isolation of the receptor, the binding proteins isolated by the method of this embodiment of the invention can themselves be used effectively as ligands for a subsequent round of cell/tissue binding whereby the original binding proteins are themselves conjugated or attached to one or more PLC molecules. Following binding of these binding protein-PLC conjugates to the cell/tissue at the receptor site, a library of gene-derived protein-complexes are then added to bind to the cell/tissue. From a suitable library, this would provide binding proteins which bind both to the natural ligand binding site of the receptor itself and also to other proteins in the vicinity of the receptor. Upon liposome addition and lysis upon contact with PLC molecules, new protein-complexes would be labelled with labels such as streptavidin or tat allowing their subsequent isolation or enrichment. By retrieval of the genes encoding the binding proteins in these labelled binding protein-complexes, a number of additional tools for receptor and adjacent molecule isolation may be provided. However, in some cases more desirable, one or more of the new labelled protein-complexes might bind to the natural ligand binding site and therefore might provide new binding proteins which might block binding of the natural ligand or which might substitute for the natural ligand in activating the receptor or which might induce an antagonistic response at the receptor through receptor-induced down regulation of activities which are normally up-regulated by the natural ligand. In some cases, individual binding proteins might provide candidate pharmaceutical molecules.

It will be recognised by those skilled in the art that the method of this embodiment of the invention will usually be conducted using a DNA library comprising a collection of genes encoding different protein types, some of which might bind to the target receptor.

It will be recognised by those skilled in the art that the ligand molecule can be any molecule, proteinaceous or non-proteinaceous in nature, to which can be attached either directly or indirectly, a labelling moiety capable of releasing the label to attach to the protein-complex.

It will be recognised by those skilled in the art that the binding protein could be based upon several molecular types. Whilst the protein type will commonly be antibodies encoded by antibody variable regions (commonly in the form of single-chain Fv's, or scFvs), other proteins can also be used especially those with conserved internal protein frameworks whereby variations in the external amino acids and protein structures/shapes will generate a library of different protein molecules. Some of the shapes adopted by such non-antibody protein molecules may be more compatible to binding to the target receptor than antibodies themselves which are suitable for binding to other protein molecules with relatively flat binding faces but less suitable to binding to protein molecules with complex shapes such as concave shapes to accommodate large proteinaceous ligands.

it will be recognised by those skilled in the art that the protein-complex could be one of several types whereby the binding protein is linked either directly or indirectly to the nucleic acid sequence encoding it. In the preferred embodiment, the protein-complex is a complex of mRNA/ribosome/protein which is formed by translation of mRNA under conditions designed to optimise yield of complexes in preference to translated proteins which have terminated and become free from association with ribosomes and therefore mRNA. In other embodiments, the protein-complex will comprise bacteriophage particles derived from gene libraries which display the binding protein on the phage surface.

Alternatively, the protein-complex will comprise bacterial particles which display the binding protein derived from gene library on the bacterial surface. Other embodiments will include lad fusion proteins comprising fusions of lacI and the binding protein whereby lad binds to the lac operator on a plasmid encoding the binding protein and other viral protein display systems including baculovirus and retroviruses.

It will be recognised by those skilled in the art that the label can be one of many molecules which can bind to other proteinaceous or nucleic acid molecules in a protein-complex in the vicinity of the labelling moiety which releases the label. It will also be recognised that the corresponding label receptor can be one of several molecules matched to the label. Suitable labels (and label receptors) will include streptavidin (biotin), tat (TAR hairpin loop on mRNA), signal recognition particle (SRP) (eukaryotic leader sequence on protein), antibody (antigen), RNA binding molecules (mRNA), specific protein binding molecules (binding sequence on protein), F pilus (bacteriophage F receptor) and nickel (histidine "tag" on protein).

It will be recognised by those skilled in the art that the labelling moiety will commonly be an enzyme which causes the release of the label. Such labelling moieties will include PLC (for liposome, red blood cell, or other cell lysis), horseradish peroxidase (for biotinyl tyramide) and bacterial enzyme beta-galactosidase (for lysis of glycoliposomes). It will also be recognised that, where the labelling moiety is a porin or membrane molecular channel, this may also cause the release of the label directly.

It will be recognised by those skilled in the art that other liposome lytic mechanisms could be used within the context of the present invention as an alternative to enzyme lysis. For example, it may be possible to attach whole liposomes to ligands either directly, for example by encapsulating the ligand with a lipid tail into the liposome membrane in such manner as to still permit ligand binding to a receptor, or indirectly, for example by using liposomes impregnated with surface antibodies or other binding proteins which target the liposome to the ligand. Under such circumstances, liposome lysis could be simple achieved by detergent lysis or heat or any other conventional ways of achieving liposome lysis.

It will be recognised by those skilled in the art that the method of the present invention could be used to directly label receptors and other molecules in the vicinity of receptors rather than to label protein-complexes. For example, using a PLC-conjugated ligand and liposomes containing streptavidin, the whole cell/tissue could be chemically biotinylated using, for example, biotin-NHS ester and then the PLC-ligand and subsequent liposome lysis would deposit streptavidin molecules specifically in the vicinity of the ligand including on the receptor which would therefore become labelled with streptavidin providing a basis for molecular separation using, for example, using immobilised biotin.

Protein-Protein Interactions—This embodiment of the present invention provides methods for isolating genes encoding displayed proteins or polypeptides which bind to a ligand by providing molecular tags on both protein/polypeptide and ligand as the basis for isolating the gene. The method particularly includes isolation of genes where the ligand is itself a displayed protein/polypeptide. This embodiment of the invention is based upon the binding of a polypeptide to a ligand (or other polypeptide) whereby molecular tags on the polypeptide and ligand can be used as the basis for molecular separation of the bound polypeptide-ligand from unbound polypeptide and ligand whereby the polypeptide is still associated with it's gene (or gene transcript). For selection of a polypeptide which binds to a ligand, a particularly favourable method is to provide molecular tags on both the polypeptide and it's ligand whereby methods are then applied for isolation of complexes containing both molecular tags. For example, using the technique of ribosome display, the mRNA may be tagged with a RNA binding protein (such as HIV tat protein) whilst the ligand (if a polypeptide) may be tagged with a polyhistidine tail such that consecutive passage of a library of mRNA-ribosome-polypeptide complexes over affinity matrices comprising anti-tag antibodies and nickel would select for binding polypeptides with associated mRNA which can then provide the gene sequence encoding for binding polypeptides. Alternatively, using ribosome display, only the polypeptide may be tagged, for example with a polyhistidine tail, passed over affinity matrices such as nickel chelate and any associated RNA may be accessed simply by converting into cDNA copies by PCR For selection of 2 or more binding polypeptides, a particularly favourable method is to use the technique of ribosome display using di(or poly)cistronic mRNAs for generation of candidate binding polypeptides derived from one or more DNA libraries. If the cistron for one of the polypeptides is constructed such that the translated polypeptide is dissociated from mRNA after translation and the cistron for the other polypeptide is constructed such that the translated polypeptide remains associated with mRNA after translation, then the translational juxtaposition of the 2-polypeptides is such that association, if applicable, is facilitated by this juxtaposition thus providing a molecular basis for separation of the complexes including the binding polypeptide(s) and mRNA, the latter which can then be used for the identity of genes encoding the binding polypeptide (s).

Another aspect of this embodiment of the present invention is based upon the binding of 2 polypeptides, one or both of which are associated with the corresponding gene, which are fused (or associated) with other polypeptide chains which, when juxtaposed, will generate a selectable property which then allows isolation of live microorganisms encoding the gene(s) for the binding polypeptides(s). Of particular interest within this embodiment is the generation of enzyme activities by the association of 2 polypeptides. Such generated enzyme activities can be used in a variety of ways for selection. These include enzyme activities which generate molecular tags which attach to complexes of successfully paired polypeptides and associated genes (or mRNA). For polypeptide display on microorganisms, these also include enzyme activities which generate (or release) molecules in the vicinity of the microorganisms which leads to the selection of microorganisms displaying a polypeptide derived from a DNA library which binds to a ligand. Also of interest within this embodiment is the generation of binding protein activities by the association of 2 polypeptides whereby the binding protein indirectly generates a selectable property which can be used as a basis for identifying the gene encoding the binding protein(s). For example, the binding protein could be a DNA binding protein such as a transcriptional activator which activates a gene which provides a selection advantage to the microorganism such as a antibiotic resistance protein or a nutrient generating protein.

For application of the present invention to binding polypeptides displayed on microorganisms, the invention provides for methods where the ligand (or second polypeptide) is added externally to the microorganism or methods where the ligand is synthesised internally within the microorganism, in both cases where the association of the polypeptide and ligand can generate a new molecule (or molecules) which provides a basis for selection or separation of the microorganism displaying the binding polypeptide. The invention can be based upon the complementation of an enzyme activity through the combination of 2 (or more) subunits of an enzyme which, when associated together, reform the enzyme activity. Reformation of the enzyme activity will then either provide for the positive or negative selection of the microorganism providing the enzyme activity. In one example of this embodiment of the invention, there is provided a DNA library encoding variant polypeptides which can be expressed in a microorganism or a cell whereby the genes encoding the binding polypeptides are fused to a portion of the gene encoding an enzymatically inactive fragment of an enzyme whereby this portion of enzyme can complement another portion of the enzyme to reconstitute enzyme activity. Suitable enzymes include *E. coli* beta-galactosidase and C. perfringens phospholipase C. The other portion of the enzyme is either provided in the microorganism culture medium for selection in vitro or provided by expression of a gene encoding this portion within the same microorganism for selection in vivo. Enzymes such as *E. coli* beta-galactosidase and C. perfringens phospholipase C have the property that inactive subunits of the enzyme can self-associate in solution to reconstitute enzyme activity and thus the invention provides for a situation whereby the binding polypeptide, fused to the gene encoding an inactive enzyme fragment, can bind to its ligand and either promote (where the ligand is fused to the other inactive subunit) or prevent (where the polypeptide-ligand binding, through steric hindrance, prevents the reconstitution of enzyme activity by the inactive enzyme subunit. The restoration or abolition of enzyme activity may have a beneficial or deleterious effect on the microorganism expressing the polypeptide/enzyme subunit gene fusion. This will either be due to the direct enzymatic action of the reconstituted enzyme, for example in causing the conversion of a non-toxic substrate to a toxic product, or indirect enzymatic action of the reconstituted enzyme, for example in causing the lysis of external liposomes containing a toxic agent or an essential nutrient/factor for growth/propagation of the microorganism.

Another aspect of this embodiment of the invention is based upon the binding of a polypeptide with a non-protein or defined protein moiety, whereby molecular tags on the polypeptide or the non-protein or defined protein moiety can be used as the basis for isolation of interacting polypeptide with non-protein or defined protein moieties from the unbound polypeptide and non-protein or defined protein moiety whereby the polypeptide is still associated with its gene (or gene transcript). The non-protein moiety may be defined as a molecule which is composed, in the main, of non-amino acids constituents such as nucleic acids (DNA or RNA) or chemicals (synthetic or natural). The defined protein moiety will be a protein the identity of which is known, for example, a preparation of total serum immunoglobulin whereby the serum immunoglobulin might interact with certain of the polypeptides. Association of the polypeptide with its gene transcript would be achieved using the technique of ribosome display where the polypeptide is part of a nascent protein which remains attached to the ribosome/mRNA complex, where the mRNA itself may be tagged with a RNA binding protein (such as HIV tat protein) oligonucleotide conjugated (or linked to) a non-protein or defined protein moiety, or where the mRNA may be tagged with a hybridising synthetic oligonucleotide conjugated (or linked to) a non-protein or defined protein moiety. Juxtaposition of the protein and non-protein or defined protein moiety can be achieved by attaching the non-protein moiety to a synthetic oligonucleotide which hybridises to the mRNA molecule. The non-protein or defined protein moiety may alternatively be tagged with, for example, a polyhistidine tail whilst the polypeptide moiety is linked to the mRNA as previously described such that consecutive passages of the library of mRNA-ribosome-polypeptide and non-protein or defined protein moiety complexes over affinity matrices comprising anti-tag antibodies and nickel would select for the bound polypeptide with its associated mRNA. For example the non-protein moiety could be DNA and the bound polypeptide a DNA-binding protein or in another example the defined protein moiety may be a lymphokine and the bound polypeptide a lymphokine receptor or region thereof.

Attachment of the non-protein or defined protein moiety to a hybridising oligonucleotide or mRNA binding protein could be achieved by any of the conventional ways of cross-linking polypeptides, such as those generally described in OSullivan et al., (Anal. Biochem 100, (1979), 108). Such cross-linking may be facilitated by the introduction of specific amino acids into the defined protein or the mRNA binding protein, especially free cysteine residues or free lysine residues. Alternatively attachment of the defined protein moiety may be achieved by the incorporation of biotin into both the hybridising oligonucleotide or mRNA binding protein and the non-protein or defined protein moiety (as described by Langer et al., PNAS 78, (1981), 6633) followed by the addition of avidin to cross-link the oligonucleotide or mRNA binding protein to the non-protein or defined protein moiety.

Another aspect of this embodiment of the present invention provides for the screening for agonists and antagonists of defined biochemical pathways whereby the individual proteins comprising the components of the pathway would-be sequentially expressed as full length polypeptides which remain attached to the polycistronic mRNA via a stalled ribosome. For example, using the technique of ribosome display, the proteins comprising a biological pathway could be sequentially cloned into an appropriate vector and displayed. Interaction between the polypeptides facilitated by close physical proximity will result in a detectable change in the final polypeptide in the pathway. For example the sequential association of the polypeptides will result in a phosphorylation cascade which causes a terminal phosphorylation or other event such as a conformational change. A particularly favourable method for the detection of the phosphorylation or conformation of the final polypeptide in both activated and non-activated states would be using antibodies. For selection of antagonists of the pathway, a particularly favourable method is to use the technique of ribosome display using polycistronic mRNA for the display of proteins in a biochemical pathway, sequentially juxtaposed. The displayed proteins are then screened with candidate molecules, whereby the candidate molecules may for example be ribosome displayed polypeptides derived from one or more DNA libraries, and inhibition of the activity of the pathway proteins assayed.

The following examples are provided to illustrate the invention and should not be considered as limiting the scope of the invention.

EXAMPLE 1

Generation of Synthetic Protein Libraries and Modification by Tissue

The starting point was a cDNA library preparation from "marathon-ready" human colon cDNAs obtained from Clontech UK Ltd (Basingstoke, UK). The library was amplified by PCR using primers AP1 (SEQ ID NOS.: 62 and 63) [5' ccatcctaatacgactcactatagggc] and AP3 [5'ttctagaattcagcggccgc(t)$_{30}$nn] using the Advantage cDNA PCR kit and conditions recommended by the supplier (Clontech). The resultant PCR product was cloned using a T/A cloning strategy into SmaI linearised pUC19 prepared according to Marchuck et al (Marchuck D. et al 1991, Nucl. Acids Res. 19: 1154). Alternatively, a human colon cDNA library constructed from human colon mRNA isolated directly from tissue using standard methods described in *Molecular Cloning, A Laboratory Manual* eds. Sambrook J, Fritsch E F, Maniatis T. Cold Spring Harbor Laboratory Press 1989, New York, USA. The mRNA converted to cDNAs using the RNAse H method (described in *Molecular Cloning* ibid) and recloned into the SmaI site of pGEMT7/SP6 plasmid (Promega, Southampton, UK) providing a promoter for T7 RNA polymerase. Long synthetic oligonucleotides and PCR were applied to provide an upstream bacterial ribosome binding site, a downstream spacer derived from the M13 phage gene III and a 3' transcriptional terminator region from the *E. coli* lpp terminator as described in Hanes and Pluckthun, *Proc. Natl. Acad. Sci.* 94 (1997), p4937.

In vitro transcription of the pT7 plasmids was performed using a RiboMAX™ kit (Promega, Southampton, UK)

according to the manufacturer's instructions. The resultant mRNA was purified according to the manufacturer's protocol. In vitro translation was performed using *E. coli* S30 Extract System with the inclusion of 35S methionine (Promega, Southampton, UK) according to the manufacturer's instructions. The ribosomes were dissociated from the proteins by treatment with EDTA as described by Hanes & Pluckthun (ibid) and the ribosomes removed by centrifugation (100,000 g for 30 min).

Crude protein extracts were prepared from a normal colon and a colorectal carcinoma sample by disruption of the tissue in ice cold RIPA buffer (RIPA buffer=50 mM Tris-HCL, pH7.4, 1% (v/v) NP40, 0.25% sodium deoxycholate, 150 mM NaCl, 1 mM EGTA, 1 mM PMSF, 1 mM $Na_3VO4$, 1 mM NaF and 1 ug/ml each of aprotinin, leupeptin and peptstatin). In some experiments, extracts competent for phosphatase activity were also produced; in this case lysates were produced using RIPA buffer without 1 mM $Na_3VO_4$. Tissue samples were thawed on ice and disrupted using a sterile disposable tissue grinder ("pellet pestle" Anachem Ltd, Luton, UK). Homogenisation was conducted using 2 volumes of ice cold RIPA buffer to 1 volume of tissue. The lysate was incubated with gentle shaking on ice for 15 minutes then cleared of insoluble material by centrifugation at 13,000×g at 4° C. for 10 minutes. The supernatant was removed and assayed for protein concentration using the bicinhoninic acid method and protocols provided by the supplier (Pierce, Chester UK, cat#23225). The lysate was divided into multiple aliquots, snap-frozen on dry ice and stored in liquid nitrogen.

Normal colon and colorectal tumour lysates were reacted with the in vitro translated proteins by incubation of thawed lysate for 30 minutes at 37° C. in the presence of 1 mg/ml vanadyl ribonucleoside complexes and 10 units Rnasin. The protein mixture was then solubilised according to the protocol of Cash et al., (*Electrophoresis* 18 (1997), p2580). The soluble proteins were then analysed by 2D PAGE (Cash et al. ibid) and the proteins detected by autoradiography(Patton et al., *BioTechniques* 8 (1990), p518). Images of the gels were captured using a video camera connected to an image analysis system and then transferred to Phoretix-2D for further analysis. Analysis was performed using Phoretix-2D systems according to the manufacturer's instructions.

Out of a total of 2622 protein spots detected from the in vitro translated protein mixture, 12 spots demonstrated migration differences when treatments with normal and colorectal cancer extracts were compared.

EXAMPLE 2

Phosphorylation of Synthetic Proteins

Recombinant purified rat ERK-2 containing a polyhistidine tag fused to the amino terminus of the protein was purchased from Stratagene, La Jolla, USA (cat #20612). This product is the non-activated form of the protein and contains no phosphorylated residues. 0.5 ug non-activated ERK-2 was reacted with a 5 μl (containing 2 mg/ml total protein) of A431 cell lysate (Upstate Biotechnologies, Lake Placid, N.Y., USA cat #12-110) or alternatively produced in-house from cells grown in tissue culture. The procedure of reacting a cellular or tissue lysate with a target protein is referred to as the Conditioning Reaction.

Cell lysates were produced by suspending approximately $5×10^6$ sub-confluent cells in 500 μl of ice cold RIPA buffer. Cells had been previously washed of medium using ice cold PBS and were incubated with gentle shaking on ice for 15 minutes in RIPA buffer. The lysate was cleared of insoluble material by centrifugation at 13,000×g at 4° C. for 10 minutes. The supernatant was removed and assayed for protein concentration using the bicinhoninic acid method and protocols provided by the supplier (Pierce, Chester UK, cat#23225). The lysate was divided into multiple aliquots, snap-frozen on dry ice and stored in liquid nitrogen before use in the conditioning reaction Lysates from tissue samples and other cell types were processed in the sane way.

The conditioning reaction was carried out at 37° C. for 15 minutes and then placed on ice. The reaction was divided equally (by volume) into two tubes for detection of phosphorylated ERK-2 using either magnetic sorting (tube 1) or binding to microtitre plate wells (tube 2) in both cases using anti-histidine antibodies as capture reagent.

In tube 1, ERK-2 was captured using magnetic beads (Dynal, Wirral UK, cat#110.11) pre-coated with an anti-histidine antibody (Sigma, Poole UK, cat#H1029) using coating conditions recommended by the supplier. The capture reaction was carried out at 4° C. 1 hour with constant gentle mixing throughout to maintain the beads in suspension. Following capture, the beads were collected using a magnetic particle concentrator and washed extensively in PBS. Beads were resuspended in a final volume of 40 μl and 10 μl aliquots were taken into microtitre plate wells and individually reacted with dilutions of either anti-phosphorylated ERK antibody (Upstate Biotechnologies, cat#05481), anti-phosphotyrosine-HRP conjugate monoclonal cocktail (Zymed, Cambridge UK, #136620), anti-phosphoserine/phosphothreoinine/phosphotyrosine polyconal preparation (Zymed, cat#90-0200) or a negative control antibody-HRP conjugate specific for human immunoglobulin light chains (The Binding Site, Birmingham UK, cat #APO015). Antibodies were incubated for 1 hour at 4° C. before detection with respective secondary reagents/chromogenic substrates. Plates were read at 450 nm.

In tube 2, ERK-2 was captured using microtitre plate wells which had been coated overnight with an anti-histidine antibody (Sigma, Poole UK, cat#H1029), and pre-blocked by 40 minute incubation with a solution PBS/5% (w/v) BSA at room temperature. The conditioning reaction was diluted to a total volume of 100 ul using PBS and added to the microtitre plate. The capture reaction was for 1 hour at room temperature. Phosphorylated ERK-2 was detected in direct ELISA format using the panel of antibodies including a negative control reagent as given above.

Using both detection methods above, the presence of phosphorylated ERK-2 was unequivocally demonstrated following incubation with lysates from A431 cells.

EXAMPLE 3

Method for Preparing In Vitro Translated cDNA Clones for Arraying onto Streptavidin Coated Plates.

A human whole foetal brain cDNA library was obtained from Stratagene Cloning Systems (La Jolla, USA). The library was supplied cloned unidirectionally into the lambda vector Uni-ZAP XR with an average insert size of 1.3 kbp. The library was estimated to contain $2×10^6$ pfu and was supplied at atitre of approximately $2.4×10^{10}$ pfu/ml. The master lambda Uni-ZAP XR library was supplied following a single round of amplification. A mass excision reaction (below) was conducted on this 1× amplified material to enable manipulations such as plating, replicate production and banking of master stocks to be conducted at the level of individual clones of viable *E. coli* and not as lytic plaques following phage lambda infection (Jerseth, B. et al (1992) *Strategies* 5: 81–83). The remaining library was further amplified once using standard procedures (Molecular Cloning, A Laboratory Manual eds. Sambrook J, Fritsch E F, Maniatis T. Cold Spring Harbor Laboratory Press 1989, New York, USA) and multiple glycerol stocks laid down as a master stock bank at −80° C.

The library was prepared for a mass excision reaction and plating as bacterial colonies according to protocols provided by the supplier (Stratagene, La Jolla, USA). Briefly, bacterial strains (XL-1 Blue and SOLR') supplied with the library were plated on selective medium (LB tetracycline and LB kanamycin respectively) and single colonies picked for overnight culture at 30° C. in 50 ml of LB broth [10 g/l NaCl, 10 g/l tryptone, 5 g/l yeast extract, pH 7.0] supplemented with 0.2% (w/v) maltose and 10 mM MgSO4. Cells were collected by centrifugation and resuspended in 10 mM $MgSO_4$ at a density of $8 \times 10^8$ cells/ml ($OD_{600}$=1.0). XL-1 Blue cells were combined with a portion of the lambda Uni-ZAP XR library at a multiplicity of infection of 1:10 lambda phage:cells. M13 based helper phage strain ExAssist (Stratagene, La Jolla, USA) was added at a ratio of 10:1 helper phage:cells and the mixture incubated at 37° C. for 15 minutes. 20 ml of LB broth was added and the mixture incubated at 37° C. with shaking for a further three hours. The mixture was heated at 70° C. for 20 minutes and the cell debris collected by centrifugation. The supernatant containing the excised phagemids was collected and 1 µl was added to 200 µl of SOLR' cells. The mixture was plated onto LB ampicillin plates and incubated overnight at 37° C. Typically many 1000's colonies resulted on each plate and further dilution of the excised phagemid preparation was required to get suitable plating densities for colony picking.

In order to make feasible to gridding process, the total number of individual cDNA clones was reduced whilst maintaining representation of the library. This normalization was achieved following the procedure of Soares et al (Soares, M. B. et al 1994, Proc. Natl. Acad. Sci USA vol 91: 922–923). The procedure required the production of single-strand molecules by helper-phage infection of the phagemid library. The single strand circles were subjected to controlled primer extension followed by denaturing and reannealing under conditions whereby high abundance molecules re-associated (low $C_o t$) and could be removed from the mixture by hydroxyapatite column chromatography. Non-reassociated circles were recovered from the flow through and transformed directly into competent bacteria.

Single-strand rescue was conducted on the phagemid library using helper phage VCM13 and protocols provided by the supplier (Stratagene). Rescued single-stranded DNA was purified according to the method of Soares et al (Soares et al ibid) incorporating particular steps to eliminate contaminating double-stranded DNA. Controlled primer extension was conducted on purified single-stranded circular DNA using primer (SEQ ID NO.: 61) 5' ggaaacagctatgaccatg, using the conditions of Soares et al. DNA polymerase was from Boehringer, nucleotide triphosphates were from Life Technologies (Paisley, UK). a $^{32}P$ dCTP used as tracer was from Amersham International (Amersham, UK). Hydroxyapatite column chromatography was conducted at 60° C. as described in Soares et al. Following recovery of the normalized single-stranded circles, the purified DNA was directly transformed into competent XLI-blue E. coli cells and plated on LB-ampicillin plates as previously described.

Individual colonies of XL 1-blue cells from the normalised library were picked for further analysis and replicate production. Briefly, colonies were manually picked into 96 well plates containing 100 µl LB ampicillin medium and grown for 3 hours at 37° C. One replicate was made of each plate using a BioRobot9600 (Qiagen UK Ltd, Crawley UK) laboratory workstation. The robot was programmed to pipette 50 µl of the culture into medium containing 10% (v/v) glycerol and this plate was sealed and stored as a master stock at −80° C. The remaining 50 µl culture was inoculated into 96-well flat-bottom block with 2 ml square wells containing 1.8 ml LB-ampicillin medium. A microporous tape sheet was applied to the top of each block and the block incubated overnight at 37° C. with orbital shaking. Following incubation, phagemid DNA was prepared from each of the 96 wells using standard programmes on a BioRobot9600 (Qiagen UK Ltd, Crawley UK) and the QIAwell Ultra reagent systems provided by the supplier (Qiagen UK Ltd Crawley, UK).

A portion of the purified DNA was used directly as templates for linked in vitro transcription translation (IVTT) using T3 RNA polymerase and a rabbit reticulocyte lysate system supplied by Promega UK Ltd (Southampton, UK). The remaining DNA was sealed for storage at −20° C. The IVTT reaction mix was supplemented with 2% (v/v) tRNA-biotinyl-lysine (Promega UK Ltd, Southampton, UK ) to enable capture of in vitro translated proteins onto a streptavidin coated solid phase. IVTT reactions were conducted in 96 well arrays in a total volume of 25 µl at 30° C. for 60 minutes. Following incubation, 5 µl each reaction was taken into 100 µl TSB pH 8.0 (50 mM Tris, 138 mM NaCl, 2.7 mM KCl) previously added to the wells of a Reacti-Bind™ steptavidin coated pre-blocked plate (Pierce, Chester, UK). The remaining IVTT reaction plate was sealed for storage at −20° C. The Reacti-Bind™ steptavidin plate was incubated at room temperature for 60 minutes with gentle rocking to promote binding of the biotinylated IVTT product to the plate surface. The plate was washed using 3×200 µl wash buffer (TBS, 0.1% (w/v)BSA, 0.05% (v/v)Tween 20) before use in tissue protein binding assays.

EXAMPLE 4
Method for Performing Tissue Extract Modification of In Vitro Translated Protein Arrays and Detection of Phosphorylation of Arrayed Proteins.

Human brain tissue samples were obtained from NeuroResouce (London, UK). Matched samples of normal and Alzheimers disease brain were provided. In general 1–10 g each sample was provided, in all cases samples were from known sub-anatomical location and cross-indexed to full clinical details. All samples were snap frozen at point of sampling and shipped on dry-ice and stored under liquid nitrogen before processing. Processing was conducted under Category 2 containment.

Phosphorylation competent brain tissue extracts were produced by disruption of the tissue in ice cold RIPA buffer. In some experiments, extracts competent for phosphatase activity were also produced; in this case lysates were produced using RIPA buffer without 1 mM $Na_3VO_4$. Tissue samples were thawed on ice and disrupted using a sterile disposable tissue grinder ("pellet pestle" Anachem Ltd, Luton, UK). Homogenisation was conducted using 2 volumes of ice cold RIPA buffer to 1 volume of tissue. The lysate was incubated with gentle shaking on ice for 15 minutes then cleared of insoluble material by centrifugation at 13,000×g at 4° C. for 10 minutes. The supernatant was removed and assayed for protein concentration using the bicinhoninic acid method and protocols provided by the supplier (Pierce, Chester UK, cat#23225). The lysate was divided into multiple aliquots, snap-frozen on dry ice and stored in liquid nitrogen.

Brain tissue lysate was reacted with the IVTT protein array in 96-well format by incubation of thawed lysate with the washed array for 30 minutes at 37° C. In general 10 µl lysate was added to each well of the protein array. Following incubation, the plates were washed x3 using 200111 wash buffer per well and incubated with any of several diluted anti-phosphoprotein antibody preparations. Phosphotyrosine modification was detected using anti-phosphotyrosine-HRP conjugate monoclonal cocktail (Zymed, Cambridge UK, #136620). Phosphoserine/phosphothreonine modification was detected using anti-phosphoserine/phosphothreoinine Iphosphotyrosine polyconal preparation (Zymed, Cambridge UK, cat#90-0200). In all cases, antibody incubation was conducted using antibodies diluted in TBS containing 5% BSA, for a minimum of 1 hour at 37° C. or in some cases overnight incubation at 4° C. Plates were washed as previously before detection with respective secondary reagents/chromogenic substrates following standard protocols (Antibodies A Laboratory Manual eds. Harlow, E. and Lane, D. Cold Spring Harbor Laboratory Press 1988 New York, USA). Plates were read at 492 nm.

EXAMPLE 5
Method For Detecting Protein-protein Binding using Labelled Tissue Proteins on In Vitro Translated Protein Arrays.

The proteins of a brain tissue lysate were labelled with fluorescein using the FluroTag™ FITC conjugation system supplied by Sigma (Poole, UK). Typically 5 mg brain protein was reacted with 250 µl of a dilution of a 1 mg/ml fluoroscein-isothiocyanate (FITC) solution in 0.1 M carbonate-bicarbonate buffer. The labelling reaction was allowed to proceed for 2 hours at room temperature before purification of unincorporated FITC using G-25 Sephadex column chromatography. Columns and procedures were as provided in the FluroTag™ kit (Sigma, Poole, UK). The column eluate containing the labelled brain proteins was stored at 4° C. protected from light.

Labelled tissue lysate was reacted with the IVTT protein array as previously. To detect labelled brain proteins captured by members of the IVTT protein array, the plate was washed as previously and incubated with an anti-fluorescein antibody (Sigma #F-5636, Sigma, Poole, UK). The antibody was diluted 1/2500 in TBS containing 5% BSA and incubated for 30–60 minutes at room temperature. The antibody was detected using an anti-mouse-HRP complex followed by reaction with the chromogenic substrate o-phenylenediamine (Sigma, Poole UK) according to standard procedures (*Antibodies, A Laboratory Manual*, ibid). Plates were read at 492 nm.

EXAMPLE 6
Protein-protein Binding Partners Identified by Ribosome Display Library In this example, the in vitro translated protein array is used to search a ribosome display library for binding partners, and the genes for binding partners present in the library are identified by reverse-transcription polymerase chain reaction (RT-PCR). For the purpose of this example, the ribosome display library is essentially as described in example 1 and, in practice, at point of use for screening using the IVTT protein array, consists of a large population ($10^9$–$10^{12}$) of ribosomes each individually tethered to a nascent protein by linkage to its cognate mRNA molecule.

The library was diluted 1 in 5 in ice-cold dilution buffer (50 mM Tris Acetate pH 7.5, 150 mM Sodium Chloride, 50 mM Magnesium Acetate, 0.1% Tween 20 with 200 u/ml of RNasin (Promega UK Ltd, Southampton UK). 50 µl of the diluted library was added to each well of the IVTT protein array and incubated at 4° C. for 1 hour with gentle shaking. Following incubation, wells of the array were washed 5 times using 100 µl ice-cold dilution buffer. The mRNA from any bound mRNA/ribosome/protein complexes was eluted by addition of 20 µl of 50 mM Tris acetate pH 7.5, 150 mM Sodium Chloride, 20 mM EDTA and incubating on ice for 10 minutes with gentle shaking. Eluted mRNA was collected into a second 96 well plate and concentrated by precipitation with ethanol at −20° C. overnight (Molecular Cloning, A Laboratory Manual ibid) in the presence 20 µg of glycogen carrier, (Boehringer, Lewes, UK). The resulting mRNA was used as a template for reverse transcription with M-MLV reverse transcriptase (RT). Briefly, mRNA was heat denatured at 70° C. for 10 minutes in the presence of 1 nM of the primer RD3 [5'(T)$_{18}$nn]. The mixture was chilled on ice before addition of 200u M-MLV-RT and its reaction buffer (Life Technologies, Paisley, UK). The mixture was incubated for 60 minutes at 37° C. then shifted to 70° C. for 15 minutes to inactivate the RT. The subsequent DNA:RNA hybrid was used as a template for PCR, using primers T75L (SEQ ID NO.: 64) [5' cggtttccctctagaaata] and RD3 and cycled×40 at 95° C. for 30 seconds, 50° C. for 30 seconds, 72° C. for 30 seconds. Thermostable DNA polymerase (Expand™ High Fidelity), reaction buffer and nucleotide triphosphates were from Boehringer (Boehringer, Lewes, UK). PCR products were analysed by agarose gel electrophoresis (Molecular Cloning, A Laboratory Manual, ibid). The presence of a PCR product identified putative positive binding partners in the IVTT protein array. The protein array was de-coded and phagemid DNA identified for sequence analysis. PCR products from the polysome display library were sequenced directly using primer T75L. Sequencing was conducted using dye-terminator chemistry according to protocols provided by the supplier (Amersham International, Amersham UK). Reactions analysed using an automated sequencing system (Applied Biosystems, Warrington, UK).

EXAMPLE 7
Microarrays of In Vitro Translated Protein Library onto a Streptavidin Coated Glass Surface.

Miniaturisation of the IVTT protein array was achieved by robotic gridding of individual IVTT proteins onto a glass surface pre-bound with streptavidin. The glass "chips" with streptavidin attached covalently to one surface were purchased from Radius Inc (Medfield, Ma., USA). Glass chips were 55 mm×25 mm. Using the gridding robot (Radius Inc, Medfield, Ma., USA), 0.5 µl of each of 96 IVTT reactions was applied to the dry surface of the chip in a low density array of 8 by 12. In further experiments, double density arrays of 192 individual proteins per glass chip were produced. In subsequent experiments very high density arrays suitable for high throughput screening were assembled. Following gridding, the chip surface was washed using phosphate buffered saline (PBS) and slides stored at 4° C. in PBS containing 3% (w/v) BSA and 0.02% sodium azide:

The IVTT protein chip arrays were treated with tissue lysates and probed with anti-phosphoprotein antibodies broadly as given in example 2. Protein chip arrays were washed extensively by immersion in tris buffered saline (TBS) prior to incubation with brain tissue lysates. Excess washing solution was shaken from the slide before 15 µl of brain tissue lysate was applied directly to the surface over the area encompassing the protein array. A glass coverslip was placed over the tissue lysate solution serving to spread the lysate over the whole area of the array and being held by capillary effect stop significant solution loss during the subsequent incubation. The incubation was conducted for 30 minutes at 37° C. with the glass chip placed in a humidified container. Following incubation, the coverslip was removed and the slide washed by immersion in wash buffer. The glass chip was incubated with one or combinations of anti-phosphoprotein antibodies diluted as per example 2. Antibody solution was applied in small volume (10–20 µl) to the protein array, and held in place under a coverslip as previously. Detection of bound antibody was by use of chromogenic substrates yielding insoluble precipitate onto the glass slide. Typically, substrate DAB (diaminobenzidine tetrahydrochloride) (Sigma, Poole, UK) was used. Positive signals in low density arrays were identified by visual examination of the array under low-power magnification. For some experiments an enhanced chemiluminescent substrate (Pierce & Warriner Ltd, Chester UK) was used in combination with peroxidase conjugated primary or secondary antibodies. Positive signals were detected using a Molecular Imager FX (BioRad Laboratories Ltd, Herts, UK) phosphor imager system.

Protein-protein binding assays were performed on the IVTT protein glass chip arrays using FITC labelled brain protein and broadly as described in example 5. 10–20 µl FITC labelled brain protein preparation was applied directly to the surface of a washed IVTT protein array. A glass coverslip was placed over the labelled tissue lysate solution, and the complete slide incubated at 37° C. for 30 minutes in a humidified container. Following incubation, the coverslip was removed and the slide washed by immersion in wash buffer.

In some experiments the bound FITC labelled protein was detected directly by fluorescence microscopy. For microscopy, the protein array was covered with one drop of antifade mountant (Vector Labs, Peterborough, UK) and a conventional coverslip for oil immersion fluorescence microscopy. The microscope was a Nikon type 105 fitted with an FITC compatible filter set for fluorescence microscopy. The position of protein spots giving positive signal was de-coded by reference to three-digit readings on the X-Y axis from the microscope stage under fluorescence illumination. These readings were related to the protein array co-ordinates following examination of an index spot etched on each glass surface prior to robotic gridding. The index spot was identified under conventional illumination to give the X-Y readings for its position relative to the protein array.

Some experiments were conducted using indirect detection of the bound labelled protein. For these, and anti-FITC monoclonal antibody was used, followed by an anti-mouse peroxidase conjugate and colourimetric detection using DAB as the reporter substrate. In this instance, reagents were from Sigma (Poole, UK) and the incubations were conducted using small volumes (10–20 µl) of diluted antibodies applied directly to the glass surface and held under coverslips as previously described. Positive signals were identified by visual examination of the array using low-power magnification under conventional illumination. Further experiments also used an enhanced chemiluminescent substrate (Pierce & Warriner Ltd, Chester UK) and imaging using a phosphor imager system as previously.

EXAMPLE 8

Method for Production of a Single Chain Antibody Library Immobilised onto a Solid Phase Array for Reaction with Tissue Extracts.

An extract of normal human brain, prepared as in example 4, was used to immunise two BalbC mice. 2 doses were given intra-peritoneally with an interval of 4 weeks between them. 3 to 4 days after the 2nd inoculation, the mice were sacrificed and spleens removed by dissection. A 25 cm$^2$ tissue culture flask was coated with the brain extract proteins at 25 µg/ml in carbonate/bicarbonate buffer pH 9.0. After incubation for 1 hour at 37° C., the antigen preparation was removed and sterile blocking buffer (2% non-fat dry milk in PBS) added and incubated for 1 hour. After washing 3 times with PBS, 25 ml of spleen cell suspension in tissue culture medium was added to the flask and incubated overnight at 37° C. in a 5% $CO_2$ atmosphere. The medium containing the non-adherent spleen cells was removed. RNA preparation was then initiated from the adherent selected cells by adding 1.5 ml of the Extraction buffer from the QuickPrep™ mRNA purification kit (Pharmacia, St Albans, UK) to the flask and swirling over the surface. 3 ml of the Elution buffer was then added and mixed. The flask contents were then transferred to a 15 ml centrifuge and the QuickPrep™ mRNA preparation continued according to the manufacturer's instructions The Pharmacia Recombinant Phage Antibody System (Pharmacia, Milton Keynes, UK) was used to produce a library of mouse single chain Fvs (ScFv) against human brain. First-strand cDNA was generated from the mRNA using M-MuLV reverse transcriptase and random hexamer primers. Antibody heavy and light chain genes were then amplified using specific heavy and light chain primers complementary to conserved sequences flanking the antibody variable domains. The 340 and 325 base pair products generated for heavy and light chain DNA respectively were separately purified following agarose gel electrophoresis. These were then assembled into a single ScFv construct using a DNA linker-primer mix to give the VH region joined by a (Gly4Ser)3 peptide to the VL region. The assembled ScFv were amplified with primers designed to insert Sfi 1 and Not 1 sites at the 5' and 3' ends respectively, giving an 800 bp product. This fragment was purified, sequentially digested with SfiI 5 and NotI, and repurified.

For production of an in vitro transcribed and translated ScFv library, the vector pBluescript SK+ was modified by the insertion of the linker between the HindIII and Eco RI sites in the multiple cloning site region:

Linker Sequence: SEQ ID NOS. 2–3

5' AGCTTGGCCCAGCCGGCCATGGCCCAG-GTCCAACTGCAGGAGCTCGAGCT-CAAACGGGCGGCCGCG3'

3' ACCGGGTCGGCCGGTACCGGGTCCAGGT-TGACGTCCTCGAGCTCTAGTTTGCCCGC-CGGCGCTTAA5'

SfiI NotI

The amplified ScFv were cloned between the SfiI and NotI sites of this vector such that they were inserted in the correct orientation for transcription from the T7 promoter. Alternatively, a human naive phage antibody library (Nissin, MRC) was used. Phagemid DNA was prepared and cut sequentially with SfiI and Noti. The ScFv fragments were purified and cloned into the modified pBluescript SK+ vector described above.

For use as a solid phase array, individual pBluescript clones were picked and grown in multiwell dishes as per example 3. DNA preparation, IVTT and array of biotinylated proteins was as per example 3.

For use as a phage antibody library, the Pharmacia protocol was followed. The assembled ScFv were amplified with primers designed to insert SfiI and NotI sites at the 5' and 3' ends respectively, giving an 800 bp product. This fragment was purified, sequentially digested with Sfi 1 and Not 1, repurified and ligated into SfiI and NotI cut pCANTAB 5 phagemid vector. PCANTAB 5 contains the gene encoding the Phage Gene 3 protein (g3p) and the ScFv is inserted adjacent to the g3 signal sequence such that it will be expressed as a g3p fusion protein. Competent *E. coli* TGI cells were transformed with the pCantab 5/ScFv phagemid then subsequently infected with the M13KO7 helper phage. The resulting recombinant phage contained DNA encoding the ScFv genes and displayed one or more copies of recombinant antibody as fusion proteins at their tips.

Phage-displayed ScFv that bind to human brain antigens were then selected or enriched by panning. Briefly brain antigen preparation was coated onto wells of 96-well microtitre plates. After blocking with 2% non-fat dry milk in PBS, the phage preparation was applied and incubated for 1 hour. After washing extensively with PBS, wells containing brain antigen reactive recombinant phage were detected with horse radish peroxidase conjugated anti-M13 antibody and revealed with o-phenylene diamine chromogenic substrate.

EXAMPLE 9

IVTT Display Library Gridded and Treated with Labelled Tissue Protein.

A single chain antibody IVTT display library was translated in vitro and arrayed onto streptavidin surface as per example 3. The single chain antibody array was reacted with FITC labelled brain proteins as prepared in example 5. Reaction procedure and detection of protein:protein binding was as per example 5. Patterns of positive signals from replicate IVTT arrays treated with different tissue proteins were compared. For. identification of individual proteins at specific loci on the arrays, the corresponding single chain antibody gene was recovered from the master plate of library cDNAs. Single chain antibody genes of interest were then resubjected to larger scale IVTT and used either to retrieve and identify binding partners from an IVTT protein library as described in example 6 or to retrieve and identify (by 2D gels) natural tissue protein as described in example 1.

EXAMPLE 10

Use of DNA Chips to form a Ribosome Display

In order to form a polysome display library for subsequent immobilisation onto a DNA chip, the library would be formed essentially as described in example 1 except that one of the primers used to clone the cDNAs into the IVTT vectors would comprise a mixed primer with a tract of variable sequence within the transcribed sequence designed to anneal to the DNA molecules on the chip. Alternatively, the plasmid pool from the display library would be digested with a unique restriction enzyme within the transcribed sequence and a mixed synthetic oligonucleotide cloned in. Thus the library would be constructed such that each mRNA molecule produced would contain a unique sequence tag; this would be at least 15 nucleotides, preferably about 20 nucleotides.

The experiments to test the DNA chip protein array method were conducted using a pair of modified single chain antibody (scAbs) genes. Two modified scAbs were prepared consisting M-terminal epitopr tags, the heavy chain variable region (VH) a 14 amino acid linker SEQ ID NO: 4 (EGKSSGSGSESKVD) the light chain variable region (VL), fused to cDNA for the human κ constant region. The human κ constant region sequence, which included a poly-Histidine tag at the 3' end, was modified to delete the stop codons. The human κ constant region is included to act as a spacer to allow correct folding of nascent single chain Fv while still attached to a ribosome complex in an in vitro translation system.

These constructs were cloned into the vector pET 5c (Rosenberg AH et al., Gene, 25 56:125–135, 1987) which provides a t7 promoter followed by the ribosome binding site from T7 gene 10. The scAb constructs were inserted into the vector at an NdeI site such that the sequence encoding the epitope tag followed the first Atg of T7 gene 10. The first construct consisted of a scAb against Pseudomonas aeruginosa (Molloy P. et al. Journal of applied Bacteriology, 78:359–365, 1995) with the FLAG epitope SEQ ID NO: 58 (MDYKDDDK) (Knappik A and Pluckthun A, BioTechniques, 17: 754–761, 1994) added at the N terminus. The second consisted a scAb constructed from the antibody 340 (Durrant LG et al. Prenatal Diagnosis, 14:131–140, 1994) with a poly-Histidine tag at the N terminus.

These plasmids served as parents for subsequent derivatives. The anti-*Pseudomonas aeruginosa* (α-Ps) scAb and the 340 scAb were constructed as follows. DNA for the α-Ps sc Ab in the vector pPH 1His (Molloy P et al., ibid) was amplified with the prime SEQ ID NOS: 59–60 RD 5' FLAG: 5'gcggatcccatatggactacaaagac-gatgacgacaaacaggtgcagctgcag3' (Genosys Biotechnologies Europe Ltd, Cambridge, UK) and RD 3': 5' gcgaattcgtggtg-gtggtggtggtgtgactctcc3' (Genosys) which introduced the 5' FLAG epitope sequence and removed the 3' stop codon respectively. The reaction mixture included 0.1 μg template DNA, 2.6 units of Expand™ High Fidelity PCR enzyme mix (Boehringer Mannheim, Lewes, UK.), Expand HF buffer (Boehringer Mannheim), 1.5 mM $MgCl_2$, 200 μM deoxynucleotide triphosphates (dNTPs) (Life Technologies, Paisley, UK) and 25 pmoles of each primer. Cycles were 96° C. 5 minutes, followed by [95° C. 1 minute, 50° C. 1 minute, 72° C. 1 minute] times 5, [95° C. 45 seconds minute, 72° C. 1 minute 30 seconds] times 8, [95° C. 45 seconds, 50° C. 1 minutes] times 5, finishing with 72° C. 5 minutes. The 1123 bp product obtained was cut with BamHI and EcoRI and cloned into the vector pUC19 (Boehringer Mannheim). The DNA sequence was confirmed, using the Thermo Sequenase radiolabeled terminator cycle sequencing kit with [$^{33}$P] dideoxy nucleotides (Amersham Life Science, Amersham, UK). The construct was cloned into pET5c vector (Promega UK Ltd, Southampton, UK.) as a NdeI to EcoRI fragment (see *Molecular Cloning, A Laboratory Manual* eds. Sambrook J, Fritsch E F, Maniatis T. Cold Spring Harbor Laboratory Press 1989, New York, USA). Plasmid DNA was prepared using Wizard® Plus SV Minipreps DNA purification System (Promega UK Ltd), or for larger scale, Qiagen Plasmid Midi Kit (Qiagen Ltd, Crawley, UK.). The new plasmid generated was named pET5c FLAG αPs scAb.

The 340 scAb was produced by substitution the VH and VK of the 340 antibody in place of the α-Ps VH and VK in ppM1His. The 340 VH was amplified with the primer SEQ ID NOS: 5–6 5' cagtctgggggaggcttag3' (Genosys) and 5' tcagtagacggtgaccgaggttccttgacccagta3' (Genosys). The reaction mixture included 0.1 μg template DNA, 2.6 units of Expand™ High Fidelity PCR enzyme mix, Expand HF buffer, 1.5 mM MgCl2, 200 μM dNTPs and 25 pmoles of each primer. Cycles were 96° C. 5 minutes, followed by [95° C. 1 minute, 50° C. 1 minute, 72° C. 1 minute] times 5, [95° C. 45 seconds, 50° C. 1 minute, 72° C. 1 minute 30 seconds] times 8, [95° C. 45 seconds, 50° C. 1 minute, 72° C. 2 minutes] times 5, finishing with 72° C. 5 minutes. The 357 bp product was cut with PstI and BstEII and cloned into PstI and BstEII cut pPM1His (see *Molecular Cloning, A Laboratory Manual*, ibid). Similarly, the 340 VK was amplified with the primers SEQ ID NOS: 7–8 5'gtgacattgagctcaca-cagtctcct3' and 5' cagcccgttttatctcgagcttggtccg3' (Genosys). The 339 bp product was cut with SstI and XhoI and cloned into SstI and XhoI cut modified pPM1His (produced above). The DNA sequence was confirmed, using the Thermo Sequenase radiolabeled terminator cycle sequencing kit with [$^{33}$P] dideoxy nucleotides (Amersham). DNA for the 340 scAb in the vector pPM1His was amplified with the primers RD 5' HIS: SEQ ID NO: 9 5'gcggatcccatatgcaccatcatcac-catcaccaggtgcagctgcag3' (Genosys) and RD 3' (given above) which introduced the 6 histidine residues at the 5' end and removed the 3' stop codon respectively. Reagents and conditions for amplification were exactly as for the α-Ps construct. The 1114 bp product obtained was cut with BamHI and EcoRI and cloned into the vector pUC19 (see *Molecular Cloning, A Laboratory Manual*, ibid). The DNA sequence was confirmed as before and the construct was cloned into pET5c vector as a NdeI to EcoRI fragment to generate the plasmid pEt5c HIS 340 scAb.

Model genes were modified to contains nucleicid "capture domain" sequence. Synthetic oligonucleotides SEQ ID NOS: 10–15 used were as follows;

Capture domain:
5'-aga ata cag ggt cca aat aga atc cag ggt
cap3inner:
5'-acctataaaaataggcgtatcacgaggcccttcgtcttcaataattc
cap3outer:
5'-agcgaattcaccctggattctatttggaccctgtattctacctataaaatagg
cap5inner:
5'-ggtttccctctagaatacagggtccaaatagaatccagggtaagaagg agatatacatatg
cap5outer:
5'-atatatatgtcgacgaaattaatacgactcactatagggagaccacaacgg tttccctctagaatac
T7loop:
5' atatatatgtcgacgaaattaatacgactcactatagggagaccacaacg The capture domain sequence was derived from the SFFV friend erythroleukeamia virus and has previously been shown to have no complementary sequence in mammalian cDNA databases [Tavitian et al (1998), *Nature Medicine* 4: 467–471]. The capture domain was inserted either into the 5' UTR region of the model genes described above, or fused into the 3' region of the said genes. Constructs were designated CAP5 or CAP3 variants respectively. Insertion of the CAP5 and CAP3 domains was achieved by PCR using primers designed to be universal for each of the available model genes. For CAP5 insertion, two serial PCRs were conducted using primers CAP5 inner and RD3, followed by a second PCR with primers CAP5 outer and RD3. The resulting product was purified and used directly in an in vitro transcription reaction. Insertion of the CAP3 domain proceeded according to the same scheme, however primer CAP3innner was used in the primary PCR with primer T7loop, followed by a secondary PCR using primers CAP3outer and T7loop. The purified product was used directly in an in vitro transcription reaction. Transcription reactions were carried out using 17 RNA polymerase and the RiboMAX system (Promega, Southampton UK) using conditions recommended by the supplier. RNA was hybridised to a synthetic DNA oligonucleotide covalently attached to the surface of a microtitre plate. The capture oligonucleotide was of complementary sequence to the capture domain within the RNA. In some experiments the capture oligonucleotide was attached via a 5'-amino-linker moiety, and in other experiments attachment was via the 3' end of the molecule. Microtitre plates with attached oligonucleotides were supplied under contract by GenoSys Biotechnologies Europe Ltd (Cambridge, UK). The hybridisation reaction was conducted for 60 minutes at 55° C. in a reaction buffer containing tetramethylammonium chloride as described by Maskos and Southern (Maskos U & Southern E.M. (1992) *Nucleic Acids Res.* 20: 1675–1678). Post hybridisation washes were conducted to high stringency using dilutions of an SSPE buffer containing 0.1% (v/v) SDS (1×SSPE buffer= 108 mM NaCl, 10 mM sodium phosphate pH 7.7, 1 mM ethylenediaminetetra acetic acid).

Following the final wash, in vitro translation reaction was initiated by addition of 25 µl rabbit reticulocyte lysate (Promega) supplemented with a complete amino acid mixture. In some experiments a methionine minus amino acid mix was used, in this case $^{35}$S-methionine (Amersham) was added. The translation reaction was conducted at 30° C. for 60 minutes then placed on ice. Wells were washed using ice cold PBS containing 1% (w/v) BSA Translation products were detected using antibodies for either the Flag or the his6 epitope engineered into each of the model gene constructs. Antibodies were added to the washed wells diluted in PBS. Incubations were for 60 minutes at 4° C. with gentle mixing. A secondary reagent (anti-mouse-HRP conjugate), was added at the recommended dilution in PBS and incubated for a further 30 minutes at 4° C. Wells were washed three times using 200 µl PBS before colour development with the chromogenic substrate. Plates were read at 492 nm. Where $^{35}$S-methionine was included in the reaction mix, translation products were detected by scintillation counting. The results indicated successful immobilisation of the correct protein by virtue of attachment to its associated mRNA in turn annealed to the corresponding immobilised DNA by virtue of the complementary region of sequence.

EXAMPLE 11

Ribosome Display with tat and SRP

The starting point was two single-chain antibody genes (scFv) specific for the epidermal growth factor receptor (EGFR) derived from antibody 340 and for the prostate surface membrane antigen (PSMA) derived from antibody J59 1, each cloned into an *E.coli* expression vector, pPMhis. The scFv fragments were recloned into a PGEM T7/SP6 plasmid (Promega, Southampton, UK) providing an upstream promotor for T7 RNA polymerase using long synthetic oligonucleotides and PCR to provide an upstream bacterial ribosome binding site, a downstream spacer segment derived from the M13 phage gene III and a 3' tranrscirptional termination region from the *E. coli* lpp terminator. For both scFv's, the translational stop codon was removed by the PCR reaction. The resultant plasmids were called pT7340A (for EGFR) and pT7591A (for PSMA).

As variants of the basic plasmids above, an upstream anti-initiation segment and a downstream terminating segment and were provided by strand overlap extension PCR to insert, respectively, a secretory leader sequence between the ATG initiation codon and the scFv genes, and a terminal sequence TAR sequence between the spacer segment and the transcriptional termination sequence. The resultant plasmids were called pT7340B (for EGFR) and pT7591B (for PSMA).

In vitro transcription of the pT7 plasmids was performed using a RiboMAX™ kit (Promega, Southampton, UK) according to the manufacturer's instructions. The resultant mRNA was purified according to the manufacturer's protocol.

In vitro translation was performed in an *E. coli* S-30 system as described by Chen and Zubay (ibid) modified as described by Hanes and Pluckthun (ibid) and supplemented with HIV Tat 37–72 peptide. After 10 minutes of translation, a preparation of SRP (produced by the method of Romisch K, Webb J, Herz J, Prehn S, Frank R, Brenner S and Walter P, Nature vol 340 (1989) p478–482) was added and the translation was continued for a further 10 minutes. The translation was stopped and the mixture centrifuged as described by Hanes and Pluckthun (ibid). The translation reactions were then incubated for 1 hour at room temperature on microtitre plates with either EGFR or PSMA coated into the plates. Washing and dissociation of retained ribosome complexes, isolation of mRNA, reverse transcription-PCR and repeated transcription-translation were as described by Hanes and Pluckthun (ibid). After 5 rounds of ribosome display, the PCR products were cloned into pUC18 for sequence determination and determination of the representation of the original scFv's in the selected population of genes. For this determination the inserts in at least 50 pUC18 clones were sequenced.

For screening on an EGFR antigen preparation, an original plasmid mixture comprising a 1:1 molar ratio of pT7340A: pT7591A gave rise to a final pUC18 library consisting of 84% pT7340A sequence and 16% pT7591A. With a 1:1 molar ratio of pT7340A: pT7340B or a 1:1 molar ratio of pT7340B: pT7591B, the final pUC18 library comprised 100% of the pT7340B sequence in both cases.

EXAMPLE 12

The starting point was two single chain antibody (scFv) genes, one specific for digoxin (Tang et al., Journal of Biological Chemistry 270 (1995) p7829–7835) and the other for fluoresein (Denzin & Voss, Journal of Biological Chemistry 267 (1992) p8925–8931). The anti-digoxin scFv was PCR amplified from the pCANTAB vector (Tang et al.) using forward primer SEQ ID NO: 16 fdig1: CCG TAT AGA TCT CAG GTC AAA CTG CAG GAG TCT and reverse primer SEQ ID NO: 17 rdig1: CCG TAT GGA TCC CCG TTT TAT TTC CAA CTT TGT. PCR amplification reactions were performed using Boehringer Expand High Fidelity PCR system. Reaction conditions for amplification of DNA fragments were 1× Expand HF buffer, 2.5 MM MgCl$_2$, 4 mM of each dNTP, 2.5 units of polymerase, 10 ng template DNA and 30 pmol of primer DNA. Reactions were incubated in a thermal cycler using the following programme: 92° C. for 5 min, 53–67° C. (depending on primer sequence) for 5 min, 72 C for 1 min, followed by 30 cycles of 92° C. for 1 min, 53–67° C. for 1 min and 72° C. for 1 min. The resultant 720 bp fragment was then purified using Wizard PCR purification columns (Promega) and cloned into the *E. coli* expression vector pET-9 (Promega) at the BamHI site by digesting the PCR product and vector with BglII and BanHI according to the manufacturers instructions. This plasmid contains the promoter, translational start site and terminator from the bacteriophage T7 gene 10. The resultant plasmid was designated pDIG1. The anti-fluorescein scFv DNA sequence was generated as described by Mallender, Carrero & Voss (Journal of Biological Chemistry 271 (1996), p5338–5346) from the expression vector pGX8773 using forward primer SEQ ID NO: 18 fox1: CCG TAT AGA GAT GTC GTG AGT ACC CAA ACT and reverse primer SEQ ID NO: 19 rox1: CCG TAT GGA TVCC TGA GGA GAC GGT GAC TGA GGT. This fragment was generated by PCR and then cloned into the pET-9 vector as described above and designated pOX1.

A spacer sequence based on the glycine rich linkers of gene III of filamentous phage M13 was generated by performing PCR on a preparation of double stranded M13 DNA using the following two sets of primers SEQ ID NO: 20–23:

```
m13f1:  CCG TAT AGA TCT GGCTTTAATGAGGATCCATTC
                Bg/II m13r1:  CCG TAT CTC GAG CTGTAGCGCGTTTTCATCGGC
                XhoI m13f2:  CCG TAT GTC GAC GGCTTTAATGAGGATCCATTC
                Sa/I m13r2:  CCG TAT TGA TCA CTGTAGCGCGTTTTCATCGGC
                Bc/I
```

Two sets of PCR reactions were performed using primer combination m13f1 and m13r1 or with m13f2 and m13r2. These two sets of reactions generated two populations of products, one with a 5' BglII and 3' XhoI and one with a 5' SalI and 3' BclI restriction sites. The restriction sites were included to facilitate the construction of multimers of the 30 amino acid linker. The BlII/XhoI PCR products were double digested and phosphatased and then ligated with the digested SalI/BclI PCR products. In this way multimers ligated only 5' to 3' (which could be confirmed by digestion) would be formed. A 900 bp fragment was isolated by agarose gel electrophoresis and purified using Wizard PCR purification columns (Promega) according to manufacturers instructions. The fragment was then digested with BglII and BclI and cloned into the BamHI site of pDIGI and pOXI downstream of the scFv fragments to generate pDIG2 and pOX2 respectively.

As variants of the basic plasmids above, an upstream anti-initiation segment was inserted between the AUG initiation codon and the scFv genes. This was performed by incorporating a murine Vh signal sequence (Neuberger, EMBO J. 2 (1983) p1372–1378) to the scFv PCR primers fdig1 and fox1:

fdig2 SEQ ID NO: 24: CCG TAT AGA TCT ATG GGA TGG AGC TGT ATC ATC CTC TTC TTG GTA GCA ACA GCT ACA GGT GTC CAC TCC CAG GTC AAA CTG CAG GAG TCT FOX2 SEQ ID NO: 25: CCG TAT AGA TCT ATG GGA TGG AGC TGT ATC ATC CTC TTC TTG GTA GCA ACA GCT ACA GGT GTC CAC TCC GAT GTC GTG ATG ACC CAA ACT Following PCR in combination with rdig1 and roxI respectively, the resultant PCR products were digested with BglII and BamHI and cloned into the pET vector as previously described to generate pDIG3 and pOX3.

In addition the HIV transactivation response element (TAR) sequence was inserted downstream from the M13 spacer segment by-ligating the BclI digested 900 bp spacer fragment (generated as described above) to a self annealed oligonucleotideS SEQ ID NOS: 26–27 encoding the HIV TAR as follows:

TAR1: GATCAGCCAGATTTGAGCAGC

TAR2: GATCGCTGCTCAAATCTGGCT

The fragment was repurified and cloned into the BamHI site of pDIG3 and pOX3 to generate pDIG4 and pOX4.

Following cloning, sequencing of the PCR generated inserts was performed by the dideoxy chain termination method using a double-stranded plasmid DNA template (Kraft et al., BioTechniques 6 (1988), p544) and Sequenase (Amersham) using T7 sequencing primers.

In vitro transcription of the constructs pDIG3, pOX3 and pDIG4, pOX4 was performed using the RiboMAX large scale RNA production system (Promega) according to the manufacturers instructions. The resultant mRNA was purified using PolyATtract system (Promega).

In vitro translation with mixtures of anti-digoxin and anti-fluorescein scFv mRNAs were performed in an *E. coli* S-30 system as described by Chen and Zubay (ibid) modified as described by Hanes and Pluckthun (ibid) and in the presence or absence of 10 ug/ml HIV tat 37–72 peptide (Naryshkin et al., Biochemistry 36 (1997), p349–3505). In some samples, a preparation of SRP (produced by the method of Romisch et al., Nature 340, (1989), p478–482) was added after 10 minutes of translation and the translation continued for a further 10 minutes. The translation was stopped and the mixture centrifuged as described by Hanes and Pluckthun (ibid). The translation reactions were then incubated for 1 hour at room temperature on microtitre plates with either digoxin or fluorescein coated onto the plates. Washing and dissociation of retained ribosome complexes, isolation of mRNA, reverse-transcription PCR and repeated transcription-translation were as described by Hanes and Pluckthun (ibid). After 5 rounds of ribosome display, the PCR products were cloned into pUC18 for sequencing and determination of the original scFv's in the selected population of genes. For this deternination, the inserts in at least 50 pUC18 clones were sequenced.

The results of this analysis are shown in table 1 which indicates that translation reactions with added tat resulted in an increased selection of mRNAs encoding scFv's against the target ligand with some indication of increased selection with added SRP.

EXAMPLE 13
Protein-protein Binding from Dicistronic mRNAs

The human IL-5 protein was used to demonstrate that ribosome display can be used to identify interacting proteins by the use of dicistronic constructs. Three basic expression plasmids were constructed as detailed below;
Construct 1:

The human IL-5 gene was PCR amplified from pUC 18 (as supplied by R&D Systems, Abingdon, UK) using the following primers SEQ ID NOS: 28–29:

PCR amplification and purification were performned as described above. The PCR product was then digested with BglII and BamHI cloned into the BamHI site of the pET9 vector (Promega) and designated pIL5b.

A spacer sequence based on the glycine rich linkers of gene III of filamentous phage M13 was generated by performing PCR on a preparation of double stranded M13 DNA using the following primers m13f1, m13r1, m13f2 and m13r2, sequences as given above.

Two sets of PCR reactions were performed using primer combination m13f1 and m13r1 or with m13f2 and m13r2. These two sets of reactions generated two populations of products, one with a 5' BglII and 3' XhoI and one with a 5' SalI and 3' BclI restriction sites. The restriction sites were included to facilitate the construction of multimers of the 30 amino acid linker. The BglII/XhoI PCR products were double digested and phosphatased and then ligated with the digested SalI/BclI PCR products. In this way multimers ligated only 5' to 3' (which could be confirmed by digestion) would be formed. A 900 bp fragment was isolated by agarose gel electrophoresis and purified using Wizard PCR purification columns (Promega) according to manufacturers instructions.

The HIV transactivation response element (TAR) sequence was inserted downstream from the M13 spacer segment by ligating the BclI digested 900 bp spacer fragment (generated as described above) to self annealed oligonucleotides TAR1 and TAR2, encoding the HIV TAR as previously.

```
i15f1:   CCG TAT AGA TCT GAA ATT CCC ACT AGT GCA TTG
                 Bg/II i15r1:   CCG TAT GGA TCC GAC GTC CTC AAG CTT GGA ATA TTA TCA
                 BamHI                HindIII         stop GTG ATG GTG ATG GTG ATG ACT TTC TAT TAT CCA
                      His tag
```

PCR amplification reactions were performed using Boehringer Expand High Fidelity PCR system (Boehringer, Lewes, UK). Reaction conditions for amplification of DNA fragments were 1× Expand HF buffer, 2.5 mM MgCl2, 4 mM of each dNTP, 2.5 units of polymerase, 10 ng template DNA and 30 pmol of primer DNA. Reactions were incubated in a thermal cycler using the following programme: 92° C. for 5 min, 53–67° C. (depending on primer sequence) for 5 min, 72° C. for 1 min, followed by 30 cycles of 92° C. for 1 min, 53–67° C. for 1 min and 72° C. for 1 min. The resultant 448 bp fragment was then purified using Wizard PCR purification columns (Promega) and cloned into the *E. coli* expression vector pET-9 (Promega) at the BamHI site by digesting the PCR product and vector with BglII and BamHI according to the manufacturers instructions. This plasmid contains the promoter, translational start site and terminator from the bacteriophage T7 gene 10. The resultant plasmid was designated pIL5a.
Construct 2:

The human IL-5 gene was PCR amplified from pUC18 using the following primers SEQ ID NO: 30–31:

The fragment was repurified, digested with BglII and cloned into the BamHI site of pIL5b to generate pIL5c.
Construct 3:

pIL5c was digested with HindIII and BamHI to release the insert described in construct 2 and this was then cloned in to pIL5a which also had been digested with HindIII and BamHI. The resultant construct was designated pIL5d.

Following cloning, sequencing of the PCR generated inserts was performed by the dideoxy chain termination method using a double-stranded plasmid DNA template (Kraft et al., BioTechniques 6 (1988), p544) and Sequenase (Amersham, Little Chalfont, UK) using T7 sequencing primers.

In vitro transcription of the constructs pIL5a, pIL5c and pIL5d was performed using the RiboMAX large scale RNA production system(Promega) according to the manufacturers instructions. The resultant mRNA was purified using PolyATtract system (Promega).

In vitro translation was performed in an *E. coil* S-30 system as described by Chen and Zubay (ibid) modified as described by Hanes and Pluckthun (ibid) and supplemented

```
i15f2:   CCG TAT AGA TCT AAG CTT GAA ATT CCC ACT AGT GCA TTG
                 Bg/II   HindIII i15r2:   CCG TAT GGA TCC ACT TTC TAT TAT CCA CTC GGT
                 BamHI
``` with HIV tat 37–72 peptide (Naryshkin et al., Biochemistry, vol 36 (1997), p3496–3505). The translation was stopped and the mixture centrifuged as described by Hanes and Pluckthun (ibid). Purification of the translation mix was performed under denaturing conditions using the rapid affinity column chromatography with the pET-His-Tag system as described by Novagen (Cambridge Biosciences, Cambridge, UK). Bound proteins were eluted according to manufacturers instructions.

Anti-tat antibody was made using the tat peptide 37–72 which was conjugated via its N-terminal cysteine residue to KLH using MBS according to *Antibodies, A Laboratory Manual* ibid. 10 ug of the conjugate was used to immunise Balb/c mice as above and serum was collected and used at 1:100 dilution in the further experiments. Dilutions of pET-His-TagA-eluted material from above was applied to an Immulon 2 96-well microtitre plates (Dynatech, Chantilly, Va., USA) according to the manufacturer's instructions and anti-tat antibody was then added and incubated for 2 hours at room temperature. Plates were then washed 3 times with PBS, and a 1:1000 dilution of HRP-labelled goat anti-mouse antibody conjugate (#A4416, Sigma, Poole, UK) was added and incubated for a further 1 hour at room temperature. After 3 washes in PBS, TMB substrate was added according to *Antibodies, A Laboratory Manual* ibid.

The results showed that the eluted His-tagged protein was associated with tat protein in ELISA assays derived from the dicistronic plasmid pIL5d but not from a 1:1 mixture of monocistronic plasmids pIL5a and pIL5c where no bound tat was detected. This indicated that translated IL-5 had homodimerised from the dicistronic plasmid but not from the monocistronic plasmids.

EXAMPLE 14
Ribosome Display using Biotinylated Oligonucleotide and Streptavidin

Two modified single chain antibodies (scAb's) were prepared consisting of N-terminal epitope tags, the heavy chain variable region ($V_H$), a 14 amino acid linker SEQ ID NO: 4 (EGKSSGSGSESKVD), the light chain variable region ($V_L$), fused to cDNA for the human κ constant region. The human κ constant region sequence, which included a poly-Histidine tag at the 3' end, was modified to delete the stop codons.

Construction of modified anti-*Pseudomonas* scAb and modified 340 scAb was as given in example 10. In vitro coupled transcription and translation of the above plasmids was carried out as described in Promega Technical Bulletin No.219 using the *E. coli* T7 S30 Extract System for Circular DNA (Promega) with the addition of RNasin® 80 units/reaction (Promega) to all reactions. 2 µg of template DNA pET5c FLAG-αPs scAb or pET5c HIS-340 scAb was transcribed and translated in reaction mixes with and without the addition of an biotinylated oligonucleotide SEQ ID NO: 32 Cκ3' block (5' TTGAAGCTCTTTGTGACGGGCGAACTC3') and streptavadin. In addition, reaction mixes included 1 µL UTP α $^{33}$p (0.37 MBq) (ICN Ltd, Thame, Oxfordshire, UK) in a total volume of 50 µL. The reactions contained 3' biotinylated Cκ3'. block oligonucleotide at 5 µM and 1 ng of streptavidin (Boehringer Mannheim). Reactions were incubated at 30° C. for 30 minutes and stopped by the addition of magnesium acetate to 50 mM and cooling on ice (Hanes J and Pluckthun A, Proc. Natl. Acad. Sci. 94: 49374942, 1997). Reaction mixes were diluted 1 in 5 by the addition of 200 µL of ice-cold wash buffer (50 mM Tris acetate pH7.5, 150 mM sodium chloride, 50 mM magnesium acetate, 0.1% Tween 20 (Hanes and Pluckthun, ibid) with 1 µL (40 units) of RNasin® (Promega UK Ltd).

Proteins produced were characterised by Western dot blot using standard protocols (in *Antibodies A Laboratory Manual* eds. Harlow, E. and Lane, D. Cold Spring Harbor Laboratory Press 1988 New York, USA and Qiagen Western and Dot Blotting Protocols September 1997), detecting the translated protein with Penta His™ antibody (0.1 µg/ml) (Qiagen Ltd) or anti-FLAG M2 antibody (1.4 µg/ml) (Kodak Scientific Imaging Systems Ltd, New York, USA), followed by anti-mouse IgG HRP conjugate (0.5 µg/ml) (Sigma, Poole, UK.). Anti-human Cκ specific HRP conjugate (0.5 µg/ml) (The Binding Site, Birmingham, UK.) was used directly. Proteins were visualised by chemiluminescent detection (ECL, Amersham International Ltd) and autoradiography. A known concentration of anti-*Pseudomonas aeruginosa* scAb (Molloy et al., ibid) and transcribed and translated protein from the PinpointS control plasmid (Promega Technical Bulletin No.219) as supplied with the T7 S30 extract (Promega UK Ltd) were also subjected to analysis by Western dot blot to serve as positive and negative controls respectively.

Wells of an Immulon 4HBX 96 well plate (Dynatech) were coated with anti-FLAG M2 antibody at 2 µg/well in 50 mM carbonate-bicarbonate buffer pH9.5 (Sigma), Penta-His antibody at 2 µg/well in 50 mM carbonate-bicarbonate buffer, pH9.5, 5 mg/ml BSA (Sigma) in 50 mM carbonate-bicarbonate buffer pH 9.5 or with 50 µL per well heat killed *Pseudomonas aeruginosa* preparation (McGregor D et al. ibid). Wells were blocked with 1% Boehringer Blocking Agent (Boehringer Mannheim) for 60 minutes at room temperature. After washing wells 3 times with ice-cold wash buffer, 50 µL samples of the transcription/translation reactions were applied to the various capture wells and incubated rocking at 0° C. for 60 minutes. The unbound material was removed to fresh tubes. The wells were washed 5 times with ice-cold wash buffer. mRNA was eluted by the addition of 20 µL of 50 mM Tris acetate pH 7.5, 150 mM Sodium Chloride, 20 mM EDTA and incubating on ice for 10 minutes. For qualitative assessment of the amount of RNA captured, 2 µL samples of the unbound material and 20 µL samples of the eluted material were spotted on nitrocellulose membrane, allowed to air dry and autoradiographed. For more quantitative determination duplicate 5 µL samples of unbound and eluted material were spotted onto marked GF/C glass fibre filters (Whatman International Ltd, Maidstone, Kent, UK) and allowed to dry at room temperature. One of each pair of filters was transferred to a beaker containing ice-cold 5% Trichloroacetic acid (TCA) and 20 mM sodium pyrophosphate and swirled for 2 minutes. Filters were then transferred to a fresh beaker of TCA/pyrophosphate and the washing procedure repeated a further 2 times. Washed filters were briefly transferred to 70% ethanol, then dried at room temperature. Washed and unwashed filters were transferred to scintillation vials and scintillation fluid added. Filters were counted in a liquid scintillation counter. Unwashed filters give the total amount of radioactivity in the samples, washed filters give the amount of radioactivity incorporated into nucleic acid.

The results of this analysis are shown in table 1 which indicates that translation reactions with the biotinylated blocking oligonucleotide and streptavidin added resulted in an increased selection of mRNAs encoding scFv's against the target ligand. These experiments were repeated using the TNT® Coupled Reticulocyte Lysate System (Promega UK Ltd) in place of the *E. coli* T7 S30 Extract System for Circular DNA. Transcription translation reactions were set up as directed in Promega Technical Bulletin No. 126 and included TNT® rabbit reticulocyte lysate, TNT® buffer, complete amino acid mixture, RNasin® ribonuclease inhibitor, TNT® T7 RNA polymerase, 1 µg of template DNA pET5c FLAG-αPs scAb or pET5c HIS-340 scAb. The reactions were carried out at 30° C.

The results of this experiment are summarised in table 2 and indicate that translation reactions with the biotinylated blocking oligonucleotide and streptavidin added resulted in an increased selection of mRNAs encoding scFv's against the target ligand.

EXAMPLE 15

The experiment detailed in example 14 was repeated using the *E. coli* T7 S30 Extract System and transcriptionl/translation reactions were carried out exactly as described above except that the concentration of the blocking oligonucleotide was increased to 10 nM and 20 nM respectively with 1 ng streptavadin and the reaction was allowed to proceed for 2 hours.

An aliquot of the translated proteins was characterised by Western dot blot as described above. The remaining 45 µL of reaction mix was chilled rapidly on ice and magnesium acetate added to a final concentration of 50 mM. The reaction mix was then diluted to 200 µL with ice cold washing buffer. 50 µl of this reaction mix was added to each of four coated ELISA plate wells (50 µL heat killed *P. aeruginosa* cells or 100 µL of anti-FLAG M2 monoclonal antibody (2.8 µg/ml), or 100 µL Penta-His™ antibody (0.2 µg/ml) or 100 µL 2% BSA) then washed and blocked (as described for above) and incubated on ice for 1.5 hours. Wells were washed 5 times with ice cold washing buffer. mRNA was eluted from the washed plates with elution buffer (as described above) by incubating a further 10 minutes shaking on ice.

The niRNA was precipitated with ethanol at −20° C. overnight (*Molecular Cloning, A Laboralory Manual* ibid) in the presence 20 µg of glycogen carrier, (Boehringer Mannheim). The resulting mRNA was used as a template for reverse transcription with M-MLV reverse transcriptase (RT). Briefly, mRNA was dla d at 70° C. for 10 minutes and chilled on ice to anneal 1 nM of primer SEQ ID NOS: 33–34 HuCK FOR: 5' AGGCAGTTCCAGATTTC3', Seq 2 scAb: 5' GTGAGCTCGATGTCATCC3' and RD 3'. 200 units of M-MLV RT (Life Technologies) was added and incubated at 37° C. for 60 minutes, followed by heating to 70° C. for 15 minutes to inactivate the RT. The subsequent DNA:RNA hybrid was then used as a template for PCR, using RD5' Flag reverse primer with the forward primers (10 nM) described above. Reactions were incubated in the thermal cycler at 96° C. for 5 minutes followed by 40 cycles of 95° C. for 30 seconds, 50° C. for 30 seconds, 72° C. for 30 seconds then 72° C. for 6 minutes. PCR products were analysed by agarose gel electrophoresis.

The results from this experiment demonstrated that the increased concentration of the blocking oligonucleotide resulted in an increased selection of the scFv genes.

EXAMPLE 16

The experiment described in example 14 was repeated and transcription/translation reactions were carried out exactly as described above, except that the template was an equimolar mixture of pET5c FLAG α Ps scAb and pET5c HIS 340 scAb. Wells of ELISA plates were coated with 100 µL 2.8 µg/ml α FLAG M2 antibody and 50 µL heat killed *P. aeruginosa* preparation as before. Protein-ribosome-mRNA complexes were captured, eluted and nucleic acids precipitated, followed by DNase treatment as described in Experiment 4. The products were separated by electrophoresis through a low melting point agarose gel (Life Technologies) and full length PCR product (approximately 1100 bp) was isolated. This was used as template for a further round of PCR using primers to introduce upstream untranslated DNA sequence including a T7 promoter, ribosome binding site and Kozak sequences (Kozak M. Nucl. Acids Res. 18:2828, 1990) for prokaryotic and eukaryotic translation respectively, and a translation initiation codon. The resultant PCR product was then transcribed and translated using an S30 extract prepared for linear DNA (Promega UK Ltd). Protein-ribosome-mRNA complexes were captured, mRNA eluted, nucleic acids recovered and DNase treated as before, followed by RT PCR and introduction of the promoter and ribosome binding sites by PCR to produce template DNA for the next round. After 4 to 5 rounds of ribosome display the recovered DNA was inserted into the original vector and the DNA sequence of 20 clones determined. All 20 clones were found to contain the anti-pseudomonas scFv sequence.

EXAMPLE 17

Biological Screening

As models of cell lines producing a modulator as a result of stimulation of a biological response, the cell line A431 (ECACC No 85090402, from ECACC, Porton Down, UK) and an EGFR⁻ variant of HeLa (ECACC No 85060701) (selected using an anti-EGFR antibody conjugated to phospholipase C) were used for the experiments, in both cases using variants secreting the modulator protein HIV tat. Cells were grown in DMEM supplemented with 10% FBS. From both lines were derived recombinant cell lines secreting the tat protein as follows: A synthetic HIV tat gene was purchased from R and D Systems (Abingdon, UK) and PCR amplified using the following primers SEQ ID NOS: 35–36:

TATfor: 5'-CCG TAT CTC GAG ATG GGA TGG AGC TGT ATC ATC CTC TTC TTG GTA GCA ACA GCT ACA GGT GTC CAC TCC GAA CCA GTC GAC CCT AGA CTG-3'

TATrev: 5'-GAA TTC GGA TCC TTA CTA TTC-3'

The resultant PCR product was digested with XhoI and EcoRI and subcloned into a XhoI and EcoRI-digested pCI-neo vector (Promega, Southampton, UK). The tat expression plasmid was transfected into A431 and EGFR HeLa by electroporation using a Biorad GenePulser II (Biorad, Hemel Hempstead, UK) and selected in G418. Secretion of tat was confirmed by ELISA as follows: Anti-tat antibody was made using the tat peptide 37–72 which was conjugated via its N-terminal cysteine residue to KLH using MBS according to *Antidbodies A Laboratory Manual* ibid. 10 µg of the conjugate was used to immunise Balb/c mice as above and serum was collected and used at 1:100 dilution in ELISA experiments. A 10 ug aliquot of antibody was applied to an Immulon 2 96-well microtitre plates (Dynatech, Chantilly, Va., USA) according to the manufacturer's instructions, samples of cellular supernatants were then added and incubated for 2 hours at room temperature, plates were then washed 3 times with PBS, and a 1:1000 dilution of HRP-labelled goat anti-mouse antibody conjugate (#A4416, Sigma, Poole, UK) was added and incubated for a further 1 hour at room temperature. After 3 washes in PBS, TMB substrate was added according to *Antibodies, A Laboratory Manual* (ibid); this confirmed the presence of HIV tat protein in the culture supernatant of transfected but not untransfected A431 and EGFR⁻ HeLa cells.

For model protein ligands, two single chain antibody (scFv) genes were used encoding anti-EGFR (epidermal growth factor receptor) (PCT00443) and anti-fluorescein (Denzin & Voss, Journal of Biological Chemistry, vol 267 (1992) p8925–8931). The anti-EGFR scFv was PCR amplified from cloned Vh and Vk chains using the following primer SEQ ID NOS: 37–40;

340Vhfor: 5'-CAG CTG CAG GAG TCT GGG GGA GGC TTA G-3'

340Vhbck: 5'-TCA GTA GAC GGT GAC CGA GGT TCC TTG ACC CCA GTA-3'

340Vkfor: 5'-GTG ACA TTG AGC TCA CAC AGT CTC CT-3'

340Vkbck: 5'-CAG CCC GTT TTA TCT CGA GCT TGG TCC-3'

PCR amplification reactions were performed using Expand High Fidelity PCR system (Boehringer, Lewes, UK). Reaction conditions for amplification of DNA fragments were 1× Expand HF buffer, 2.5 mM MgCl2, 4 mM of each dNTP, 2.5 units of polymerase, 10 ng template DNA and 30 pmol of primer DNA. Reactions were incubated in a thermal cycler using the following programme: 92° C. for 5 min, 53–67° C. (depending on primer sequence) for 5 min, 72° C. for 1 min, followed by 30 cycles of 92° C. for 1 min, 53–67° C. for 1 min and 72° C. for 1 min. The resultant fragment was then purified using Wizard PCR purification columns (Promega). The PCR fragments of Vh and Vk were digested with PstI/BstEII. and SacI/XhoI respectively. The scFv vector was pPM1His (Molloy et al, ibid). This was digested with PstI and BstEII, the 3.5 kb vector fragment was purified and the PstI/BstEII Vh PCR fragment was ligated and transformed into *E. coli* TGI to produce a 340Vh recombinant. The 340Vh plasmid was next digested with SacI and XhoI and the SacI/XhoI Vk PCR fragment was cloned into the vector fragment to produce a 340 scFv-producing TGI cells.

For cloning into a T7 polymerase transcription vector, the 340 scFv was amplified using forward primer SEQ ID NO: 41 5'-CCG TAT AGA TCT ATG GAA GTG CAT CTG CAG GAG TCT GGG-3' and reverse primer SEQ ID NO: 42 5'-CCG TAT GGA TCC TGC AGC CAC AGT CCG TTT GAT-3'. The PCR fragment was digested with BglII and BamHI and cloned into the *E. coli* expression vector pET-9 (Promega) at the BamHI site. This plasmid contains the promoter, translational start site and terminator from the bacteriophage T7 gene 10. The resultant plasmid was designated pEGFR1. The anti-fluorescein scFv DNA sequence was generated as described by Mallender, Carrero & Voss (Journal of Biological Chemistry, vol 271 (1996), p5338–5346) from the expression vector pGX8773 using forward primer SEQ ID NO: 43 fox1 5'-CCG TAT AGA TCT GAT GTC GTG ATG ACC CAA ACT-3' and reverse primer SEQ ID NO: 44 rox1 5'-CCG TAT GGA TTC TGA GGA GAC GGT GAC TGA GGT-3'. This fragment was generated by PCR and then cloned into the pET-9 vector as described above and designated pOX1.

A spacer sequence based on the glycine rich linkers of gene III of filamentous phage M13 was generated by performing PCR on a preparation of double stranded M13 DNA using primers m13 f1, m13r1, m13f2 and m13 r2 as previously.

Two sets of PCR reactions were performed using primer combination m13f1 and m13r1 or with m13f2 and m13r2. These two sets of reactions generated two populations of products, one with a 5' BglII and 3' XhoI and one with a 5' SalI and 3' BclI restriction sites. The restriction sites were included to facilitate the construction of multimers of the 30 amino acid linker. The BglII/XhoI PCR products were double digested and phosphatased and then ligated with the digested SalI/BclI PCR products. In this way multimers ligated only 5' to 3' (which could be confirmed by digestion) would be formed. A 900 bp fragment was isolated by agarose gel electrophoresis and purified using Wizard PCR purification columns (Promega) according to manufacturers instructions. The fragment was then digested with BglII and BclI and cloned into the BamHI site of pEGFR1 and pOX1 downstream of the scFv fragments to generate pEGFR2 and pOX2 respectively.

The HIV transactivation response element (TAR) sequence was inserted downstream from the M13 spacer segment by ligating the BclI digested 900 bp spacer fragment (generated as described above) to selfannealed oligonucleotides TAR1 and TAR2 encoding the HIV TAR as previously.

The fragment was repurified and cloned into the BamHI site of pEGFR2 and pOX2 to generate pEGFR3 and pOX3. Following cloning, sequencing of the PCR generated inserts was performed by the dideoxy chain termination method using a double-stranded plasmid DNA template (Kraft et al., BioTechniques 6 (1988), p544) and Sequenase (Amersham) using T7 sequencing primers.

In vitro transcription of the constructs pEGFR3 and pOX3 was performed using the RiboMAX large scale RNA production system (Promega) according to the manufacturers instructions. The resultant mRNA was purified using PolyATtract system (Promega) and mixed in a 1:1 ratio (w/w).

In vitro translation was performed in an *E. coli* S-30 system as described by Chen and Zubay (ibid) modified as described by Hanes and Pluckthun (ibid). After 10 minutes of translation, a preparation of SRP (produced by the method of Romisch et al., Nature 340, (1989), p478–482) was added and the translation continued for a further 10 minutes. The translation was stopped and the mixture centrifuged as described by Hanes and Pluckthun (ibid). The translation reactions were then diluted into PBS. Cells were grown up and harvested in trypsin/EDTA and washed twice in PBS before being resuspended DMEM/10% FBS at $2 \times 10^6$ cells/ml either as a mixture of $10^6$ A431 and $10^6$/ml EGFR HeLa cells or $2 \times 10^6$/ml of each individual cell type. In each case, either tat$^+$ transformed or tat untraisformed cells were used. 100 ul of cell suspension was then mixed with the translation reaction derived from an original 1 ug of library DNA in 100 ul BBS plus 0.1% sodium carboxymethylcellulose (ICI, Teeside, UK) at 37c for 1 hour. Cells were then centrifuged, washed twice in PBS containing 0.1% (v/w) BSA and resuspended in 100 ul of this buffer.

Tat-bound mRNA was recovered by dissociation of mRNA in EDTA buffer as described by Hanes and Pluckthun (ibid) followed by passage through a column comprising polyclonal anti-tat antibody on protein A beads prepared according to *Antibodies, A Laboratory Manual* ibid. Washing and dissociation of retained ribosome complexes, isolation of mRNA, reverse-transcription PCR and repeated transcription-translation were as described by Hanes and Pluckthun (ibid). After 2 rounds of ribosome display, the PCR products were cloned into pUC18 for sequencing and determination of the original scFv's in the selected population of genes. For this determination, the inserts in at least 50 pUC18 clones were partially sequenced in order for the identity of the clones to be determined. The results, as shown in table 3, indicate that the tat secreted from A431 cells provides a selective advantage to translated anti-EGFR mRNA over anti-fluorescein scFv which does not bind to A431 cells. Neither tat nor EGFR HeLa cells provide such a selective advantage showing that both binding to a target cell and tat secretion are required for selection.

EXAMPLE 18
Ligand-directed Ribosome Display

The monoclonal antibody 340 (PCT00443) was used as a ligand for the epidermal growth factor receptor (EGFR). 1mg antibody 340 was conjugated to 10 mg PLC (Sigma, Poole, UK; #P4039) using Sulpho-MBS (m-Maleimidobenzoyl-N-hydroxysuccinimide ester) (Pierce,Chester, U.K.; #22312) as cross-linking reagent. Conjugation was performed using the manufacturers recommended protocol. Reagents were desalted and purified post-onjugation using G25 Sephadex columns (Pharrnacia, Milton Keynes, UK; #17-0851-01) and dialysis, and conjugation verified by SDS polyacrylamide gel electrophroresis and Coomasie Blue staining according to standard protocols (*Antibodies, A Laboralory Manual*, ibid).

Methods for producing monoclonal and polyclonal anti-EGFR antibodies were standard methods essentially as described in *Antibodies, A Laboratory Manual* ibid. Mouse monoclonal antibodies reactive to EGFR were obtained using the human breast carcinoma MDA-MB468 as immunogen for BALB/c mice. Primary and secondary injections were both with $5 \times 10^5$ cells intraperitoneally 3 weeks apart followed another week by 4 injections over 2 days into the tail vein. After a further 5 days, spleens were removed and fused to SP2/0 mouse myeloma cells according the procedure of Kennet, R H; in *Methods Enzymol.*, vol 58 (1978) p345–359. Pooled hybridomas were tested for EGFR binding activity as described by Modjtahedi, H et al., Br J Cancer, vol 67 (1993) p247–253 and expanded to $5 \times 10^7$ cells for mRNA isolation using a Fast Track mRNA isolation kit (InVitrogen, NV Leek, Netherlands). mRNA was then processed using a Pharmacia Recombinant Phage Antibody System kit (Pharmacia, Milton Keynes, UK) according to the manufacturer's instructions to produce a library of $10^7$ cfu bacteriophage from the pCANTAB5 vector.

For transcription, the vector pET-5 was used (Promega, Southampton, UK) to provide a promoter, translational start site and terminator from the bacteriophage T7 gene 10. Initially, a 3' spacer sequence was cloned into this vector based on the glycine-rich linkers of gene III of filamentous phage M13 which was generated by PCR using the following primers m13f1, m13r1, m13f2 and m13r2 as previously.

Two sets of PCR reactions were performed using primer combination m13f1 and m13r1 or with m13f2 and m13r2. These two sets of reactions generated two populations of products, one with a 5' BglII and 3' XhoI and one with a 5' SalI and 3' BclI restriction sites. The restriction sites were included to facilitate the construction of multimers of the 30 amino acid linker. The BglII/XhoI PCR products were double digested and phosphatased and then ligated with the digested SalI/BclI PCR products. In this way multimers ligated only 5' to 3' were formed. A 900 bp multimer was selected, BcA digested and ligated to self annealed synthetic oligonucleotides TAR1 and TAR2 encoding the HIV TAR response element as previously.

The fragment was repurified, BglII digested and cloned into the BamHI site of pET-5 to yield the plasmid pET-S5III with the gene III/TAR insert, a downstream BamHI site but no upstream site.

Inserts in pCANTAB5 were amplified using the following primer SEQ ID NOS: 45–46: forward: 5' CCG TAT GGA TCC GCG GCC CAG CCG GCC ATG GC3'. reverse: 5' CCG TAT GGA TCC CCC GTG ATG GTG ATG ATG ATG3'. PCR amplification reactions were performed using Boehringer Expand High Fidelity PCR system. Reaction conditions for amplification of DNA fragments were 1× Expand HF buffer, 2.5 mM MgCl2, 4 mM of each dNTP, 2.5 units of polymerase, 10 ng template DNA and 30 pmol of primer DNA. Reactions were incubated in a Perkin Elmer thermal cycler 480 using the following programme: 92° C. for 5 min, 67 C for 5 min, 72° C. for 1 min, followed by 30 cycles of 92° C. for 1 min, 67° C. for 1 min and 72° C. for 1 min. The resultant 795 bp fragment was then purified using Wizard PCR purification columns (Promega) and cloned into the modified vector pET-5III by digesting the PCR product with BamHI and the vector with MboI.

In vitro transcription of 10 ug of the mixed library DNA was performed using the RiboMAX large scale RNA production system(Promega) according to the manufacturers instructions. The resultant mRNA was purified using PolyATtract system (Promega).

In vitro translation was performed in an *E. coli* S-30 system as described by Chen and Zubay (ibid) modified as described by Hanes and Pluckthun (PNAS, vol 94 [10] :4937, 1997) and supplemented with HIV tat 37–72 peptide (Naryshkin et al., Biochemistry vol 36 (1997) p3496–3505). The translation was stopped after 10 minutes and the mixture centrifuged as described by Hanes and Pluckthun (ibid).

For the liposomal-tat preparation, liposomal vesicles were produced by mixing the lipids L-phosphatidylcholine and oleoyl-palmitoyl cholesterol. Tat 37–72 peptide at a concentration of 100 mM in 10 mM Tris pH8.0 was added to 10 mg of a mixture of 1.5:1 L-alpha-phophatidylcholine and cholesterol (Sigma Poole U.K; #13906). Vesicles were formed following repeated cycles of vigorous mixing and allowing the solution to stand at room temperature. The volume of the liposomal solution was increased by addition of 10 mM Tris 10 mM pH8.0 and liposomes purified from unincorporated components by gel filtration through a G25 Sephadex column (Pharmacia, Uppsala Sweden; #17-0851-01) with borate buffered saline (BBS; 0.2M sodium metaborate, 7.5g/l NaCl, 1.8g/l CaCl2.2H20, pH adjusted to 7.0 with boric acid). Integrity of the eluted liposomes was assessed by microscopy where intact liposomes were compared to control preparations lysed by treatment with a solution of 1% (v/v) NP-40 (Pierce, Chester, U.K.; #28324). Liposomes were diluted in BBS to give a final concentration of 1OrnM tat 37–72 peptide.

Anti-tat antibody was made using the tat peptide 37–72 which was conjugated via its N-terminal cysteine residue to KLH using MBS according to *Antibodies, A Laboratory Manual* ibid. 10 ug of the conjugate was used to immunise Balb/c mice as above and serum was collected and used at 1:100 dilution in the further experiments. Rabbit polyclonal antibody against 791T/36 cells (Doran M et al., Br J Cancer, vol 62 (1990) p500) were made according to *Antibodies, A Laboratory Manual* ibid.

791T/36 cells were grown up and harvested in trypsin/EDTA and washed twice in RPMI1640 medium before being resuspended in PBS/0.1% BSA at $5 \times 10^5$ cells/ml. 100 ul of cell suspension was then mixed with 100 ul of 100 ug/ml of 340-PLC conjugate in PBS supplemented with 0.1% (w/v) bovine serum albumin (BSA) (Sigma, #A7906, Poole, UK) and incubated at 37° C. for 1 hour. Cells were then centrifuged and washed twice in ice-cold PBS/0. 1% BSA and resuspended in 100 ul PBS. The translation reaction derived from an original 1 ug of library DNA was then added in 100 ul PBS and incubated at 37° C. for a further 1 hour. Cells were again centrifuged, washed twice in PBS/0.1% BSA and resuspended in 100 ul of this buffer. 100 ul prepared liposome suspension was added and incubated for 1 hour at 37° C. Cells were subsequently washed for 3×5 minutes in PBS/0.1% BSA.

Tat-bound mRNA was recovered by dissociation of mRNA in EDTA buffer as described by Hanes and Pluckthun (ibid) followed by passage through a column comprising polyclonal anti-tat antibody on protein A beads prepared according to Antibodies, A Laboratory Manual ibid. Washing and dissociation of retained ribosome complexes, isolation of mRNA, reverse-transcription PCR and repeated transcription-translation with a final round of labelling using 35S methionine label at 50 uCi/ml (Amersham International, Amersham, UK) were as described by Hanes and Pluckthun (ibid). After 3 rounds of ribosome display on 791 T cells, the PCR products were transcribed and translated with 35S methionine and the mixture was then applied to Immulon 2 96-well microtitre plates (Dynatech, Chantilly, Va., USA) coated with an EGFR antigen preparation from human placenta made using an antibody 340 immunoaffinity column (PCT00443) and coated onto the plates in coating buffer according to the manufacturer's protocol. Approximately 1 ug of translated protein complex was added per well either with 0. lug BSA alone or with lug 340 antibody or 5 ug polyclonal anti-EGFR (as above). Plates were incubated for 1 hour, washed 5 times with PBS containing 0.1% Tween 20 (Sigrna) and bound protein was eluted with 0.1 M triethylamine and counted in a scintillation counter. The results, as shown in table 4 as an average of 3 determinations (SD<10%), indicate specific binding of translated protein derived from triplicate mRNA/ribosome/protein complexes eluted from 791T cells using anti-tat columns but not from triplicate complexes eluted and processed without anti-tat enrichment or triplicate complexes directly from the DNA library. Furthermore, the lack of inhibition of binding by 340 antibody, which comprised the PLC-labelled ligand in the experiment, and positive inhibition by ployclonal anti-791T sera indicates that binding is specific to epitopes on EGFR other than that of 340.

EXAMPLE 19
Protein-protein Binding by Liposomal Selection

The self-dimerising human IL-5 protein was used to demonstrate complementation of phospholipase C (PLC) from it's two inactive subunits, PLC 1-246 (PL1) and PLC247-370 (PL2) and subsequent lysis of liposomes. A human IL-5 gene (R&D Systems, Abingdon, UK) was PCR amplified from pUC18 using the following primer SEQ ID NOS: 47-49:

PCR amplification reactions were performed using the Boehringer Expand High Fidelity PCR system (Boehringer, Lewes, UK). Reaction conditions for amplification of DNA fragments were 1× Expand HF buffer, 2.5 mM MgCl2, 4 mM of each dNTP, 2.5 units of polymerase, 10 ng template DNA and 30 pmol of primer DNA. Reactions were incubated in a thermal cycler using the following programme: 92° C. for 5 min, 53–67° C. (depending on primer sequence) for 5 min, 72° C. for 1 min, followed by 30 cycles of 92° C. for 1 min, 53–67° C. for 1 min and 72° C. for 1 min., The resultant fragments were then purified using Wizard PCR purification columns (Promega) and cloned into the E. coli expression vector pET-9 (Promega, Southampton, UK) at the BamHl site by digesting the PCR product and vector with BglII and BamHI according to the manufacturer's instructions. This plasmid contains the promoter, translational start site and terminator from the bacteriophage T7 gene 10. The resultant plasmids were designated pIL5a (SmaI site) and pIL5b (SmaI and NcoI sites) or pDIG (anti-digoxin scFv).

pIL5b and pDIG were firther modified as follows: A spacer sequence based on the glycine rich linkers of gene III of filamentous phage M13 was generated by performing PCR on a preparation of double stranded M13 DNA using primers m13f1, m13r1, m13r2 and m13f2 as in example 17.

Two sets of PCR reactions were performed using primer combination m13f1 and m13r1 or with m13f2 and m13r2. These two sets of reactions generated two populations of products, one with a 5' BglII and 3' Xhol and one with a 5' SalI and 3' BclI restriction sites. The restriction sites were included to facilitate the construction of multimers of the 30 amino acid linker. The BglII/XhoI PCR products were double digested and phosphatased and then ligated with the digested SalI/BclI PCR products. In this way multimers ligated only 5' to 3' (which could be confirmed by digestion) would be formed. A 900 bp fragment was isolated by agarose gel electrophoresis and purified using Wizard PCR purification columns (Promega) according to manufacturers instructions. The HIV trsactivation response element (TAR) sequence was inserted downstream from the M13 spacer segment by ligating the BclI digested 900 bp spacer fragment (generated as described above) to self annealed oligonucleotides TAR1 and TAR2 encoding the HIV TAR as in example 17.

```
il5f1:   CCG TAT AGA TCT GAA ATT CCC ACT AGT GCA TTG
                 Bg/II il5r1:   CCG TAT GGA TCC GAC GTC CTC AAG CTT GGA ATA TTATCA
                 BamHI                HindIII         Stop -CCC GGG ACT TTC TAT TAT CCA CTC GGT
         SmaI il5r2:   CCG TAT GGA TCC GAC GTC CTC AAG CTT GGA ATA
                 BamHI                HindIII -CCC GGG CCA TGG ACT TTC TAT TAT CCA CTC GGT
         SmaI  NcoI
```

As a control for IL-5, a single chain antibody genes (scFv) specific for digoxin (Tang et al., Journal of Biological Chemistry 270 (1995) p7829–7835) was also cloned starting from a pCANTAB vector (Tang et al.) using forward primer SEQ ID NO: 5 fdig1: CCG TAT AGA TCT CAG GTC AAA CTG CAG GAG TCT and reverse primer SEQ ID NO: 51 rdig1: CCG TAT GGA TCC CCG TTT TAT TTC CAA CTT TGT.

This fragment was repurified, digested with BglII and cloned into the BamHI site of pIL5b or pDIG too give pIL5b/M13/TAR and pDIG/M13/TAR respectively.

The PLC-encoding plasmid pT2.2 (Titball R et al., Infection and Immunity, 57 (1989) p367–376) was subjected to PCR (conditions as above) using the following primer pair SEQ ID NOS: 52–57:

PL1for: CCG TAT CCA TGG GGA TGG AAA GAT TGA TGG AAC

PL1bck: CCG TAT CCC GGG GAT ACA TCG TGT AAG AAT CTA

PL2for1: CCG TAT CCC GGG TAA TGA TCC ATC AGT TGG AAA

PL2for2: CCG TAT AGA TCT TAA TGA TCC ATC AGT TGG AAA

PL2bck1: CCG TAT AAG CTT TTA TTT TGT AAA TAC CAC C

PL2bck2: CCG TAT GAA TTC AAG CTT TTA TTT TGT AAA TAC CAC C

The PL1 fragment from PCR with PL1 primers was digested with NcoI and SmaI and cloned into NcoI/SmaI-digested pIL5b(or pDIG)/M13/TAR to give pIL5(pDIG)/PL1/M13/TAR. The PL2 fragment from PCR with PL2for1 and PL2bck1 primers was digested with SmaI and HindIII and cloned into SmaI/HindIII-digested pIL5a to give pIL5/PL2. The PL2 fragment from PCR with PL2for2 and PL2bck2 primers was digested with BglII and BamHI and cloned into BamHI digested pET-9 to give pPL2.

In vitro transcription of the plasmid constructs was performed using the RiboMAX large scale RNA production system(Promega) according to the manufacturers instructions. The resultant mRNA was purified using PolyATtract system (Promega).

For the liposomal-tat preparation, liposomal vesicles were produced by mixing the lipids L-phosphatidylcholine and oleoyl-palmitoyl cholesterol. Tat 37–72 peptide at a concentration of 100 mM in 10 mM Tris pH8.0 was added to 10 mg of a mixture of 1.5:1 L-alpha-phophatidylcholine and cholesterol (Sigma Poole U.K; #13906). Vesicles were formed following repeated cycles of vigorous mixing and allowing the solution to stand at room temperature. The volume of the liposomal solution was increased by addition of 10 mM Tris 10 mM pH8.0 and liposomes purified from unincorporated components by gel filtration through a G25 Sephadex column (Pharmacia, Milton Keynes, UK; #17–0851–01) with borate buffered saline (BBS; 0.2M sodium metaborate, 7.5g/l NaCl, 1.8g/l $CaCl_2.2H_2O$, pH adjusted to 7.0 with boric acid). Integrity of the eluted liposomes was assessed by microscopy where intact liposomes were compared to control preparations lysed by treatment with a solution of 1% (v/v) NP40 (Pierce, Chester, U.K.; #28324). Liposomes were diluted in BBS to give a final concentration of 10mM tat 37–72 peptide.

Anti-tat antibody was made using the tat peptide 37–72 which was conjugated via its N-terminal cysteine residue to KLH using MBS according to Antibodies, A Laboratory Manual (ibid). 10 lg of the conjugate was used to immunise Balb/c mice as above and serum was collected and used at 1:100 dilution in the further experiments.

In vitro translation was performed in an *E. coli* S-30 system as described by Chen and Zubay (ibid) modified as described by Hanes and Pluckthun (ibid). The translation was stopped and the mixture centrifuged as described by Hanes and Pluckthun (ibid). 100 μl of prepared liposomal-tat suspension was added to 100 l translation mixture and incubated for 1 hour at 37° C. Translation reactions were then passed through a column comprising polyclonal anti-tat antibody on protein A beads prepared according to *Antibodies, A Laboratory Manual* ibid. Washing and dissociation of retained ribosome complexes, isolation of mRNA, reverse-transcription PCR and repeated transcription-translation were as described by Hanes and Pluckthun (ibid).

Aliquots of mRNA derived from either of the plasmids pIL5a, pIL5a/PL2 or pPL2 (encoding the "model ligands" IL-5, IL-5/PL2 fusion protein or PL2 alone) and rabbit beta globin mRNA ("globin") were mixed in a 1:1 w/w ratio with a 1:9 w/w mixture of mRNAs derived from the plasmids pIL5b/PL1/M13/TAR and pDIG/PL1/M13/TAR (encoding the "model receptors" IL-5/PL1 fusion protein or anti-digoxin scFv/PL1 fusion) for subsequent translation and separation of tat peptide-tagged mRNAs. All reactions were in triplicate. The identity of the mRNAs (IL-5 or DIG) were subsequently determined from a minimum of 50 clones in pUC18. The results of this analysis are shown in table 5 (average of 3 determinations; SD<10%) and indicate that the use of IL-5/PLC ligand provides a strong selection of mRNAs encoding IL-5 in preference to anti-digoxin scFv. This indicates that the homodimerisation of IL-5 brings together the PL1 and PL2 subunits of PLC for efficient lysis of liposomes and release of tat which binds to anti-IL5 mRNA in the translation complexes associated with IL-5 dimers.

TABLE 1

| dig/fluor mRNA ratio | tat | SRP | Ligand | |
|---|---|---|---|---|
| | | | Digoxin % of anti-dig scFv clones | Fluorescein % of anti-FITC scFv clones |
| 1:99 | − | − | 18 | n/a |
| | + | + | 96 | n/a |
| 5:95 | − | − | 26 | n/a |
| | + | − | 94 | 100 |
| | + | + | 88 | 100 |
| 50:50 | − | − | 82 | n/a |
| | + | − | 100 | 100 |
| | + | + | 100 | n/a |
| 95:5 | − | − | n/a | 36 |
| | + | − | 100 | 94 |
| | + | + | n/a | 98 |
| 99:1 | − | − | n/a | 28 |
| | + | − | 100 | 100 |
| | − | + | n/a | 40 |
| | + | + | n/a | 94 | n/a not measured

TABLE 2

| | ScFv | | | |
|---|---|---|---|---|
| Target | 340 +oligo/SA | 340 −oligo/SA | αPs +oligo/SA | αPs −oligo/SA |
| | Experiment 1 (SDs < 10%) | | | |
| anti-FLAG | 14.1 | 9.3 | 68.9 | 43.8 |
| anti-His | 65.3 | 40.5 | 16.7 | 12.6 |
| Pseudomonas | 5.2 | 2.4 | 58.4 | 32.2 |
| | Experiment 2 (SDs < 10%) | | | |
| anti-FLAG | 9.9 | 6.4 | 42.8 | 29.3 |
| anti-His | 52.1 | 26.5 | 8.7 | 4.2 |
| Pseudomonas | 6.1 | 3.2 | 37.5 | 22.1 |

(results are expressed as % of labelled RNA bound to specific target)

TABLE 3

| | % EGFR scFv | |
|---|---|---|
| | tat⁻ | tat⁺ (transformed) |
| A431 | n/a | 98 |
| EGFR HeLa | 29 (7 clones) | 46 |
| A431 + EGFR HeLa | 64 | 100 |

TABLE 4

| | cpm - $^{35}$S | | |
|---|---|---|---|
| Origin of Translation Complex | Translation Mix alone | Translation Mix + 340 Mab | Translation Mix + anti-791T |
| 791T selected | 2050 | 1750 | 340 |
| 791T/anti-tat | 21210 | 18420 | 3930 |
| selected Library only | 130 | 100 | 110 |

TABLE 5

| Model Ligand | % IL5 clones |
|---|---|
| Globin | 8 |
| IL-5 | 12 |
| IL-5/PL2 | 100 |
| PL2 | 18 |

What is claimed is:

1. A method of screening proteins and polypeptides to identfy a protein or polypeptide having a biological activity of interest, which comprises the sequential steps of (i) forming a first library, which comprises polynucleotide clones, (ii) expressing by in vitro transcription and translation an individual protein or polypeptide from each clone in the first library from a second library, which comprises individual proteins and polypeptides derived from each polynucleotide clone in the first library, (iii) assaying the second library to select an individual protein or polypeptide in the second library having a biological activity of interest; and (iv) identfying the protein or polypeptide selected in step (ii, by sequencing a polynucleotice clone from the first library that encodes the individual protein or polypeptide selected from the second library in step (iii), wherein the first library of polynucleotide clones in step (i) is a library of transformed bacterial cell colonies; the second library of individual proteins and polypeptides is formed by in vitro transcription and translation of a polynucleotide from each bacterial cell colony in step (ii); and the biological activity of interest in step (iii) is the ability to effect a post-translational modification of a protein or polypeptide from a tissue extract.

2. The method of claim 1 wherein the tissue extract is a human brain tissue extract.

3. The method of claim 1 wherein the post-transitional modification is proteolysis.

4. The method of claim 1 wherein the post-translational modification is phosphorylation.

5. A method for screening proteins and polypeptides to identify a protein or polypeptide having a biological activity of interest, which comprises the sequential steps of:

(i) generating a first library, which comprises polynucleotides in the form of clones selected from the group consisting of DNA molecules, RNA molecules, cell colonies, and plaques;

(ii) expressing a polynucleotide from each clone in the first library using in vitro transcription and translation to generate a second library, which comprises individual proteins and polypeptides;

(iii) dispensing an aliquot of each protein or polypeptide in the second library into a specific locus in a multi-well plate or a solid phase to form a protein and polypeptide array;

(iv) contacting the protein and polypeptide array generated in step (iii) with a material selected from the group consisting of a cell extract, a tissue extract, a cell sample, and a tissue sample;

(v) assaying each protein and polypeptide in the array to select an individual protein or polypeptide that interacts with the material contacting the array in step (iv), and (vi) identifying the individual protein or polypeptide selected in step (v) by sequencing the polynucleotide that encodes the selected protein or polypeptide;

wherein the interaction of the protein or polypeptide with the material contacting the array in step (v) is an interaction selected form the group consisting of modification of a protein or polypeptide in the array, binding of a protein or polypeptide in the array to a molecule from a cell, and binding of a protein or polypeptide in the array to a molecule form a tissue and wherein the first library of polynucleotide clones in step (i) is a library of transformed bacterial cell colonies; the protein and polypeptide array is contacted with a tissue extract in step (iii); and in step (iv) the protein and polypeptide array interacts with tissue extract by post-translational modification of a protein or polypeptide from the tissue extract.

6. The method of claim 5 wherein the tissue extract is a human brain tissue extract.

7. The method of claim 5 wherein the post-translational modification is proteolysis.

8. The method of claim 5 wherein the post-translational modification is phosphorylation.

* * * * *

```
                          SEQUENCE LISTING

<160> NUMBER OF SEQ ID NOS: 64

<210> SEQ ID NO 1
<211> LENGTH: 13
<212> TYPE: DNA
<213> ORGANISM: Kozak translation initiation sequence consensus

<400> SEQUENCE: 1
gccgccacca tgg                                                        13

<210> SEQ ID NO 2
<211> LENGTH: 66
<212> TYPE: DNA
<213> ORGANISM: linker sequence between HindIII and Eco RI sites

<400> SEQUENCE: 2
agcttggccc agccggccat ggcccaggtc caactgcagg agctcgagat caaacgggcg     60
gccgcg                                                                66

<210> SEQ ID NO 3
<211> LENGTH: 66
<212> TYPE: DNA
<213> ORGANISM: linker sequence between HindIII and Eco RI sites

<400> SEQUENCE: 3
aattcgcggc cgcccgtttg atctcgagct cctgcagttg gacctgggcc atggccggct     60
gggcca                                                                66

<210> SEQ ID NO 4
<211> LENGTH: 14
<212> TYPE: PRT
<213> ORGANISM: amino acid linker sequence

<400> SEQUENCE: 4

Glu Gly Lys Ser Ser Gly Ser Gly Ser Glu Ser Lys Val Asp
1               5                   10
```

<210> SEQ ID NO 5
<211> LENGTH: 28
<212> TYPE: DNA
<213> ORGANISM: primer sequence

<400> SEQUENCE: 5
cagctgcagg agtctggggg aggcttag                                    28

<210> SEQ ID NO 6
<211> LENGTH: 36
<212> TYPE: DNA
<213> ORGANISM: primer sequence

<400> SEQUENCE: 6
tcagtagacg gtgaccgagg ttccttgacc ccagta                           36

<210> SEQ ID NO 7
<211> LENGTH: 26
<212> TYPE: DNA
<213> ORGANISM: primer sequence

<400> SEQUENCE: 7
gtgacattga gctcacacag tctcct                                      26

<210> SEQ ID NO 8
<211> LENGTH: 28
<212> TYPE: DNA
<213> ORGANISM: primer sequence

<400> SEQUENCE: 8
cagcccgttt tatctcgagc ttggtccg                                    28

<210> SEQ ID NO 9
<211> LENGTH: 47
<212> TYPE: DNA
<213> ORGANISM: RD 5' HIS primer sequence

<400> SEQUENCE: 9
gcggatccca tatgcaccat catcaccatc accaggtgca gctgcag               47

<210> SEQ ID NO 10
<211> LENGTH: 30
<212> TYPE: DNA
<213> ORGANISM: synthetic oligonucleotide

<400> SEQUENCE: 10
agaatacagg gtccaaatag aatccagggt                                  30

<210> SEQ ID NO 11
<211> LENGTH: 50
<212> TYPE: DNA
<213> ORGANISM: synthetic oligonucleotide

<400> SEQUENCE: 11
ctacctataa aaataggcgt atcacgaggc cctttcgtct tcaataattc            50

<210> SEQ ID NO 12
<211> LENGTH: 54
<212> TYPE: DNA
<213> ORGANISM: synthetic oligonucleotide

<400> SEQUENCE: 12
agcgaattca ccctggattc tatttggacc ctgtattcta cctataaaaa tagg    54

<210> SEQ ID NO 13
<211> LENGTH: 61
<212> TYPE: DNA
<213> ORGANISM: synthetic oligonucleotide

<400> SEQUENCE: 13
ggtttccctc tagaatacag ggtccaaata gaatccaggg taagaaggag atatacatat    60
g    61

<210> SEQ ID NO 14
<211> LENGTH: 67
<212> TYPE: DNA
<213> ORGANISM: synthetic oligonucleotide

<400> SEQUENCE: 14
atatatatgt cgacgaaatt aatacgactc actataggga gaccacaacg gtttccctct    60
agaatac    67

<210> SEQ ID NO 15
<211> LENGTH: 50
<212> TYPE: DNA
<213> ORGANISM: synthetic oligonucleotide

<400> SEQUENCE: 15
atatatatgt cgacgaaatt aatacgactc actataggga gaccacaacg    50

<210> SEQ ID NO 16
<211> LENGTH: 33
<212> TYPE: DNA
<213> ORGANISM: forward primer sequence fdig1

<400> SEQUENCE: 16
ccgtatagat ctcaggtcaa actgcaggag tct    33

<210> SEQ ID NO 17
<211> LENGTH: 66
<212> TYPE: DNA
<213> ORGANISM: reverse primer sequence rdig1

<400> SEQUENCE: 17
ccgtatagat ctcaggtcaa actgcaggag tctccgtatg gatccccgtt ttatttccaa    60
ctttgt    66

<210> SEQ ID NO 18
<211> LENGTH: 30
<212> TYPE: DNA
<213> ORGANISM: forward primer sequence fox1

<400> SEQUENCE: 18
ccgtatagag atgtcgtgat gacccaaact    30

<210> SEQ ID NO 19
<211> LENGTH: 33
<212> TYPE: DNA
<213> ORGANISM: reverse primer sequence rox1

<400> SEQUENCE: 19
ccgtatggat cctgaggaga cggtgactga ggt    33

-continued

<210> SEQ ID NO 20
<211> LENGTH: 33
<212> TYPE: DNA
<213> ORGANISM: primer sequence m13f1

<400> SEQUENCE: 20
ccgtatagat ctggctttaa tgaggatcca ttc                              33

<210> SEQ ID NO 21
<211> LENGTH: 33
<212> TYPE: DNA
<213> ORGANISM: primer sequence m13r1

<400> SEQUENCE: 21
ccgtatctcg agctgtagcg cgttttcatc ggc                              33

<210> SEQ ID NO 22
<211> LENGTH: 33
<212> TYPE: DNA
<213> ORGANISM: primer sequence m13f2

<400> SEQUENCE: 22
ccgtatgtcg acggctttaa tgaggatcca ttc                              33

<210> SEQ ID NO 23
<211> LENGTH: 33
<212> TYPE: DNA
<213> ORGANISM: primer sequence m13r2

<400> SEQUENCE: 23
ccgtattgat cactgtagcg cgttttcatc ggc                              33

<210> SEQ ID NO 24
<211> LENGTH: 90
<212> TYPE: DNA
<213> ORGANISM: primer sequence fdig2

<400> SEQUENCE: 24
ccgtatagat ctatgggatg gagctgtatc atcctcttct tggtagcaac agctacaggt    60
gtccactccc aggtcaaact gcaggagtct                                     90

<210> SEQ ID NO 25
<211> LENGTH: 90
<212> TYPE: DNA
<213> ORGANISM: primer sequence fox2

<400> SEQUENCE: 25
ccgtatagat ctatgggatg gagctgtatc atcctcttct tggtagcaac agctacaggt    60
gtccactccg atgtcgtgat gacccaaact                                     90

<210> SEQ ID NO 26
<211> LENGTH: 21
<212> TYPE: DNA
<213> ORGANISM: oligonucleotide TAR1

<400> SEQUENCE: 26
gatcagccag atttgagcag c                                              21

<210> SEQ ID NO 27
<211> LENGTH: 21
<212> TYPE: DNA
<213> ORGANISM: oligonucleotide TAR2

-continued

<400> SEQUENCE: 27
gatcgctgct caaatctggc t    21

<210> SEQ ID NO 28
<211> LENGTH: 33
<212> TYPE: DNA
<213> ORGANISM: primer sequence il5f1

<400> SEQUENCE: 28
ccgtatagat ctgaaattcc cactagtgca ttg    33

<210> SEQ ID NO 29
<211> LENGTH: 72
<212> TYPE: DNA
<213> ORGANISM: primer sequence il5r1

<400> SEQUENCE: 29
ccgtatggat ccgacgtcct caagcttgga atattatcag tgatggtgat ggtgatgact    60
ttctattatc ca    72

<210> SEQ ID NO 30
<211> LENGTH: 39
<212> TYPE: DNA
<213> ORGANISM: primer sequence il5f2

<400> SEQUENCE: 30
ccgtatagat ctaagcttga aattcccact agtgcattg    39

<210> SEQ ID NO 31
<211> LENGTH: 33
<212> TYPE: DNA
<213> ORGANISM: primer sequence il5r2

<400> SEQUENCE: 31
ccgtatggat ccactttcta ttatccactc ggt    33

<210> SEQ ID NO 32
<211> LENGTH: 27
<212> TYPE: DNA
<213> ORGANISM: biotinylated oligonucleotide

<400> SEQUENCE: 32
ttgaagctct tgtgacggg cgaactc    27

<210> SEQ ID NO 33
<211> LENGTH: 17
<212> TYPE: DNA
<213> ORGANISM: primer sequence HuCK FOR

<400> SEQUENCE: 33
aggcagttcc agatttc    17

<210> SEQ ID NO 34
<211> LENGTH: 18
<212> TYPE: DNA
<213> ORGANISM: primer sequence scAB

<400> SEQUENCE: 34
gtgagctcga tgtcatcc    18

<210> SEQ ID NO 35
<211> LENGTH: 90

```
<212> TYPE: DNA
<213> ORGANISM: primer sequence TATfor

<400> SEQUENCE: 35
ccgtatctcg agatgggatg gagctgtatc atcctcttct tggtagcaac agctacaggt    60
gtccactccg aaccagtcga ccctagactg                                    90

<210> SEQ ID NO 36
<211> LENGTH: 21
<212> TYPE: DNA
<213> ORGANISM: primer sequence TATrev

<400> SEQUENCE: 36
gaattcggat ccttactatt c                                             21

<210> SEQ ID NO 37
<211> LENGTH: 28
<212> TYPE: DNA
<213> ORGANISM: primer sequence 340Vhfor

<400> SEQUENCE: 37
cagctgcagg agtctggggg aggcttag                                      28

<210> SEQ ID NO 38
<211> LENGTH: 36
<212> TYPE: DNA
<213> ORGANISM: primer sequence 340Vhbck

<400> SEQUENCE: 38
tcagtagacg gtgaccgagg ttccttgacc ccagta                             36

<210> SEQ ID NO 39
<211> LENGTH: 26
<212> TYPE: DNA
<213> ORGANISM: primer sequence 340Vkfor

<400> SEQUENCE: 39
gtgacattga gctcacacag tctcct                                        26

<210> SEQ ID NO 40
<211> LENGTH: 27
<212> TYPE: DNA
<213> ORGANISM: primer sequence 340Vkbck

<400> SEQUENCE: 40
cagcccgttt tatctcgagc ttggtcc                                       27

<210> SEQ ID NO 41
<211> LENGTH: 39
<212> TYPE: DNA
<213> ORGANISM: primer sequence 340 scFvfor

<400> SEQUENCE: 41
ccgtatagat ctatggaagt gcagctgcag gagtctggg                          39

<210> SEQ ID NO 42
<211> LENGTH: 33
<212> TYPE: DNA
<213> ORGANISM: primer sequence 340scFvrev

<400> SEQUENCE: 42
ccgtatggat cctgcagcca cagtccgttt gat                                33
```

<210> SEQ ID NO 43
<211> LENGTH: 33
<212> TYPE: DNA
<213> ORGANISM: forward primer sequence fox1

<400> SEQUENCE: 43
ccgtatagat ctgatgtcgt gatgacccaa act      33

<210> SEQ ID NO 44
<211> LENGTH: 33
<212> TYPE: DNA
<213> ORGANISM: reverse primer sequence rox1

<400> SEQUENCE: 44
ccgtatggat cctgaggaga cggtgactga ggt      33

<210> SEQ ID NO 45
<211> LENGTH: 32
<212> TYPE: DNA
<213> ORGANISM: forward primer sequence pCANTAB5

<400> SEQUENCE: 45
ccgtatggat ccgcggccca gccggccatg gc       32

<210> SEQ ID NO 46
<211> LENGTH: 33
<212> TYPE: DNA
<213> ORGANISM: reverse primer sequence pCANTAB5

<400> SEQUENCE: 46
ccgtatggat cccccgtgat ggtgatgatg atg      33

<210> SEQ ID NO 47
<211> LENGTH: 33
<212> TYPE: DNA
<213> ORGANISM: primer sequence il5f1

<400> SEQUENCE: 47
ccgtatagat ctgaaattcc cactagtgca ttg      33

<210> SEQ ID NO 48
<211> LENGTH: 66
<212> TYPE: DNA
<213> ORGANISM: primer sequence il5r1

<400> SEQUENCE: 48
ccgtatggat ccgacgtcct caagcttgga atattatcac ccgggacttt ctattatcca    60
ctcggt                                                               66

<210> SEQ ID NO 49
<211> LENGTH: 66
<212> TYPE: DNA
<213> ORGANISM: primer sequence il5r2

<400> SEQUENCE: 49
ccgtatggat ccgacgtcct caagcttgga atacccgggc catggacttt ctattatcca    60
ctcggt                                                               66

<210> SEQ ID NO 50
<211> LENGTH: 33
<212> TYPE: DNA
<213> ORGANISM: forward primer sequence fdig1

-continued

<400> SEQUENCE: 50
ccgtatagat ctcaggtcaa actgcaggag tct                33

<210> SEQ ID NO 51
<211> LENGTH: 33
<212> TYPE: DNA
<213> ORGANISM: reverse primer sequence rdig1

<400> SEQUENCE: 51
ccgtatggat ccccgtttta tttccaactt tgt                33

<210> SEQ ID NO 52
<211> LENGTH: 33
<212> TYPE: DNA
<213> ORGANISM: primer sequence PL1for

<400> SEQUENCE: 52
ccgtatccat ggggatggaa agattgatgg aac                33

<210> SEQ ID NO 53
<211> LENGTH: 33
<212> TYPE: DNA
<213> ORGANISM: primer sequence PL1bck

<400> SEQUENCE: 53
ccgtatcccg gggatacatc gtgtaagaat cta                33

<210> SEQ ID NO 54
<211> LENGTH: 33
<212> TYPE: DNA
<213> ORGANISM: primer sequence PL2for1

<400> SEQUENCE: 54
ccgtatcccg ggtaatgatc catcagttgg aaa                33

<210> SEQ ID NO 55
<211> LENGTH: 33
<212> TYPE: DNA
<213> ORGANISM: primer sequence PL2for2

<400> SEQUENCE: 55
ccgtatagat cttaatgatc catcagttgg aaa                33

<210> SEQ ID NO 56
<211> LENGTH: 31
<212> TYPE: DNA
<213> ORGANISM: primer sequence PL2bck1

<400> SEQUENCE: 56
ccgtataagc ttttattttg taaataccac c                  31

<210> SEQ ID NO 57
<211> LENGTH: 37
<212> TYPE: DNA
<213> ORGANISM: primer sequence PL2bck2

<400> SEQUENCE: 57
ccgtatgaat tcaagctttt attttgtaaa taccacc            37

<210> SEQ ID NO 58
<211> LENGTH: 8
<212> TYPE: PRT

-continued

```
<213> ORGANISM: FLAG epitope

<400> SEQUENCE: 58

Met Asp Tyr Lys Asp Asp Asp Lys
1               5

<210> SEQ ID NO 59
<211> LENGTH: 53
<212> TYPE: DNA
<213> ORGANISM: primer RD 5' FLAG

<400> SEQUENCE: 59
gcggatccca tatggactac aaagacgatg acgacaaaca ggtgcagctg cag        53

<210> SEQ ID NO 60
<211> LENGTH: 35
<212> TYPE: DNA
<213> ORGANISM: primer RD3'

<400> SEQUENCE: 60
gcgaattcgt ggtggtggtg gtggtgtgac tctcc                            35

<210> SEQ ID NO 61
<211> LENGTH: 19
<212> TYPE: DNA
<213> ORGANISM: Artificial Sequence
<220> FEATURE:
<223> OTHER INFORMATION: primer

<400> SEQUENCE: 61
ggaaacagct atgaccatg                                              19

<210> SEQ ID NO 62
<211> LENGTH: 27
<212> TYPE: DNA
<213> ORGANISM: Artificial Sequence
<220> FEATURE:
<223> OTHER INFORMATION: primer

<400> SEQUENCE: 62
ccatcctaat acgactcact atagggc                                     27

<210> SEQ ID NO 63
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 51
<223> OTHER INFORMATION: n = A,T,C or G
<220> FEATURE:
<221> NAME/KEY: misc_feature
<222> LOCATION: 52
<223> OTHER INFORMATION: n = A,T,C or G

<400> SEQUENCE: 63
ttctagaatt cagcggccgc tttttttttt tttttttttt tttttttttt nn         52

<210> SEQ ID NO 64
<211> LENGTH: 19
<212> TYPE: DNA
<213> ORGANISM: Artificial Sequence
<220> FEATURE:
<223> OTHER INFORMATION: primer
```

```
                              -continued

<400> SEQUENCE: 64
cggtttccct ctagaaata                                            19
```